US011332738B2

(12) United States Patent
Nugent et al.

(10) Patent No.: US 11,332,738 B2
(45) Date of Patent: May 17, 2022

(54) BARCODE-BASED NUCLEIC ACID SEQUENCE ASSEMBLY

(71) Applicant: Twist Bioscience Corporation, South San Francisco, CA (US)

(72) Inventors: Rebecca Nugent, San Francisco, CA (US); Siyuan Chen, San Mateo, CA (US); Ross Kettleborough, San Francisco, CA (US); Elian Lee, Union City, CA (US); Nathan Raynard, San Mateo, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 0 days.

(21) Appl. No.: 16/906,555

(22) Filed: Jun. 19, 2020

(65) Prior Publication Data

US 2021/0071168 A1 Mar. 11, 2021

Related U.S. Application Data

(60) Provisional application No. 62/865,094, filed on Jun. 21, 2019.

(51) Int. Cl.

| | |
|---|---|
| ***C12N 15/10*** | (2006.01) |
| ***C12N 9/22*** | (2006.01) |
| ***C12N 9/12*** | (2006.01) |
| ***C12N 9/00*** | (2006.01) |

(52) U.S. Cl.

CPC .......... *C12N 15/1065* (2013.01); *C12N 9/22* (2013.01); *C12N 9/93* (2013.01); *C12N 15/1031* (2013.01); *C12N 9/1241* (2013.01)

(58) Field of Classification Search

CPC .. C12N 15/1065; C12N 15/1031; C12N 9/93; C12N 9/22; C12N 9/1241

See application file for complete search history.

(56) References Cited

U.S. PATENT DOCUMENTS

| | | | |
|---|---|---|---|
| 3,549,368 | A | 12/1970 | Robert et al. |
| 3,920,714 | A | 11/1975 | Streck |
| 4,123,661 | A | 10/1978 | Wolf et al. |
| 4,415,732 | A | 11/1983 | Caruthers et al. |
| 4,613,398 | A | 9/1986 | Chiong et al. |
| 4,726,877 | A | 2/1988 | Fryd et al. |
| 4,808,511 | A | 2/1989 | Holmes |
| 4,837,401 | A | 6/1989 | Hirose et al. |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

PCT/US2020038679 International Search Report and Written Opinion dated Oct. 28, 2020.

(Continued)

*Primary Examiner* — Jeremy C Flinders
*Assistant Examiner* — Taryn Kimberly Wood
(74) *Attorney, Agent, or Firm* — Wilson Sonsini Goodrich & Rosati

(57) ABSTRACT

Provided herein are methods, systems, and compositions for efficient nucleic acid assembly. Nucleic acid assembly may comprise assembly of variants comprising paired homology.

21 Claims, 39 Drawing Sheets

Specification includes a Sequence Listing.

703

707

709

705

711

Nucleic acid assembly

713

(56) References Cited

U.S. PATENT DOCUMENTS 4,863,557 A 9/1989 Kokaku et al.
4,981,797 A 1/1991 Jessee et al.
4,988,617 A 1/1991 Landegren et al.
5,102,797 A 4/1992 Tucker et al.
5,118,605 A 6/1992 Urdea
5,137,814 A 8/1992 Rashtchian et al.
5,143,854 A 9/1992 Pirrung et al.
5,242,794 A 9/1993 Whiteley et al.
5,242,974 A 9/1993 Holmes
5,288,514 A 2/1994 Ellman
5,299,491 A 4/1994 Kawada
5,368,823 A 11/1994 McGraw et al.
5,384,261 A 1/1995 Winkler et al.
5,387,541 A 2/1995 Hodge et al.
5,395,753 A 3/1995 Prakash
5,431,720 A 7/1995 Nagai et al.
5,445,934 A 8/1995 Fodor et al.
5,449,754 A 9/1995 Nishioka
5,459,039 A 10/1995 Modrich et al.
5,474,796 A 12/1995 Brennan
5,476,930 A 12/1995 Letsinger et al.
5,487,993 A 1/1996 Herrnstadt et al.
5,494,810 A 2/1996 Barany et al.
5,501,893 A 3/1996 Laermer et al.
5,508,169 A 4/1996 Deugau et al.
5,510,270 A 4/1996 Fodor et al.
5,514,789 A 5/1996 Kempe
5,527,681 A 6/1996 Holmes
5,530,516 A 6/1996 Sheets
5,556,750 A 9/1996 Modrich et al.
5,586,211 A 12/1996 Dumitrou et al.
5,641,658 A 6/1997 Adams et al.
5,677,195 A 10/1997 Winkler et al.
5,679,522 A 10/1997 Modrich et al.
5,683,879 A 11/1997 Laney et al.
5,688,642 A 11/1997 Chrisey et al.
5,700,637 A 12/1997 Southern
5,700,642 A 12/1997 Monforte et al.
5,702,894 A 12/1997 Modrich et al.
5,707,806 A 1/1998 Shuber
5,712,124 A 1/1998 Walker
5,712,126 A 1/1998 Weissman et al.
5,739,386 A 4/1998 Holmes
5,750,672 A 5/1998 Kempe
5,780,613 A 7/1998 Letsinger et al.
5,830,643 A 11/1998 Yamamoto et al.
5,830,655 A 11/1998 Monforte et al.
5,830,662 A 11/1998 Soares et al.
5,834,252 A 11/1998 Stemmer et al.
5,843,669 A 12/1998 Kaiser et al.
5,843,767 A 12/1998 Beattie
5,846,717 A 12/1998 Brow et al.
5,854,033 A 12/1998 Lizardi
5,858,754 A 1/1999 Modrich et al.
5,861,482 A 1/1999 Modrich et al.
5,863,801 A 1/1999 Southgate et al.
5,869,245 A 2/1999 Yeung
5,877,280 A 3/1999 Wetmur
5,882,496 A 3/1999 Northrup et al.
5,922,539 A 7/1999 Modrich et al.
5,922,593 A 7/1999 Livingston
5,928,907 A 7/1999 Woudenberg et al.
5,962,272 A 10/1999 Chenchik et al.
5,976,842 A 11/1999 Wurst
5,976,846 A 11/1999 Passmore et al.
5,989,872 A 11/1999 Luo et al.
5,994,069 A 11/1999 Hall et al.
6,001,567 A 12/1999 Brow et al.
6,008,031 A 12/1999 Modrich et al.
6,013,440 A 1/2000 Lipshutz et al.
6,015,674 A 1/2000 Woudenberg et al.
6,017,434 A 1/2000 Simpson et al.
6,020,481 A 2/2000 Benson et al.
6,027,898 A 2/2000 Gjerde et al.
6,028,189 A 2/2000 Blanchard
6,028,198 A 2/2000 Liu et al.
6,040,138 A 3/2000 Lockhart et al.
6,077,674 A 6/2000 Schleifer et al.
6,087,482 A 7/2000 Teng et al.
6,090,543 A 7/2000 Prudent et al.
6,090,606 A 7/2000 Kaiser et al.
6,103,474 A 8/2000 Dellinger et al.
6,107,038 A 8/2000 Choudhary et al.
6,110,682 A 8/2000 Dellinger et al.
6,114,115 A 9/2000 Wagner, Jr.
6,130,045 A 10/2000 Wurst et al.
6,132,997 A 10/2000 Shannon
6,136,568 A 10/2000 Hiatt et al.
6,171,797 B1 1/2001 Perbost
6,180,351 B1 1/2001 Cattell
6,201,112 B1 3/2001 Ach
6,218,118 B1 4/2001 Sampson et al.
6,221,653 B1 4/2001 Caren et al.
6,222,030 B1 4/2001 Dellinger et al.
6,232,072 B1 5/2001 Fisher
6,235,483 B1 5/2001 Wolber et al.
6,242,266 B1 6/2001 Schleifer et al.
6,251,588 B1 6/2001 Shannon et al.
6,251,595 B1 6/2001 Gordon et al.
6,251,685 B1 6/2001 Dorsel et al.
6,258,454 B1 7/2001 Lefkowitz et al.
6,262,490 B1 7/2001 Hsu et al.
6,274,725 B1 8/2001 Sanghvi et al.
6,284,465 B1 9/2001 Wolber
6,287,776 B1 9/2001 Hefti
6,287,824 B1 9/2001 Lizardi
6,297,017 B1 10/2001 Schmidt et al.
6,300,137 B1 10/2001 Earhart et al.
6,306,599 B1 10/2001 Perbost
6,309,822 B1 10/2001 Fodor et al.
6,309,828 B1 10/2001 Schleifer et al.
6,312,911 B1 11/2001 Bancroft et al.
6,319,674 B1 11/2001 Fulcrand et al.
6,323,043 B1 11/2001 Caren et al.
6,329,210 B1 12/2001 Schleifer
6,346,423 B1 2/2002 Schembri
6,365,355 B1 4/2002 McCutchen-Maloney
6,372,483 B2 4/2002 Schleifer et al.
6,375,903 B1 4/2002 Cerrina et al.
6,376,285 B1 4/2002 Joyner et al.
6,384,210 B1 5/2002 Blanchard
6,387,636 B1 5/2002 Perbost et al.
6,399,394 B1 6/2002 Dahm et al.
6,399,516 B1 6/2002 Ayon
6,403,314 B1 6/2002 Lange et al.
6,406,849 B1 6/2002 Dorsel et al.
6,406,851 B1 6/2002 Bass
6,408,308 B1 6/2002 Maslyn et al.
6,419,883 B1 7/2002 Blanchard
6,428,957 B1 8/2002 Delenstarr
6,440,669 B1 8/2002 Bass et al.
6,444,268 B2 9/2002 Lefkowitz et al.
6,446,642 B1 9/2002 Caren et al.
6,446,682 B1 9/2002 Viken
6,451,998 B1 9/2002 Perbost
6,458,526 B1 10/2002 Schembri et al.
6,458,535 B1 10/2002 Hall et al.
6,458,583 B1 10/2002 Bruhn et al.
6,461,812 B2 10/2002 Barth et al.
6,461,816 B1 10/2002 Wolber et al.
6,469,156 B1 10/2002 Schafer et al.
6,472,147 B1 10/2002 Janda et al.
6,492,107 B1 12/2002 Kauffman et al.
6,518,056 B2 2/2003 Schembri et al.
6,521,427 B1 2/2003 Evans
6,521,453 B1 2/2003 Crameri et al.
6,555,357 B1 4/2003 Kaiser et al.
6,558,908 B2 5/2003 Wolber et al.
6,562,611 B1 5/2003 Kaiser et al.
6,566,495 B1 5/2003 Fodor et al.
6,582,908 B2 6/2003 Fodor et al.
6,582,938 B1 6/2003 Su et al.
6,586,211 B1 7/2003 Staehler et al.
6,587,579 B1 7/2003 Bass

(56) References Cited

U.S. PATENT DOCUMENTS 6,589,739 B2 7/2003 Fisher
6,599,693 B1 7/2003 Webb
6,602,472 B1 8/2003 Zimmermann et al.
6,610,978 B2 8/2003 Yin et al.
6,613,513 B1 9/2003 Parce et al.
6,613,523 B2 9/2003 Fischer
6,613,560 B1 9/2003 Tso et al.
6,613,893 B1 9/2003 Webb
6,621,076 B1 9/2003 Van et al.
6,630,581 B2 10/2003 Dellinger et al.
6,632,641 B1 10/2003 Brennan et al.
6,635,226 B1 10/2003 Tso et al.
6,642,373 B2 11/2003 Manoharan et al.
6,649,348 B2 11/2003 Bass et al.
6,660,338 B1 12/2003 Hargreaves
6,664,112 B2 12/2003 Mulligan et al.
6,670,127 B2 12/2003 Evans
6,670,461 B1 12/2003 Wengel et al.
6,673,552 B2 1/2004 Frey
6,682,702 B2 1/2004 Barth et al.
6,689,319 B1 2/2004 Fisher et al.
6,692,917 B2 2/2004 Neri et al.
6,702,256 B2 3/2004 Killeen et al.
6,706,471 B1 3/2004 Brow et al.
6,706,875 B1 3/2004 Goldberg et al.
6,709,841 B2 3/2004 Short
6,709,852 B1 3/2004 Bloom et al.
6,709,854 B2 3/2004 Donahue et al.
6,713,262 B2 3/2004 Gillibolian et al.
6,716,629 B2 4/2004 Hess et al.
6,716,634 B1 4/2004 Myerson
6,723,509 B2 4/2004 Ach
6,728,129 B2 4/2004 Lindsey et al.
6,743,585 B2 6/2004 Dellinger et al.
6,753,145 B2 6/2004 Holcomb et al.
6,768,005 B2 7/2004 Mellor et al.
6,770,748 B2 8/2004 Imanishi et al.
6,770,892 B2 8/2004 Corson et al.
6,773,676 B2 8/2004 Schembri
6,773,888 B2 8/2004 Li et al.
6,780,982 B2 8/2004 Lyamichev et al.
6,787,308 B2 9/2004 Balasubramanian et al.
6,789,965 B2 9/2004 Barth et al.
6,790,620 B2 9/2004 Bass et al.
6,794,499 B2 9/2004 Wengel et al.
6,796,634 B2 9/2004 Caren et al.
6,800,439 B1 10/2004 McGall et al.
6,814,846 B1 11/2004 Berndt
6,815,218 B1 11/2004 Jacobson et al.
6,824,866 B1 11/2004 Glazer et al.
6,830,890 B2 12/2004 Lockhart et al.
6,833,246 B2 12/2004 Balasubramanian
6,833,450 B1 12/2004 McGall et al.
6,835,938 B2 12/2004 Ghosh et al.
6,838,888 B2 1/2005 Peck
6,841,131 B2 1/2005 Zimmermann et al.
6,845,968 B2 1/2005 Killeen et al.
6,846,454 B2 1/2005 Peck
6,846,922 B1 1/2005 Manoharan et al.
6,852,850 B2 2/2005 Myerson et al.
6,858,720 B2 2/2005 Myerson et al.
6,879,915 B2 4/2005 Cattell
6,880,576 B2 4/2005 Karp et al.
6,884,580 B2 4/2005 Caren et al.
6,887,715 B2 5/2005 Schembri
6,890,723 B2 5/2005 Perbost et al.
6,890,760 B1 5/2005 Webb
6,893,816 B1 5/2005 Beattie
6,897,023 B2 5/2005 Fu et al.
6,900,047 B2 5/2005 Bass
6,900,048 B2 5/2005 Perbost
6,911,611 B2 6/2005 Wong et al.
6,914,229 B2 7/2005 Corson et al.
6,916,113 B2 7/2005 De et al.
6,916,633 B1 7/2005 Shannon
6,919,181 B2 7/2005 Hargreaves
6,927,029 B2 8/2005 Lefkowitz et al.
6,929,951 B2 8/2005 Corson et al.
6,936,472 B2 8/2005 Earhart et al.
6,938,476 B2 9/2005 Chesk
6,939,673 B2 9/2005 Bass et al.
6,943,036 B2 9/2005 Bass
6,946,285 B2 9/2005 Bass
6,950,756 B2 9/2005 Kincaid
6,951,719 B1 10/2005 Dupret et al.
6,958,119 B2 10/2005 Yin et al.
6,960,464 B2 11/2005 Jessee et al.
6,969,449 B2 11/2005 Maher et al.
6,969,488 B2 11/2005 Bridgham et al.
6,976,384 B2 12/2005 Hobbs et al.
6,977,223 B2 12/2005 George et al.
6,987,263 B2 1/2006 Hobbs et al.
6,989,267 B2 1/2006 Kim et al.
6,991,922 B2 1/2006 Dupret et al.
7,008,037 B2 3/2006 Caren et al.
7,025,324 B1 4/2006 Slocum et al.
7,026,124 B2 4/2006 Barth et al.
7,027,930 B2 4/2006 Cattell
7,028,536 B2 4/2006 Karp et al.
7,029,854 B2 4/2006 Collins et al.
7,034,290 B2 4/2006 Lu et al.
7,041,445 B2 5/2006 Chenchik et al.
7,045,289 B2 5/2006 Allawi et al.
7,051,574 B2 5/2006 Peck
7,052,841 B2 5/2006 Delenstarr
7,062,385 B2 6/2006 White et al.
7,064,197 B1 6/2006 Rabbani et al.
7,070,932 B2 7/2006 Leproust et al.
7,075,161 B2 7/2006 Barth
7,078,167 B2 7/2006 Delenstarr et al.
7,078,505 B2 7/2006 Bass et al.
7,094,537 B2 8/2006 Leproust et al.
7,097,974 B1 8/2006 Stahler et al.
7,101,508 B2 9/2006 Thompson et al.
7,101,986 B2 9/2006 Dellinger et al.
7,105,295 B2 9/2006 Bass et al.
7,115,423 B1 10/2006 Mitchell
7,122,303 B2 10/2006 Delenstarr et al.
7,122,364 B1 10/2006 Lyamichev et al.
7,125,488 B2 10/2006 Li
7,125,523 B2 10/2006 Sillman
7,128,876 B2 10/2006 Yin et al.
7,129,075 B2 10/2006 Gerard et al.
7,135,565 B2 11/2006 Dellinger et al.
7,138,062 B2 11/2006 Yin et al.
7,141,368 B2 11/2006 Fisher et al.
7,141,807 B2 11/2006 Joyce et al.
7,147,362 B2 12/2006 Caren et al.
7,150,982 B2 12/2006 Allawi et al.
7,153,689 B2 12/2006 Tolosko et al.
7,163,660 B2 1/2007 Lehmann
7,166,258 B2 1/2007 Bass et al.
7,179,659 B2 2/2007 Stolowitz et al.
7,183,406 B2 2/2007 Belshaw et al.
7,192,710 B2 3/2007 Gellibolian et al.
7,193,077 B2 3/2007 Dellinger et al.
7,195,872 B2 3/2007 Agrawal et al.
7,198,939 B2 4/2007 Dorsel et al.
7,202,264 B2 4/2007 Ravikumar et al.
7,202,358 B2 4/2007 Hargreaves
7,205,128 B2 4/2007 Ilsley et al.
7,205,400 B2 4/2007 Webb
7,206,439 B2 4/2007 Zhou et al.
7,208,322 B2 4/2007 Stolowitz et al.
7,217,522 B2 5/2007 Brenner
7,220,573 B2 5/2007 Shea et al.
7,221,785 B2 5/2007 Curry et al.
7,226,862 B2 6/2007 Staehler et al.
7,227,017 B2 6/2007 Mellor et al.
7,229,497 B2 6/2007 Stott et al.
7,247,337 B1 7/2007 Leproust et al.
7,247,497 B2 7/2007 Dahm et al.
7,252,938 B2 8/2007 Leproust et al.
7,269,518 B2 9/2007 Corson

(56) References Cited

U.S. PATENT DOCUMENTS 7,271,258 B2 9/2007 Dellinger et al.
7,276,336 B1 10/2007 Webb et al.
7,276,378 B2 10/2007 Myerson
7,276,599 B2 10/2007 Moore et al.
7,282,183 B2 10/2007 Peck
7,282,332 B2 10/2007 Caren et al.
7,282,705 B2 10/2007 Brennen
7,291,471 B2 11/2007 Sampson et al.
7,302,348 B2 11/2007 Ghosh et al.
7,306,917 B2 12/2007 Prudent et al.
7,314,599 B2 1/2008 Roitman et al.
7,323,320 B2 1/2008 Oleinikov
7,344,831 B2 3/2008 Wolber et al.
7,348,144 B2 3/2008 Minor
7,351,379 B2 4/2008 Schleifer
7,353,116 B2 4/2008 Webb et al.
7,361,906 B2 4/2008 Ghosh et al.
7,364,896 B2 4/2008 Schembri
7,368,550 B2 5/2008 Dellinger et al.
7,371,348 B2 5/2008 Schleifer et al.
7,371,519 B2 5/2008 Wolber et al.
7,371,580 B2 5/2008 Yakhini et al.
7,372,982 B2 5/2008 Le
7,384,746 B2 6/2008 Lyamichev et al.
7,385,050 B2 6/2008 Dellinger et al.
7,390,457 B2 6/2008 Schembri
7,393,665 B2 7/2008 Brenner
7,396,676 B2 7/2008 Robotti et al.
7,399,844 B2 7/2008 Sampson et al.
7,402,279 B2 7/2008 Schembri
7,411,061 B2 8/2008 Myerson et al.
7,413,709 B2 8/2008 Roitman et al.
7,417,139 B2 8/2008 Dellinger et al.
7,422,911 B2 9/2008 Schembri
7,427,679 B2 9/2008 Dellinger et al.
7,432,048 B2 10/2008 Neri et al.
7,435,810 B2 10/2008 Myerson et al.
7,439,272 B2 10/2008 Xu
7,476,709 B2 1/2009 Moody et al.
7,482,118 B2 1/2009 Allawi et al.
7,488,607 B2 2/2009 Tom-Moy et al.
7,504,213 B2 3/2009 Sana et al.
7,514,369 B2 4/2009 Li et al.
7,517,979 B2 4/2009 Wolber
7,524,942 B2 4/2009 Wang et al.
7,524,950 B2 4/2009 Dellinger et al.
7,527,928 B2 5/2009 Neri et al.
7,531,303 B2 5/2009 Dorsel et al.
7,534,561 B2 5/2009 Sana et al.
7,534,563 B2 5/2009 Hargreaves
7,537,936 B2 5/2009 Dahm et al.
7,541,145 B2 6/2009 Prudent et al.
7,544,473 B2 6/2009 Brenner
7,556,919 B2 7/2009 Chenchik et al.
7,563,600 B2 7/2009 Oleinikov
7,572,585 B2 8/2009 Wang
7,572,907 B2 8/2009 Dellinger et al.
7,572,908 B2 8/2009 Dellinger et al.
7,585,970 B2 9/2009 Dellinger et al.
7,588,889 B2 9/2009 Wolber et al.
7,595,350 B2 9/2009 Xu
7,604,941 B2 10/2009 Jacobson
7,604,996 B1 10/2009 Stuelpnagel et al.
7,608,396 B2 10/2009 Delenstarr
7,618,777 B2 11/2009 Myerson et al.
7,629,120 B2 12/2009 Bennett et al.
7,635,772 B2 12/2009 McCormac
7,648,832 B2 1/2010 Jessee et al.
7,651,762 B2 1/2010 Xu et al.
7,659,069 B2 2/2010 Belyaev et al.
7,678,542 B2 3/2010 Lyamichev et al.
7,682,809 B2 3/2010 Sampson
7,709,197 B2 5/2010 Drmanac
7,718,365 B2 5/2010 Wang
7,718,786 B2 5/2010 Dupret et al.
7,723,077 B2 5/2010 Young et al.
7,737,088 B1 6/2010 Stahler et al.
7,737,089 B2 6/2010 Guimil et al.
7,741,463 B2 6/2010 Gormley et al.
7,749,701 B2 7/2010 Leproust et al.
7,759,471 B2 7/2010 Dellinger et al.
7,776,021 B2 8/2010 Borenstein et al.
7,776,532 B2 8/2010 Gibson et al.
7,790,369 B2 9/2010 Stahler et al.
7,790,387 B2 9/2010 Dellinger et al.
7,807,356 B2 10/2010 Sampson et al.
7,807,806 B2 10/2010 Allawi et al.
7,811,753 B2 10/2010 Eshoo
7,816,079 B2 10/2010 Fischer
7,820,387 B2 10/2010 Neri et al.
7,829,314 B2 11/2010 Prudent et al.
7,855,281 B2 12/2010 Dellinger et al.
7,862,999 B2 1/2011 Zheng et al.
7,867,782 B2 1/2011 Barth
7,875,463 B2 1/2011 Adaskin et al.
7,879,541 B2 2/2011 Kincaid
7,879,580 B2 2/2011 Carr et al.
7,894,998 B2 2/2011 Kincaid
7,919,239 B2 4/2011 Wang
7,919,308 B2 4/2011 Schleifer
7,927,797 B2 4/2011 Nobile et al.
7,927,838 B2 4/2011 Shannon
7,932,025 B2 4/2011 Carr et al.
7,932,070 B2 4/2011 Hogrefe et al.
7,935,800 B2 5/2011 Allawi et al.
7,939,645 B2 5/2011 Borns
7,943,046 B2 5/2011 Martosella et al.
7,943,358 B2 5/2011 Hogrefe et al.
7,960,157 B2 6/2011 Borns
7,977,119 B2 7/2011 Kronick et al.
7,979,215 B2 7/2011 Sampas
7,998,437 B2 8/2011 Berndt et al.
7,999,087 B2 8/2011 Dellinger et al.
8,021,842 B2 9/2011 Brenner
8,021,844 B2 9/2011 Wang
8,034,917 B2 10/2011 Yamada
8,036,835 B2 10/2011 Sampas et al.
8,048,664 B2 11/2011 Guan et al.
8,053,191 B2 11/2011 Blake
8,058,001 B2 11/2011 Crameri et al.
8,058,004 B2 11/2011 Oleinikov
8,058,055 B2 11/2011 Barrett et al.
8,063,184 B2 11/2011 Allawi et al.
8,067,556 B2 11/2011 Hogrefe et al.
8,073,626 B2 12/2011 Troup et al.
8,076,064 B2 12/2011 Wang
8,076,152 B2 12/2011 Robotti
8,097,711 B2 1/2012 Timar et al.
8,137,936 B2 3/2012 Macevicz
8,148,068 B2 4/2012 Brenner
8,154,729 B2 4/2012 Baldo et al.
8,168,385 B2 5/2012 Brenner
8,168,388 B2 5/2012 Gormley et al.
8,173,368 B2 5/2012 Staehler et al.
8,182,991 B1 5/2012 Kaiser et al.
8,194,244 B2 6/2012 Wang et al.
8,198,071 B2 6/2012 Goshoo et al.
8,202,983 B2 6/2012 Dellinger et al.
8,202,985 B2 6/2012 Dellinger et al.
8,206,952 B2 6/2012 Carr et al.
8,213,015 B2 7/2012 Kraiczek et al.
8,242,258 B2 8/2012 Dellinger et al.
8,247,221 B2 8/2012 Fawcett et al.
8,263,335 B2 9/2012 Carr et al.
8,268,605 B2 9/2012 Sorge et al.
8,283,148 B2 10/2012 Sorge et al.
8,288,093 B2 10/2012 Hall et al.
8,298,767 B2 10/2012 Brenner et al.
8,304,273 B2 11/2012 Stellacci et al.
8,309,307 B2 11/2012 Barrett et al.
8,309,706 B2 11/2012 Dellinger et al.
8,309,710 B2 11/2012 Sierzchala et al.
8,314,220 B2 11/2012 Mullinax et al.
8,318,433 B2 11/2012 Brenner

(56) References Cited

U.S. PATENT DOCUMENTS 8,318,479 B2 11/2012 Domansky et al.
8,357,489 B2 1/2013 Chua et al.
8,357,490 B2 1/2013 Froehlich et al.
8,367,016 B2 2/2013 Quan et al.
8,367,335 B2 2/2013 Staehler et al.
8,380,441 B2 2/2013 Webb et al.
8,383,338 B2 2/2013 Kitzman et al.
8,415,138 B2 4/2013 Leproust
8,435,736 B2 5/2013 Gibson et al.
8,445,205 B2 5/2013 Brenner
8,445,206 B2 5/2013 Bergmann et al.
8,470,996 B2 6/2013 Brenner
8,476,018 B2 7/2013 Brenner
8,476,598 B1 7/2013 Pralle et al.
8,481,292 B2 7/2013 Casbon et al.
8,481,309 B2 7/2013 Zhang et al.
8,491,561 B2 7/2013 Borenstein et al.
8,497,069 B2 7/2013 Hutchison et al.
8,500,979 B2 8/2013 Elibol et al.
8,501,454 B2 8/2013 Liu et al.
8,507,226 B2 8/2013 Carr et al.
8,507,239 B2 8/2013 Lubys et al.
8,507,272 B2 8/2013 Zhang et al.
8,530,197 B2 9/2013 Li et al.
8,552,174 B2 10/2013 Dellinger et al.
8,563,478 B2 10/2013 Gormley et al.
8,569,046 B2 10/2013 Love et al.
8,577,621 B2 11/2013 Troup et al.
8,586,310 B2 11/2013 Mitra et al.
8,614,092 B2 12/2013 Zhang et al.
8,642,755 B2 2/2014 Sierzchala et al.
8,664,164 B2 3/2014 Ericsson et al.
8,669,053 B2 3/2014 Stuelpnagel et al.
8,679,756 B1 3/2014 Brenner et al.
8,685,642 B2 4/2014 Sampas
8,685,676 B2 4/2014 Hogrefe et al.
8,685,678 B2 4/2014 Casbon et al.
8,715,933 B2 5/2014 Oliver
8,715,967 B2 5/2014 Casbon et al.
8,716,467 B2 5/2014 Jacobson
8,722,368 B2 5/2014 Casbon et al.
8,722,585 B2 5/2014 Wang
8,728,766 B2 5/2014 Casbon et al.
8,741,606 B2 6/2014 Casbon et al.
8,808,896 B2 8/2014 Choo et al.
8,808,986 B2 8/2014 Jacobson et al.
8,815,600 B2 8/2014 Liu et al.
8,889,851 B2 11/2014 Leproust et al.
8,932,994 B2 1/2015 Gormley et al.
8,962,532 B2 2/2015 Shapiro et al.
8,968,999 B2 3/2015 Gibson et al.
8,980,563 B2 3/2015 Zheng et al.
9,018,365 B2 4/2015 Brenner
9,023,601 B2 5/2015 Oleinikov
9,051,666 B2 6/2015 Oleinikov
9,073,962 B2 7/2015 Fracchia et al.
9,074,204 B2 7/2015 Anderson et al.
9,085,797 B2 7/2015 Gebeyehu et al.
9,133,510 B2 9/2015 Andersen et al.
9,139,874 B2 9/2015 Myers et al.
9,150,853 B2 10/2015 Hudson et al.
9,187,777 B2 11/2015 Jacobson et al.
9,194,001 B2 11/2015 Brenner
9,216,414 B2 12/2015 Chu
9,217,144 B2 12/2015 Jacobson et al.
9,279,149 B2 3/2016 Efcavitch et al.
9,286,439 B2 3/2016 Shapiro et al.
9,295,965 B2 3/2016 Jacobson et al.
9,315,861 B2 4/2016 Hendricks et al.
9,328,378 B2 5/2016 Earnshaw et al.
9,347,091 B2 5/2016 Bergmann et al.
9,375,748 B2 6/2016 Harumoto et al.
9,376,677 B2 6/2016 Mir
9,376,678 B2 6/2016 Gormley et al.
9,384,320 B2 7/2016 Church
9,384,920 B1 7/2016 Bakulich
9,388,407 B2 7/2016 Jacobson
9,394,333 B2 7/2016 Wada et al.
9,403,141 B2 8/2016 Banyai et al.
9,409,139 B2 8/2016 Banyai et al.
9,410,149 B2 8/2016 Brenner et al.
9,410,173 B2 8/2016 Betts et al.
9,416,411 B2 8/2016 Stuelpnagel et al.
9,422,600 B2 8/2016 Ramu et al.
9,487,824 B2 11/2016 Kutyavin
9,499,848 B2 11/2016 Carr et al.
9,523,122 B2 12/2016 Zheng et al.
9,528,148 B2 12/2016 Zheng et al.
9,534,251 B2 1/2017 Young et al.
9,555,388 B2 1/2017 Banyai et al.
9,568,839 B2 2/2017 Stahler et al.
9,580,746 B2 2/2017 Leproust et al.
9,670,529 B2 6/2017 Osborne et al.
9,670,536 B2 6/2017 Casbon et al.
9,677,067 B2 6/2017 Toro et al.
9,695,211 B2 7/2017 Wada et al.
9,718,060 B2 8/2017 Venter et al.
9,745,573 B2 8/2017 Stuelpnagel et al.
9,745,619 B2 8/2017 Rabbani et al.
9,765,387 B2 9/2017 Rabbani et al.
9,771,576 B2 9/2017 Gibson et al.
9,833,761 B2 12/2017 Banyai et al.
9,834,774 B2 12/2017 Carstens
9,839,894 B2 12/2017 Banyai et al.
9,879,283 B2 1/2018 Ravinder et al.
9,889,423 B2 2/2018 Banyai et al.
9,895,673 B2 2/2018 Peck et al.
9,925,510 B2 3/2018 Jacobson et al.
9,932,576 B2 4/2018 Raymond et al.
9,981,239 B2 5/2018 Banyai et al.
10,053,688 B2 8/2018 Cox
10,272,410 B2 4/2019 Banyai et al.
10,384,188 B2 8/2019 Banyai et al.
10,384,189 B2 8/2019 Peck
10,417,457 B2 9/2019 Peck
10,583,415 B2 3/2020 Banyai et al.
10,632,445 B2 4/2020 Banyai et al.
10,639,609 B2 5/2020 Banyai et al.
10,669,304 B2 6/2020 Indermuhle et al.
10,969,965 B2 4/2021 Malina et al.
2001/0018512 A1 8/2001 Blanchard
2001/0039014 A1 11/2001 Bass et al.
2001/0055761 A1 12/2001 Kanemoto et al.
2002/0012930 A1 1/2002 Rothberg et al.
2002/0025561 A1 2/2002 Hodgson
2002/0076716 A1 6/2002 Sabanayagam et al.
2002/0081582 A1 6/2002 Gao et al.
2002/0094533 A1 7/2002 Hess et al.
2002/0095073 A1 7/2002 Jacobs et al.
2002/0119459 A1 8/2002 Griffiths
2002/0132308 A1 9/2002 Liu et al.
2002/0155439 A1 10/2002 Rodriguez et al.
2002/0160536 A1 10/2002 Regnier et al.
2002/0164824 A1 11/2002 Xiao et al.
2003/0008411 A1 1/2003 Van et al.
2003/0022207 A1 1/2003 Balasubramanian et al.
2003/0022240 A1 1/2003 Luo et al.
2003/0022317 A1 1/2003 Jack et al.
2003/0044781 A1 3/2003 Korlach et al.
2003/0058629 A1 3/2003 Hirai et al.
2003/0064398 A1 4/2003 Barnes
2003/0068633 A1 4/2003 Belshaw et al.
2003/0082719 A1 5/2003 Schumacher et al.
2003/0100102 A1 5/2003 Rothberg et al.
2003/0108903 A1 6/2003 Wang et al.
2003/0120035 A1 6/2003 Gao et al.
2003/0130827 A1 7/2003 Bentzien et al.
2003/0138782 A1 7/2003 Evans
2003/0143605 A1 7/2003 Lok et al.
2003/0148291 A1 8/2003 Robotti
2003/0148344 A1 8/2003 Rothberg et al.
2003/0171325 A1 9/2003 Gascoyne et al.
2003/0186226 A1 10/2003 Brennan et al.
2003/0228602 A1 12/2003 Parker et al.

(56) References Cited

U.S. PATENT DOCUMENTS

2003/0228620 A1 12/2003 Du
2004/0009498 A1 1/2004 Short
2004/0043509 A1 3/2004 Stahler et al.
2004/0053362 A1 3/2004 De et al.
2004/0086892 A1 5/2004 Crothers et al.
2004/0087008 A1 5/2004 Schembri
2004/0106130 A1 6/2004 Besemer et al.
2004/0106728 A1 6/2004 McGall et al.
2004/0110133 A1 6/2004 Xu et al.
2004/0175710 A1 9/2004 Haushalter
2004/0175734 A1 9/2004 Stahler et al.
2004/0191810 A1 9/2004 Yamamoto
2004/0213795 A1 10/2004 Collins et al.
2004/0219663 A1 11/2004 Page et al.
2004/0236027 A1 11/2004 Maeji et al.
2004/0248161 A1 12/2004 Rothberg et al.
2004/0253242 A1 12/2004 Bowdish et al.
2004/0259146 A1 12/2004 Friend et al.
2005/0022895 A1 2/2005 Barth et al.
2005/0049402 A1 3/2005 Babcook et al.
2005/0049796 A1 3/2005 Webb et al.
2005/0053968 A1 3/2005 Bharadwaj et al.
2005/0079510 A1 4/2005 Berka et al.
2005/0100932 A1 5/2005 Lapidus et al.
2005/0112608 A1 5/2005 Grossman et al.
2005/0112636 A1 5/2005 Hurt et al.
2005/0112679 A1 5/2005 Myerson et al.
2005/0124022 A1 6/2005 Srinivasan et al.
2005/0137805 A1 6/2005 Lewin et al.
2005/0208513 A1 9/2005 Agbo et al.
2005/0214778 A1 9/2005 Peck et al.
2005/0214779 A1 9/2005 Peck et al.
2005/0227235 A1 10/2005 Carr et al.
2005/0255477 A1 11/2005 Carr et al.
2005/0266045 A1 12/2005 Canham et al.
2005/0277125 A1 12/2005 Benn et al.
2005/0282158 A1 12/2005 Landegren
2005/0287585 A1 12/2005 Oleinikov
2006/0003381 A1 1/2006 Gilmore et al.
2006/0003958 A1 1/2006 Melville et al.
2006/0012784 A1 1/2006 Ulmer
2006/0012793 A1 1/2006 Harris
2006/0019084 A1 1/2006 Pearson
2006/0024678 A1 2/2006 Buzby
2006/0024711 A1 2/2006 Lapidus et al.
2006/0024721 A1 2/2006 Pedersen
2006/0076482 A1 4/2006 Hobbs et al.
2006/0078909 A1 4/2006 Srinivasan et al.
2006/0078927 A1 4/2006 Peck et al.
2006/0078937 A1 4/2006 Korlach et al.
2006/0127920 A1 6/2006 Church et al.
2006/0134638 A1 6/2006 Mulligan et al.
2006/0160138 A1 7/2006 Church
2006/0171855 A1 8/2006 Yin et al.
2006/0202330 A1 9/2006 Reinhardt et al.
2006/0203236 A1 9/2006 Ji et al.
2006/0203237 A1 9/2006 Ji et al.
2006/0207923 A1 9/2006 Li
2006/0219637 A1 10/2006 Killeen et al.
2007/0031857 A1 2/2007 Makarov et al.
2007/0031877 A1 2/2007 Stahler et al.
2007/0043516 A1 2/2007 Gustafsson et al.
2007/0054127 A1 3/2007 Hergenrother et al.
2007/0059692 A1 3/2007 Gao et al.
2007/0087349 A1 4/2007 Staehler et al.
2007/0099196 A1 5/2007 Kauppinen et al.
2007/0099208 A1 5/2007 Drmanac et al.
2007/0122817 A1 5/2007 Church et al.
2007/0128635 A1 6/2007 Macevicz
2007/0141557 A1 6/2007 Raab et al.
2007/0196834 A1 8/2007 Cerrina et al.
2007/0196854 A1 8/2007 Stahler et al.
2007/0207482 A1 9/2007 Church et al.
2007/0207487 A1 9/2007 Emig et al.
2007/0231800 A1 10/2007 Roberts et al.
2007/0238104 A1 10/2007 Barrett et al.
2007/0238106 A1 10/2007 Barrett et al.
2007/0238108 A1 10/2007 Barrett et al.
2007/0259344 A1 11/2007 Leproust et al.
2007/0259345 A1 11/2007 Sampas
2007/0259346 A1 11/2007 Gordon et al.
2007/0259347 A1 11/2007 Gordon et al.
2007/0269870 A1 11/2007 Church et al.
2008/0085511 A1 4/2008 Peck et al.
2008/0085514 A1 4/2008 Peck et al.
2008/0087545 A1 4/2008 Jensen et al.
2008/0161200 A1 7/2008 Yu et al.
2008/0182296 A1 7/2008 Chanda et al.
2008/0214412 A1 9/2008 Stahler et al.
2008/0227160 A1 9/2008 Kool
2008/0233616 A1 9/2008 Liss
2008/0287320 A1 11/2008 Baynes et al.
2008/0300842 A1 12/2008 Govindarajan et al.
2008/0308884 A1 12/2008 Kalvesten
2008/0311628 A1 12/2008 Shoemaker
2009/0036664 A1 2/2009 Peter
2009/0053704 A1 2/2009 Novoradovskaya et al.
2009/0062129 A1 3/2009 McKernan et al.
2009/0074771 A1 3/2009 Koenig et al.
2009/0087840 A1 4/2009 Baynes et al.
2009/0088679 A1 4/2009 Wood et al.
2009/0105094 A1 4/2009 Heiner et al.
2009/0170802 A1 7/2009 Stahler et al.
2009/0176280 A1 7/2009 Hutchison, III et al.
2009/0181861 A1 7/2009 Li et al.
2009/0194483 A1 8/2009 Robotti et al.
2009/0230044 A1 9/2009 Bek
2009/0238722 A1 9/2009 Mora-Fillat et al.
2009/0239759 A1 9/2009 Balch
2009/0246788 A1 10/2009 Albert et al.
2009/0263802 A1 10/2009 Drmanac
2009/0285825 A1 11/2009 Kini et al.
2009/0324546 A1 12/2009 Notka et al.
2010/0004143 A1 1/2010 Shibahara
2010/0008851 A1 1/2010 Nicolaides et al.
2010/0009872 A1 1/2010 Eid et al.
2010/0047805 A1 2/2010 Wang
2010/0051967 A1 3/2010 Bradley et al.
2010/0069250 A1 3/2010 White, III et al.
2010/0090341 A1 4/2010 Wan et al.
2010/0099103 A1 4/2010 Hsieh et al.
2010/0111768 A1 5/2010 Banerjee et al.
2010/0160463 A1 6/2010 Wang et al.
2010/0167950 A1 7/2010 Juang et al.
2010/0173364 A1 7/2010 Evans et al.
2010/0216648 A1 8/2010 Staehler et al.
2010/0256017 A1 10/2010 Larman et al.
2010/0258487 A1 10/2010 Zelechonok et al.
2010/0272711 A1 10/2010 Feldman et al.
2010/0286290 A1 11/2010 Lohmann et al.
2010/0292102 A1 11/2010 Nouri
2010/0300882 A1 12/2010 Zhang et al.
2010/0323404 A1 12/2010 Lathrop
2011/0009607 A1 1/2011 Komiyama et al.
2011/0082055 A1 4/2011 Fox et al.
2011/0114244 A1 5/2011 Yoo et al.
2011/0114549 A1 5/2011 Yin et al.
2011/0124049 A1 5/2011 Li et al.
2011/0124055 A1 5/2011 Carr et al.
2011/0126929 A1 6/2011 Velasquez-Garcia et al.
2011/0171651 A1 7/2011 Richmond
2011/0172127 A1 7/2011 Jacobson et al.
2011/0201057 A1 8/2011 Carr et al.
2011/0217738 A1 9/2011 Jacobson
2011/0230653 A1 9/2011 Novoradovskaya et al.
2011/0254107 A1 10/2011 Bulovic et al.
2011/0287435 A1 11/2011 Grunenwald et al.
2012/0003713 A1 1/2012 Hansen et al.
2012/0021932 A1 1/2012 Mershin et al.
2012/0027786 A1 2/2012 Gupta et al.
2012/0028843 A1 2/2012 Ramu et al.
2012/0032366 A1 2/2012 Ivniski et al.
2012/0046175 A1 2/2012 Rodesch et al.
2012/0050411 A1 3/2012 Mabritto et al.

(56) References Cited

U.S. PATENT DOCUMENTS

2012/0094847 A1 4/2012 Warthmann et al.
2012/0128548 A1 5/2012 West et al.
2012/0129704 A1 5/2012 Gunderson et al.
2012/0149602 A1 6/2012 Friend et al.
2012/0164127 A1 6/2012 Short et al.
2012/0164633 A1 6/2012 Laffler
2012/0164691 A1 6/2012 Eshoo et al.
2012/0184724 A1 7/2012 Sierzchala et al.
2012/0220497 A1 8/2012 Jacobson et al.
2012/0231968 A1 9/2012 Bruhn et al.
2012/0238737 A1 9/2012 Dellinger et al.
2012/0258487 A1 10/2012 Chang et al.
2012/0264653 A1 10/2012 Carr et al.
2012/0270750 A1 10/2012 Oleinikov
2012/0270754 A1 10/2012 Blake
2012/0283140 A1 11/2012 Chu
2012/0288476 A1 11/2012 Hartmann et al.
2012/0289691 A1 11/2012 Dellinger et al.
2012/0315670 A1 12/2012 Jacobson et al.
2012/0322681 A1 12/2012 Kung et al.
2013/0005585 A1 1/2013 Anderson et al.
2013/0005612 A1 1/2013 Carr et al.
2013/0017642 A1 1/2013 Milgrew et al.
2013/0017977 A1 1/2013 Oleinikov
2013/0017978 A1 1/2013 Kavanagh et al.
2013/0035261 A1 2/2013 Sierzchala et al.
2013/0040836 A1 2/2013 Himmler et al.
2013/0045483 A1 2/2013 Treusch et al.
2013/0053252 A1 2/2013 Xie et al.
2013/0059296 A1 3/2013 Jacobson et al.
2013/0059761 A1 3/2013 Jacobson et al.
2013/0065017 A1 3/2013 Sieber
2013/0109595 A1 5/2013 Routenberg
2013/0109596 A1 5/2013 Peterson et al.
2013/0123129 A1 5/2013 Zeiner et al.
2013/0130321 A1 5/2013 Staehler et al.
2013/0137161 A1 5/2013 Zhang et al.
2013/0137173 A1 5/2013 Zhang et al.
2013/0137174 A1 5/2013 Zhang et al.
2013/0137861 A1 5/2013 Leproust et al.
2013/0164308 A1 6/2013 Foletti et al.
2013/0165328 A1 6/2013 Previte et al.
2013/0196864 A1 8/2013 Govindarajan et al.
2013/0225421 A1 8/2013 Li et al.
2013/0244884 A1 9/2013 Jacobson et al.
2013/0252849 A1 9/2013 Hudson et al.
2013/0261027 A1 10/2013 Li et al.
2013/0281308 A1 10/2013 Kung et al.
2013/0289246 A1 10/2013 Crowe et al.
2013/0296192 A1 11/2013 Jacobson et al.
2013/0296194 A1 11/2013 Jacobson et al.
2013/0298265 A1 11/2013 Cunnac et al.
2013/0309725 A1 11/2013 Jacobson et al.
2013/0323725 A1 12/2013 Peter et al.
2013/0330778 A1 12/2013 Zeiner et al.
2014/0011226 A1 1/2014 Bernick et al.
2014/0018441 A1 1/2014 Fracchia et al.
2014/0031240 A1 1/2014 Behlke et al.
2014/0038240 A1 2/2014 Temme et al.
2014/0106394 A1 4/2014 Ko et al.
2014/0141982 A1 5/2014 Jacobson et al.
2014/0170665 A1 6/2014 Hiddessen et al.
2014/0178992 A1 6/2014 Nakashima et al.
2014/0221250 A1 8/2014 Vasquez et al.
2014/0274729 A1 9/2014 Kurn et al.
2014/0274741 A1 9/2014 Hunter et al.
2014/0303000 A1 10/2014 Armour et al.
2014/0309119 A1 10/2014 Jacobson et al.
2014/0309142 A1 10/2014 Tian
2015/0010953 A1 1/2015 Lindstrom et al.
2015/0012723 A1 1/2015 Park et al.
2015/0031089 A1 1/2015 Lindstrom
2015/0038373 A1 2/2015 Banyai et al.
2015/0056609 A1 2/2015 Daum et al.
2015/0057625 A1 2/2015 Coulthard
2015/0065357 A1 3/2015 Fox
2015/0065393 A1 3/2015 Jacobson
2015/0099870 A1 4/2015 Bennett et al.
2015/0119293 A1 4/2015 Short
2015/0120265 A1 4/2015 Amirav-Drory et al.
2015/0159152 A1 6/2015 Allen et al.
2015/0183853 A1 7/2015 Sharma et al.
2015/0191524 A1 7/2015 Smith et al.
2015/0191719 A1 7/2015 Hudson et al.
2015/0196917 A1 7/2015 Kay et al.
2015/0203839 A1 7/2015 Jacobson et al.
2015/0211047 A1 7/2015 Borns
2015/0225782 A1 8/2015 Walder et al.
2015/0240232 A1 8/2015 Zamore et al.
2015/0240280 A1 8/2015 Gibson et al.
2015/0261664 A1 9/2015 Goldman et al.
2015/0269313 A1 9/2015 Church
2015/0293102 A1 10/2015 Shim
2015/0307875 A1 10/2015 Happe et al.
2015/0321191 A1 11/2015 Kendall et al.
2015/0322504 A1 11/2015 Lao et al.
2015/0344927 A1 12/2015 Sampson et al.
2015/0353921 A9 12/2015 Tian
2015/0353994 A1 12/2015 Myers et al.
2015/0361420 A1 12/2015 Hudson et al.
2015/0361422 A1 12/2015 Sampson et al.
2015/0361423 A1 12/2015 Sampson et al.
2015/0368687 A1 12/2015 Saaem et al.
2015/0376602 A1 12/2015 Jacobson et al.
2016/0001247 A1 1/2016 Oleinikov
2016/0002621 A1 1/2016 Nelson et al.
2016/0002622 A1 1/2016 Nelson et al.
2016/0010045 A1 1/2016 Cohen et al.
2016/0017394 A1 1/2016 Liang et al.
2016/0017425 A1 1/2016 Ruvolo et al.
2016/0019341 A1 1/2016 Harris et al.
2016/0024138 A1 1/2016 Gebeyehu et al.
2016/0024576 A1 1/2016 Chee
2016/0026753 A1 1/2016 Krishnaswami et al.
2016/0026758 A1 1/2016 Jabara et al.
2016/0032396 A1 2/2016 Diehn et al.
2016/0046973 A1 2/2016 Efcavitch et al.
2016/0046974 A1 2/2016 Efcavitch et al.
2016/0082472 A1 3/2016 Perego et al.
2016/0089651 A1 3/2016 Banyai
2016/0090422 A1 3/2016 Reif et al.
2016/0090592 A1 3/2016 Banyai et al.
2016/0096160 A1 4/2016 Banyai et al.
2016/0097051 A1 4/2016 Jacobson et al.
2016/0102322 A1 4/2016 Ravinder et al.
2016/0108466 A1 4/2016 Nazarenko et al.
2016/0122755 A1 5/2016 Hall et al.
2016/0122800 A1 5/2016 Bernick et al.
2016/0152972 A1 6/2016 Stapleton et al.
2016/0168611 A1 6/2016 Efcavitch et al.
2016/0184788 A1 6/2016 Hall et al.
2016/0200759 A1 7/2016 Srivastava et al.
2016/0215283 A1 7/2016 Braman et al.
2016/0229884 A1 8/2016 Indermuhle et al.
2016/0230175 A1 8/2016 Carstens
2016/0230221 A1 8/2016 Bergmann et al.
2016/0251651 A1 9/2016 Banyai et al.
2016/0256846 A1 9/2016 Smith et al.
2016/0264958 A1 9/2016 Toro et al.
2016/0289758 A1 10/2016 Akeson et al.
2016/0289839 A1 10/2016 Harumoto et al.
2016/0303535 A1 10/2016 Banyai et al.
2016/0304862 A1 10/2016 Igawa et al.
2016/0304946 A1 10/2016 Betts et al.
2016/0310426 A1 10/2016 Wu
2016/0310927 A1 10/2016 Banyai et al.
2016/0318016 A1 11/2016 Hou et al.
2016/0333340 A1 11/2016 Wu
2016/0339409 A1 11/2016 Banyai et al.
2016/0340672 A1 11/2016 Banyai et al.
2016/0348098 A1 12/2016 Stuelpnagel et al.
2016/0354752 A1 12/2016 Banyai et al.
2016/0355880 A1 12/2016 Gormley et al.
2017/0017436 A1 1/2017 Church

(56) References Cited

U.S. PATENT DOCUMENTS

2017/0066844 A1 3/2017 Glanville
2017/0067099 A1 3/2017 Zheng et al.
2017/0073664 A1 3/2017 McCafferty et al.
2017/0073731 A1 3/2017 Zheng et al.
2017/0081660 A1 3/2017 Cox et al.
2017/0081716 A1 3/2017 Peck
2017/0088887 A1 3/2017 Makarov et al.
2017/0095785 A1 4/2017 Banyai et al.
2017/0096706 A1 4/2017 Behlke et al.
2017/0114404 A1 4/2017 Behlke et al.
2017/0141793 A1 5/2017 Strauss et al.
2017/0147748 A1 5/2017 Staehler et al.
2017/0151546 A1 6/2017 Peck et al.
2017/0159044 A1 6/2017 Toro et al.
2017/0175110 A1 6/2017 Jacobson et al.
2017/0218537 A1 8/2017 Olivares
2017/0233764 A1 8/2017 Young et al.
2017/0247473 A1 8/2017 Short
2017/0249345 A1 8/2017 Malik et al.
2017/0253644 A1 9/2017 Steyaert et al.
2017/0298432 A1 10/2017 Holt
2017/0320061 A1 11/2017 Venter et al.
2017/0327819 A1 11/2017 Banyai et al.
2017/0355984 A1 12/2017 Evans et al.
2017/0357752 A1 12/2017 Diggans
2017/0362589 A1 12/2017 Banyai et al.
2018/0029001 A1 2/2018 Banyai et al.
2018/0051278 A1 2/2018 Cox et al.
2018/0051280 A1 2/2018 Gibson et al.
2018/0068060 A1 3/2018 Ceze et al.
2018/0104664 A1 4/2018 Fernandez
2018/0126355 A1 5/2018 Peck et al.
2018/0142289 A1 5/2018 Zeitoun et al.
2018/0171509 A1 6/2018 Cox
2018/0236425 A1 8/2018 Banyai et al.
2018/0253563 A1 9/2018 Peck et al.
2018/0264428 A1 9/2018 Banyai et al.
2018/0273936 A1 9/2018 Cox et al.
2018/0282721 A1 10/2018 Cox et al.
2018/0291445 A1 10/2018 Betts et al.
2018/0312834 A1 11/2018 Cox et al.
2018/0326388 A1 11/2018 Banyai et al.
2018/0334712 A1 11/2018 Singer et al.
2018/0346585 A1 12/2018 Zhang et al.
2018/0355351 A1 12/2018 Nugent et al.
2019/0060345 A1 2/2019 Harrison et al.
2019/0083596 A1 3/2019 Orentas et al.
2019/0118154 A1 4/2019 Marsh et al.
2019/0135926 A1 5/2019 Glanville
2019/0224711 A1 7/2019 Demeris, Jr.
2019/0240636 A1 8/2019 Peck et al.
2019/0244109 A1 8/2019 Bramlett et al.
2019/0314783 A1 10/2019 Banyai et al.
2019/0318132 A1 10/2019 Peck
2019/0352635 A1 11/2019 Toro et al.
2019/0366293 A1 12/2019 Banyai et al.
2019/0366294 A1 12/2019 Banyai et al.
2020/0017907 A1 1/2020 Zeitoun et al.
2020/0102611 A1 4/2020 Zeitoun et al.
2020/0156037 A1 5/2020 Banyai et al.
2020/0181667 A1 6/2020 Cheng-Hsien et al.
2020/0222875 A1 7/2020 Peck et al.
2020/0283760 A1 9/2020 Nugent et al.
2020/0299322 A1 9/2020 Indermuhle et al.
2020/0299684 A1 9/2020 Toro et al.
2020/0308575 A1 10/2020 Sato
2020/0325235 A1 10/2020 Tabibiazar et al.
2020/0342143 A1 10/2020 Peck
2021/0002710 A1 1/2021 Gantt et al.
2021/0040476 A1 2/2021 Cox et al.
2021/0102192 A1 4/2021 Tabibiazar et al.
2021/0102195 A1 4/2021 Sato et al.
2021/0102198 A1 4/2021 Cox et al.
2021/0115594 A1 4/2021 Cox et al.
2021/0129108 A1 5/2021 Marsh et al.
2021/0142182 A1 5/2021 Bramlett et al.
2021/0147830 A1* 5/2021 Liss ........................ C12P 19/34
2021/0170356 A1 6/2021 Peck et al.
2021/0179724 A1 6/2021 Sato et al.
2021/0207197 A1 7/2021 Gantt et al.
2021/0332078 A1 10/2021 Wu
2021/0348220 A1 11/2021 Zeitoun et al.
2021/0355194 A1 11/2021 Sato et al.

FOREIGN PATENT DOCUMENTS

CN 1771336 A 5/2006
CN 101277758 A 10/2008
CN 102159726 A 8/2011
CN 103907117 A 7/2014
CN 104520864 A 4/2015
CN 104562213 A 4/2015
CN 104734848 A 6/2015
CN 105637097 A 6/2016
DE 10260805 A1 7/2004
EP 0090789 A1 10/1983
EP 0126621 B1 8/1990
EP 0753057 A1 1/1997
EP 1314783 A1 5/2003
EP 1363125 A2 11/2003
EP 1546387 A2 6/2005
EP 1153127 B1 7/2006
EP 1728860 A1 12/2006
EP 1072010 B1 4/2010
EP 2175021 A2 4/2010
EP 2330216 A1 6/2011
EP 1343802 B1 5/2012
EP 2504449 A1 10/2012
EP 2751729 A1 7/2014
EP 2872629 A1 5/2015
EP 2928500 A1 10/2015
EP 2971034 A1 1/2016
EP 3030682 A2 6/2016
EP 3044228 A4 4/2017
EP 2994509 B1 6/2017
EP 3204518 A1 8/2017
JP H07505530 A 6/1995
JP 2001518086 A 10/2001
JP 2002511276 A 4/2002
JP 2002536977 A 11/2002
JP 2002538790 A 11/2002
JP 2006503586 A 2/2006
JP 2006238724 A 9/2006
JP 2008505642 A 2/2008
JP 2008097189 A 4/2008
JP 2008523786 A 7/2008
JP 2008214343 A 9/2008
JP 2009294195 A 12/2009
JP 2016527313 A 9/2016
WO WO-9015070 A1 12/1990
WO WO-9210092 A1 6/1992
WO WO-9210588 A1 6/1992
WO WO-9309668 A1 5/1993
WO WO-9320242 A1 10/1993
WO WO-9525116 A1 9/1995
WO WO-9526397 A1 10/1995
WO WO-9615861 A1 5/1996
WO WO-9710365 A1 3/1997
WO WO-9822541 A2 5/1998
WO WO-9841531 A2 9/1998
WO WO-9942813 A1 8/1999
WO WO-9953101 A1 10/1999
WO WO-0013017 A2 3/2000
WO WO-0018957 A1 4/2000
WO WO-0042559 A1 7/2000
WO WO-0042560 A2 7/2000
WO WO-0042561 A2 7/2000
WO WO-0049142 A1 8/2000
WO WO-0053617 A1 9/2000
WO WO-0156216 A2 8/2001
WO WO-0210443 A1 2/2002
WO WO-0156216 A3 3/2002
WO WO-0220537 A2 3/2002
WO WO-0224597 A2 3/2002

(56) References Cited

FOREIGN PATENT DOCUMENTS

| | | | |
|---|---|---|---|
| WO | WO-0227638 | A1 | 4/2002 |
| WO | WO-0233669 | A1 | 4/2002 |
| WO | WO-02072791 | A2 | 9/2002 |
| WO | WO-03040410 | A1 | 5/2003 |
| WO | WO-03046223 | A1 | 6/2003 |
| WO | WO-03054232 | A2 | 7/2003 |
| WO | WO-03060084 | A2 | 7/2003 |
| WO | WO-03064026 | A1 | 8/2003 |
| WO | WO-03064027 | A2 | 8/2003 |
| WO | WO-03064699 | A2 | 8/2003 |
| WO | WO-03065038 | A2 | 8/2003 |
| WO | WO-03066212 | A2 | 8/2003 |
| WO | WO-03089605 | A2 | 10/2003 |
| WO | WO-03093504 | A1 | 11/2003 |
| WO | WO-03100012 | A2 | 12/2003 |
| WO | WO-2004024886 | A2 | 3/2004 |
| WO | WO-2004029220 | A2 | 4/2004 |
| WO | WO-2004029586 | A1 | 4/2004 |
| WO | WO-2004031351 | A2 | 4/2004 |
| WO | WO-2004031399 | A2 | 4/2004 |
| WO | WO-2004059556 | A2 | 7/2004 |
| WO | WO-03060084 | A3 | 8/2004 |
| WO | WO-2005014850 | A2 | 2/2005 |
| WO | WO-2005051970 | A2 | 6/2005 |
| WO | WO-2005059096 | A2 | 6/2005 |
| WO | WO-2005059097 | A2 | 6/2005 |
| WO | WO-2005093092 | A2 | 10/2005 |
| WO | WO-2006023144 | | 3/2006 |
| WO | WO-2006044956 | A1 | 4/2006 |
| WO | WO-2006076679 | A1 | 7/2006 |
| WO | WO-2006116476 | A1 | 11/2006 |
| WO | WO-2007073171 | A2 | 6/2007 |
| WO | WO-2007109221 | A2 | 9/2007 |
| WO | WO-2007118214 | A2 | 10/2007 |
| WO | WO-2007120627 | A2 | 10/2007 |
| WO | WO-2007137242 | A2 | 11/2007 |
| WO | WO-2008003116 | A2 | 1/2008 |
| WO | WO-2008006078 | A2 | 1/2008 |
| WO | WO-2008027558 | A2 | 3/2008 |
| WO | WO-2008045380 | | 4/2008 |
| WO | WO-2008054543 | A2 | 5/2008 |
| WO | WO-2008063134 | A1 | 5/2008 |
| WO | WO-2008063135 | A1 | 5/2008 |
| WO | WO-2008068280 | A1 | 6/2008 |
| WO | WO-2008103474 | A1 | 8/2008 |
| WO | WO-2008109176 | A2 | 9/2008 |
| WO | WO-2009132876 | A1 | 11/2009 |
| WO | WO-2010001251 | A2 | 1/2010 |
| WO | WO-2010025310 | A2 | 3/2010 |
| WO | WO-2010025566 | A1 | 3/2010 |
| WO | WO-2010027512 | A2 | 3/2010 |
| WO | WO-2010089412 | A1 | 8/2010 |
| WO | WO-2010141249 | A2 | 12/2010 |
| WO | WO-2010141433 | A2 | 12/2010 |
| WO | WO-2011020529 | A2 | 2/2011 |
| WO | WO-2010141433 | A3 | 4/2011 |
| WO | WO-2011053957 | A2 | 5/2011 |
| WO | WO-2011056644 | A2 | 5/2011 |
| WO | WO-2011056872 | A2 | 5/2011 |
| WO | WO-2011066185 | A1 | 6/2011 |
| WO | WO-2011066186 | A1 | 6/2011 |
| WO | WO-2011085075 | A2 | 7/2011 |
| WO | WO-2011103468 | A2 | 8/2011 |
| WO | WO-2011109031 | A1 | 9/2011 |
| WO | WO-2011143556 | A1 | 11/2011 |
| WO | WO-2011150168 | A1 | 12/2011 |
| WO | WO-2011161413 | A2 | 12/2011 |
| WO | WO-2012013913 | A1 | 2/2012 |
| WO | WO-2012061832 | A1 | 5/2012 |
| WO | WO-2012078312 | A2 | 6/2012 |
| WO | WO-2012149171 | A1 | 11/2012 |
| WO | WO-2012154201 | A1 | 11/2012 |
| WO | WO-2013010062 | A2 | 1/2013 |
| WO | WO-2013030827 | A1 | 3/2013 |
| WO | WO-2013032850 | A2 | 3/2013 |
| WO | WO-2013036668 | A1 | 3/2013 |
| WO | WO-2013049227 | A2 | 4/2013 |
| WO | WO-2013101896 | A1 | 7/2013 |
| WO | WO-2013134881 | A1 | 9/2013 |
| WO | WO-2013154770 | A1 | 10/2013 |
| WO | WO-2013170168 | A1 | 11/2013 |
| WO | WO-2013177220 | A1 | 11/2013 |
| WO | WO-2014004393 | A1 | 1/2014 |
| WO | WO-2014008447 | A1 | 1/2014 |
| WO | WO-2014021938 | A1 | 2/2014 |
| WO | WO-2014035693 | A2 | 3/2014 |
| WO | WO-2014088693 | A1 | 6/2014 |
| WO | WO-2014089160 | A1 | 6/2014 |
| WO | WO-2014093330 | A1 | 6/2014 |
| WO | WO-2014093694 | A1 | 6/2014 |
| WO | WO-2014151117 | A1 | 9/2014 |
| WO | WO-2014151696 | A1 | 9/2014 |
| WO | WO-2014160004 | A1 | 10/2014 |
| WO | WO-2014160059 | A1 | 10/2014 |
| WO | WO-2014206304 | A1 | 12/2014 |
| WO | WO-2015017527 | A2 | 2/2015 |
| WO | WO-2015021080 | A2 | 2/2015 |
| WO | WO-2015021280 | A1 | 2/2015 |
| WO | WO-2015031689 | A1 | 3/2015 |
| WO | WO-2015040075 | A1 | 3/2015 |
| WO | WO-2015054292 | A1 | 4/2015 |
| WO | WO-2015066174 | A1 | 5/2015 |
| WO | WO-2015081114 | A2 | 6/2015 |
| WO | WO-2015081142 | A1 | 6/2015 |
| WO | WO-2015081440 | A1 | 6/2015 |
| WO | WO-2015090879 | A1 | 6/2015 |
| WO | WO-2015095404 | A2 | 6/2015 |
| WO | WO-2015120403 | A1 | 8/2015 |
| WO | WO-2015136072 | A1 | 9/2015 |
| WO | WO-2015160004 | A1 | 10/2015 |
| WO | WO-2015175832 | A1 | 11/2015 |
| WO | WO-2016007604 | A1 | 1/2016 |
| WO | WO-2016011080 | A2 | 1/2016 |
| WO | WO-2016022557 | A1 | 2/2016 |
| WO | WO-2016053883 | A1 | 4/2016 |
| WO | WO-2016055956 | A1 | 4/2016 |
| WO | WO-2016065056 | A1 | 4/2016 |
| WO | WO-2016126882 | A1 | 8/2016 |
| WO | WO-2016126987 | A1 | 8/2016 |
| WO | WO-2016130868 | A2 | 8/2016 |
| WO | WO-2016161244 | A2 | 10/2016 |
| WO | WO-2016162127 | A1 | 10/2016 |
| WO | WO-2016164779 | A1 | 10/2016 |
| WO | WO-2016172377 | A1 | 10/2016 |
| WO | WO-2016173719 | A1 | 11/2016 |
| WO | WO-2016183100 | A1 | 11/2016 |
| WO | WO-2017049231 | A1 | 3/2017 |
| WO | WO-2017053450 | A1 | 3/2017 |
| WO | WO-2017059399 | A1 | 4/2017 |
| WO | WO-2017095958 | A1 | 6/2017 |
| WO | WO-2017100441 | A1 | 6/2017 |
| WO | WO-2017118761 | A1 | 7/2017 |
| WO | WO-2017158103 | A1 | 9/2017 |
| WO | WO-2017214574 | A1 | 12/2017 |
| WO | WO-2018026920 | A1 | 2/2018 |
| WO | WO-2018038772 | A1 | 3/2018 |
| WO | WO-2018057526 | A2 | 3/2018 |
| WO | WO-2018094263 | A1 | 5/2018 |
| WO | WO-2018112426 | A1 | 6/2018 |
| WO | WO-2018119246 | A1 | 6/2018 |
| WO | WO-2018156792 | A1 | 8/2018 |
| WO | WO-2018170164 | A1 | 9/2018 |
| WO | WO-2018170169 | A1 | 9/2018 |
| WO | WO-2018170559 | A1 | 9/2018 |
| WO | WO-2018200380 | A1 | 11/2018 |
| WO | WO-2018231872 | A1 | 12/2018 |
| WO | WO-2019014781 | A1 | 1/2019 |
| WO | WO-2019051501 | A1 | 3/2019 |
| WO | WO-2019079769 | A1 | 4/2019 |
| WO | WO-2019084500 | A1 | 5/2019 |
| WO | WO-2019136175 | A1 | 7/2019 |
| WO | WO-2019222706 | A1 | 11/2019 |
| WO | WO-2020139871 | A1 | 7/2020 |
| WO | WO-2020176362 | A1 | 9/2020 |

(56) References Cited

FOREIGN PATENT DOCUMENTS

| | | | |
|---|---|---|---|
| WO | WO-2020176678 | A1 | 9/2020 |
| WO | WO-2020176680 | A1 | 9/2020 |
| WO | WO-2020257612 | A1 | 12/2020 |
| WO | WO-2021119193 | A2 | 6/2021 |

OTHER PUBLICATIONS

Xu et al.: Coordination between the Polymerase and 5 '-Nuclease Components of DNA Polymerase I of *Escherichia coli*. The Journal of Biological Chemistry. 275(27):20949-20955 (2000).
Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Acevedo-Rocha et al.: Directed evolution of stereoselective enzymes based on genetic selection as opposed to screening systems. J. Biotechnol. 191:3-10 (2014).
Adessi et al.: Solid phase DNA amplification: characterisation of primer attachment and amplification mechanisms. Nucleic Acids Res. 28(20):E87, 2000.
Alberts et al.: Molecular Biology of the Cell. 4th edition. New York: Garland Science; 2002. The Generation of Antibody Diversity. https://www.ncbi.nlm.nih.gov/books/NBK26860/.
Alexeyev et al.: Gene synthesis, bacterial expression and purification of the Rickettsia prowazekii ATP/ADP translocase, Biochimica et Biophysics Acta, 1419:299-306, 1999.
Al-Housseiny et al.: Control of interfacial instabilities using flow geometry Nature Physics, 8:747-750, 2012.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Amblard et al.: A magnetic manipulator for studying local rheology and micromechanical properties of biological systems, Rev. Sci. Instrum., 67(3):18-827, 1996.
Andoni and Indyk. Near-Optimal Hashing Algorithms for Approximate Nearest Neighbor in High Dimensions, Communications of the ACM, 51(1):117-122, 2008.
Arand et al.: Structure of Rhodococcus erythropolis limonene-1,2-epoxide hydrolase reveals a novel active site. EMBO J. 22:2583-2592 (2003).
Arkles et al.: The Role of Polarity in the Structure of Silanes Employed in Surface Modification. Silanes and Other Coupling Agents. 5:51-64, 2009.
Arkles. Hydrophobicity, Hydrophilicity Reprinted with permission from the Oct. 2006 issue of Paint & Coatings Industry magazine, Retrieved on Mar. 19, 2016, 10 pages.
Assembly manual for the POSaM: The ISB Piezoelelctric Oligonucleotide Synthesizer and Microarrayer, The Institute for Systems Biology, May 28, 2004 (50 pages).
Assi et al.: Massive-parallel adhesion and reactivity-measurements using simple and inexpensive magnetic tweezers. J. Appl. Phys. 92(9):5584-5586 (2002).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Au et al.: Gene synthesis by a LCR-based approach: high level production of Leptin-L54 using synthetic gene in *Escherichia coli*. Biochemical and Biophysical Research Communications 248:200-203 (1998).
Baedeker et al.: Overexpression of a designed 2.2kb gene of eukaryotic phenylalanine ammonialyase in *Escherichia coli*•. FEBS Letters, 457:57-60, 1999.
Barbee et al.: Magnetic Assembly of High-Density DNA Arrays for Genomic Analyses. Anal Chem. 80(6):2149-2154, 2008.
Barton et al.: A desk electrohydrodynamic jet printing system. Mechatronics, 20:611-616, 2010.
Beaucage et al.: Advances in the synthesis of oligonucleotides by the phosphoramidite approach. Tetrahedron. 48:2223-2311, 1992.
Beaucage et al.: Deoxynucleoside phosphoramidites—A new class of key intermediates for deoxypolynucleotide synthesis. Tetrahedron Lett. 22(20):1859-1862, 1981.
Beaucage et al.: The Chemical synthesis of DNA/RNA Chapter 2 in: Encyclopedia of Cell Biology, 1:36-53, 2016.
Beaulieu et al.: PCR candidate region mismatch scanning adaptation to quantitative, high-throughput genotyping, Nucleic Acids Research, 29(5):1114-1124, 2001.
Beigelman et al.: Base-modified phosphoramidite analogs of pyrimidine ribonucleosides for RNA structure-activity studies. Methods Enzymol. 317:39-65, 2000.
Bethge et al.: Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%2001igonucleotides%20%2864-108%29.pdf.
Binkowski et al.: Correcting errors in synthetic DNA through consensus shuffling. Nucleic Acids Research, 33(6):e55, 8 pages, 2005.
Biswas et al.: Identification and characterization of a thermostable MutS homolog from Thennus aquaticus, The Journal of Biological Chemistry, 271(9):5040-5048, 1996.
Biswas et al.: Interaction of MutS protein with the major and minor grooves of a heteroduplex DNA, The Journal of Biological Chemistry, 272(20):13355-13364, 1997.
Bjornson et al.: Differential and simultaneous adenosine Di- and Triphosphate binding by MutS, The Journal of Biological Chemistry, 278(20):18557-18562, 2003.
Blanchard et al.: High-Density Oligonucleotide Arrays, Biosensors & Bioelectronics, 11(6/7):687-690, 1996.
Blanchard: Genetic Engineering, Principles and Methods, vol. 20, Ed. J. Sedlow, New York: Plenum Press, p. 111-124, 1979.
Blawat et al.: Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al.: A DNA-Based Archival Storage System, in International Conference on Architectural Support for Programming Languages and Operating Systems (ASPLOS), Apr. 2-6, 2016, Atlanta, GA, 2016, 637-649.
Borovkov et al.: High-quality gene assembly directly from unpurified mixtures of microassay-synthesized oligonucleotides. Nucleic Acid Research, 38(19):e180, 10 pages, 2010.
Brunet: Aims and methods of biosteganography. Journal of Biotechnology, 226:56-64, 2016.
Buermans et al.: Next Generation sequencing technology: Advances and applications, Biochimica et Biophysica Acta (BBA)—Molecular Basis of Disease, 1842:1931-1941, 2014.
Butler et al.: In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for The Nineties, vol. 20, p. 109, ed. By Abraham Ulman, San Diego: Academic Press, 1995.
Cardelli. Two-Domain DNA Strand Displacement, Electron. Proc. Theor. Comput. Sci., 26:47-61, 2010.
Carlson. Time for New DNA Synthesis and Sequencing Cost Curves, 2014. [Online]. Available: http://www.synthesis.cc/synthesis/2014/02/time_for_new_cost_curves_2014. 10 pages.
Carr et al.: Protein-mediated error correction for de novo DNA synthesis. Nucleic Acids Res. 32(20):e162, 9 pages, 2004.
Carter and Friedman. DNA synthesis and Biosecurity: Lessons learned and options for the future. J. Craig Venter Institute, La Jolla, CA, 28 pages, Oct. 2015.
Caruthers. Chemical synthesis of deoxyoligonucleotides by the phosphoramidite method. In Methods in Enzymology, Chapter 15, 154:287-313, 1987.
Caruthers, The Chemical Synthesis of DNA/RNA: Our Gift to Science. J. Biol. Chem., 288(2):1420-1427, 2013.

(56) References Cited

OTHER PUBLICATIONS

Caruthers. Gene synthesis machines: DNA chemistry and its uses. Science 230(4723):281-285 (1985).
Casmiro et al.: PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello et al.: Chemical synthesis of poliovirus cDNA: generation of infectious virus in the absence of natural template. Science. 297(5583):1016-8, 2000.
Chalmers et al.: Scaling up the ligase chain reaction-based approach to gene synthesis. Biotechniques. 30(2):249-52, 2001.
Chan et al.: Natural and engineered nicking endonucleases—from cleavage mechanism to engineering of strand-specificity. Nucleic Acids Res. 39(1):1-18, 2011.
Chen et al.: Programmable chemical controllers made from DNA, Nat. Nanotechnol., 8(10):755-762, 2013.
Chen et al.: Chemical modification of gene silencing oligonucleotides for drug discovery and development. Drug Discov Today. 10(8):587-93 2005.
Cheng et al.: High throughput parallel synthesis of oligonucleotides with 1536 channel synthesizer. Nucleic Acids Res. 30(18):e93, 2002.
Chilamakuri et al.: Performance comparison of four exome capture systems for deep sequencing. BMC Genomics 15(1):449 (2014).
Cho et al.: Capillary passive valve in microfluidic systems. NSTI—Nanotech. 2004; 1:263-266.
Chrisey et al.: Fabrication of patterned DNA surfaces Nucleic Acids Research, 24(15):3040-3047 (1996).
Chung et al.: One-step preparation of competent *Escherichia coli*: Transformation and storage of bacterial cells in the same solution. Proc Natl Acad Sci U S A. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nature Methods, 1(13):241-248, 2004.
Cohen et al.: Human population: The next half century. Science, 302:1172-1175, 2003.
Crick. On protein synthesis. Symp Soc Exp Biol12:138-163,1958.
Cruse et al.: Atlas of Immunology, Third Edition. Boca Raton:CRC Press (pp. 282-283) (2010).
Cutler et al.: High-throughput variation detection and genotyping using microarrays, Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
De Mesmaeker et al.: Backbone modifications in oligonucleotides and peptide nucleic acid systems. Curr Opin Struct Biol. Jun. 1995;5(3):343-55.
De Silva et al.: New Trends of Digital Data Storage in DNA. BioMed Res Int. 2016:8072463 (2016).
Deamer et al.: Characterization of nucleic acids by nanopore analysis, Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Dietrich et al.: Gene assembly based on blunt-ended double-stranded DNA-modules, Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of *E. coli* by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill. The Genome Sequencer FLXTM System-Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie et al.: Guanine modification during chemical DNA synthesis. Nucleic Acids Res. Oct. 26, 1987;15(20):8333-49.
Eisen: A phylogenomic study of the MutS family of proteins, Nucleic Acids Research, vol. 26, No. 18, 4291-4300 (1998).
Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski. DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
European Patent Application No. 16871446.7 First Official Action dated Nov. 13, 2019.

(56) References Cited

OTHER PUBLICATIONS

European Patent Application No. 17844060.8 Extended Search Report dated Apr. 20, 2020.
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to PCR. PCR Methods Appl. Aug. 1991;1(1):25-33.
Fedoryak et al.: Brominated hydroxyquinoline as a photolabile protecting group with sensitivity to multiphoton excitation, Org. Lett., vol. 4, No. 2 , 3419-3422 (2002).
Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.
Fodor et al.: Light-directed, spatially addressable parallel chemical synthesis. Science. 251(4995):767-773 (1991).
Fogg et al.: Structural basis for uracil recognition by archaeal family B DNA polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A method for the generation of combinatorial antibody libraries using pIX phage display. PNAS 99(20):12612-12616 (2002).
Gao et al.: A flexible light-directed DNA chip synthesis gated by deprotection using solution photogenerated acids. Nucleic Acids Res. Nov. 15, 2001;29(22):4744-50.
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresisof isolated, highly charged colloidal spheres, Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Creation of a Bacterial Cell Controlled by A Chemically Synthesized Genome. Science 329(5989):52-56 (2010).
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Gosse et al.: Magnetic tweezers: micromanipulation and force measurement at the molecular level, Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).
Hanahan and Cold Spring Harbor Laboratory. Studies on transformation of *Escherichia coli* with plasmids J. Mol. Biol. 166:557-580 (1983).
Hanahan et al.: Plasmid transformation of *Escherichia coli* and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993;21(10):2287-91.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Heckers et al.: Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al.: DNAWorks: an automated method for designing oligonucleotides for PCR-based gene synthesis, Nucleic Acids Research, vol. 30, No. 10, e43, 7 pages (2002).
Hosu et al.: Magnetic tweezers for intracellular applications*, Rev. Sci. Instrum., vol. 74, No. 9, 4158-4163 (Sep. 2003).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Huang et al.: Three-dimensional cellular deformation analysis with a two-photon magnetic manipulator workstation, Biophysical Journal, vol. 82, No. 4, 2211•2223 (Apr. 2002).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.

(56) References Cited

OTHER PUBLICATIONS

In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/019268 International Preliminary Report on Patentability dated Sep. 6, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Jackson et al.: Recognition of DNA base mismatches by a rhodium intercalator, J. Am. Chem. Soc., vol. 19, 12986•12987 (1997).
Jacobs et al.: DNA glycosylases: In DNA repair and beyond. Chromosoma 121:1-20 (2012)—http://www.ncbi.nlm.nih.gov/pmc/articles/PMC3260424/.
Jacobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer—Testis Antigen NY-ES0-1: Definition of Human Histocompatibility Leukocyte Antigen (HLA)-A2—binding Peptide Epitopes. J. Exp. Med. 187(2):265-270 (1998).
Jinek et al.: A Programmable dual-RNA-guided DNA endonuclease in adaptive bacterial immunity. Science, 337:816-821, 2012.
Jo et al.: Engineering therapeutic antibodies targeting G-protein-coupled receptors; Experimental & Molecular Medicine; 48; 9 pages (2016).
Karagiannis and El-Osta. RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment, Biochemistry, Vo. 34, 4593-4600 (1995).
Kelley et al.: Single-base mismatch detection based on charge transduction through DNA, Nucleic Acids Research, vol. 27, No. 24, 4830-4837 (1999).
Kim et al.: High-resolution patterns of quantum dots formed by electrohydrodynamic jet printing for light-emitting diodes. Nano Letters, 15:969-973, 2015.
Kim et al.: Site specific cleavage of DNA-RNA hybrids by zinc finger/Fok I cleavage domain fusions Gene, vol. 203, 43-49 (1997).
Kim et al.: Chimeric restriction endonuclease, Proc. Natl. Acad. Sci. USA, vol. 91,883-887 (Feb. 1994).
Kim, The interaction between Z-ONA and the Zab domain of double-stranded RNA adenosine deaminase characterized using fusion nucleases, The Journal of Biological Chemistry, vol. 274, No. 27, 19081-19086 (1999).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental Online Methods).
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip, Science, vol. 280, 1046-1048 (May 15, 1998).
Kosuri and Church. Large-scale de novo DNA synthesis: technologies and applications, Nature Methods, 11:499-507, 2014. Available at: http://www.nature.com/nmeth/journal/v11/n5/full/nmeth.2918.html.
Kosuri et al.: A scalable gene synthesis platform using high-fidelity DNA microchips Nat.Biotechnol., 28(12):1295-1299, 2010.
Krayden, Inc.: A Guide to Silane Solutions. Silane coupling agents. 7 pages. Published on May 31, 2005 at: http://krayden.com/pdf/xia_silane_chemistry.pdf.
Lagally et al.: Single-Molecule DNA Amplification and Analysis in an Integrated Microfluidic Device. Analytical Chemistry. 2001;73(3):565-570.
Lahue et al., DNA mismatch correction in a defined system, Science, vol. 425; No. 4914, 160-164 (Jul. 14, 1989).
Lambrinakos, A. et al.: Reactivity of potassium permanganate and tetraethylammonium chloride with mismatched bases and a simple mutation detection protocol,Nucleic Acids Research, vol. 27, No. 8, 1866-1874 (1999).
Landegren et al.: A ligase-mediated gene detection technique. Science. Aug. 26, 1988;241(4869):1077-80.
Lang, Matthew J. et al.: An automated two-dimensional optical force clamp for single molecule studies, Biophysical Journal, vol. 83, 491•501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon et al.: A massively parallel PicoTiterPlate based platform for discrete picoliter-scale polymerase chain reactions. Electrophoresis. Nov. 2003;24(21):3769-77.
Lee et al.: Microelectromagnets for the control of magnetic nanoparticles, Appl. Phys. Lett., vol. 79, No. 20, 3308-3310 (Nov. 12, 2001).
Lee et al.: A microfluidic oligonucleotide synthesizer. Nucleic Acids Research 2010 vol. 38(8):2514-2521. DOI: 10.1093/nar/gkq092.
Lee: Covalent End-Immobilization of Oligonucleotides onto Solid Surfaces; Thesis, Massachusetts Institute of Technology, Aug. 2001 (315 pages).
Leproust et al.: Synthesis of high-quality libraries of long (150mer) oligonucleotides by a novel depurination controlled process, Nucleic Acids Research, 35(8):2522-2540, 2010.
Leproust et al.: Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene et al.: Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).

(56) References Cited

OTHER PUBLICATIONS

Li et al.: Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Light source unit for printable patterning VUV-Aligner/ USHIO Inc., Link here: https://www.ushio.co.jp/en/products/1005.html, published Apr. 25, 2016, printed from the internet on Aug. 2, 2016, 3 pages.
Limbachiya et al.: Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz, Robert J. et al.: High density synthetic oligonucleotide arrays, Nature Genetics Supplement, vol. 21, 20-24 (Jan. 1999).
Lishanski, Alia et al.: Mutation detection by mismatch binding protein, MutS, in amplified DNA: application to the cystic fibrosis gene, Proc. Natl. Acad. Sci. USA, vol. 91, 2674-2678 (Mar. 1994).
Liu et al.: Comparison of Next-Generation Sequencing Systems. J Biomed Biotechnol 2012: 251364(2012).
Liu et al.: Rational design of CXCR4 specific antibodies with elongated CDRs. JACS, 136:10557-10560, 2014.
Liu et al.: Enhanced Signals and Fast Nucleic Acid Hybridization By Microfluidic Chaotic Mixing. Angew. Chem. Int. Ed. 2006; 45:3618-3623.
Lizardi et al.: Mutation detection and single-molecule counting using isothermal rolling-circle amplification. Nat Genet. Jul. 1998;19(3):225-32.
Li et al.: Functional domains in Fok I restriction endonuclease, Proc. Natl. Acad. Sci. USA, 89:4275-4279, 1992.
Lu et al.: Methyl-directed repair of DNA base-pair mismatches in vitro, Proc. Natl. Acad. Sci. USA, 80:4639-4643, 1983.
Lund et al.: A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma et al.: Versatile surface functionalization of cyclic olefin copolymer (COC) with sputtered SiO2 thin film for potential BioMEMS applications. Journal of Materials Chemistry, 11 pages, 2009.
Ma et al.: DNA synthesis, assembly and application in synthetic biology. Current Opinion in Chemical Biology. 16:260-267, 2012.
Mahato et al.: Modulation of gene expression by antisense and antigene oligodeoxynucleotides and small interfering RNA Expert Opin. Drug Delivery, 2(1):3-28, 2005.
Margulies et al.: Genome sequencing in open microfabricated high-density picolitre reactors. Nature. 437(7057):376-80, 2005.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Matteucci et al.: Synthesis of deoxyoligonucleotides on a polymer support. J. Am. Chem. Soc. 103(11):3185-3191, 1981.
Matzas et al.: Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24: 245-248, 1983.
Mcgall et al.: Light-directed synthesis of high-density oligonucleotide arrays using semiconductor photoresists. Proc Natl Acad Sci U S A. 93(24):13555-60, 1996.
Mcgall et al.: The Efficiency of Light-Directed Synthesis of DNA Arrays on Glass Substrates. J. Am. Chem. Soc. 119(22):5081-5090, 1997.
Mei et al.: Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Meynert et al.: Quantifying single nucleotide variant detection sensitivity in exome sequencing. BMC Bioinformatics 14:195 (2013).
Meynert et al.: Variant detection sensitivity and biases in whole genome and exome sequencing. BMC Bioinformatics 15:247 (2014).
Milo and Phillips. Numbers here reflect the number of protein coding genes and excludes tRNA and non-coding RNA. Cell Biology by the Numbers, p. 286, 2015.
Mitra et al.: In situ localized amplification and contact replication of many individual DNA molecules. Nucleic Acids Res. 27(24):e34, 1999.
Morin et al.: Profiling the HeLa S3 transcriptome using randomly primed cDNA and massively parallel short-read sequencing. Biotechniques, 45:81-94, 2008.
Morris and Stauss. Optimizing T-cell receptor gene therapy for hematologic malignancies. Blood, 127(26):3305-3311, 2016.
Muller et al.: Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani et al.: Recognition of a single guanine bulge by 2-Acylamino-1,8-naphthyridine, J. Am. Chem. Soc., vol. 122, 2172-2177 (2000).
Neiman M.S.: Negentropy principle in information processing systems. Radiotekhnika, 1966, No. 11, p. 2-9.
Neiman M.S.: On the bases of the theory of information retrieval. Radiotekhnika, 1967, No. 5, p. 2-10.
Neiman M.S.: On the molecular memory systems and the directed mutations. Radiotekhnika, 1965, No. 6, pp. 1-8.
Neiman M.S.: On the relationships between the reliability, performance and degree of microminiaturization at the molecular-atomic level. Radiotekhnika, 1965, No. 1, pp. 1-9.
Neiman M.S.: Some fundamental issues of microminiaturization. Radiotekhnika, 1964, No. 1, pp. 3-12.
Nishikura. A short primer on RNAi: RNA-directed RNA polymerase acts as a key catalyst Cell, 107:415-418, 2001.
Nour-Eldin et al.: USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman et al.: Genetic applications of an inverse polymerase chain reaction. Genetics. Nov. 1988;120(3):621-3.
Organick et al.: Random access in large-scale DNA data storage. Nature Biotechnology, Advance Online Publication, 8 pages, 2018.
Organick et al.: Scaling up DNA data storage and random access retrieval, bioRxiv, preprint first posted online Mar. 7, 2017, 14 pages.
Pan et al.: An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
Paul et al.: Acid binding and detritylation during oligonucleotide synthesis. Nucleic Acids Research. 15. pp. 3048-3052 (1996).
PCT/IL2012/000326 International Preliminary Report on Patentability dated Dec. 5, 2013.
PCT/IL2012/000326 International Search Report dated Jan. 29, 2013.

(56) References Cited

OTHER PUBLICATIONS

PCT/US2014/049834 International Preliminary Report on Patentability dated Feb. 18, 2016.
PCT/US2014/049834 International Search Report and Written Opinion dated Mar. 19, 2015.
PCT/US2014/049834, Invitation to Pay Additional Fees and, where applicable, protest fee, dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation To Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Preliminary Report on Patentability dated Dec. 26, 2019.
PCT/US2018/037152 International Search Report and Written Opinion dated Aug. 28, 2018.
PCT/US2018/037161 International Preliminary Report on Patentability dated Dec. 17, 2019.
PCT/US2018/037161 International Search Report and Written Opinion dated Oct. 22, 2018.
PCT/US2018/037161 Invitation to Pay Additional Fees dated Aug. 27, 2018.
PCT/US2018/050511 International Preliminary Report on Patentability dated Mar. 26, 2020.
PCT/US2018/056783 International Preliminary Report on Patentability dated Apr. 30, 2020.
PCT/US2018/056783 International Search Report and Written Opinion of the International Searching Authority dated Dec. 20, 2018.
PCT/US2018/057857 International Preliminary Report on Patentability dated Apr. 28, 2020.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
PCT/US2019/068435 International Search Report and Written Opinion dated Apr. 23, 2020.
PCT/US2020/019986 Invitation to Pay Additional Fees dated Jun. 5, 2020.
PCT/US2020/019988 Invitation to Pay Additional Fees dated Jun. 8, 2020.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-lis restriction enzyme aarl. Sep. 16, 2009, 7 pages.
Pellois et al.: Individually addressable parallel peptide synthesis on microchips, Nature Biotechnology, vol. 20 , 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.
Prodromou et al.: Recursive PCR: a novel technique for total gene synthesis. Protein Eng. Dec. 1992;5(8):827-9.
PubChem Data Sheet Acetonitrile. Printed from website https://pubchem.ncbi.nlm.nih.gov/ pp. 1-124 (2020).
PubChem Data Sheet Methylene Chloride. Printed from website https://pubchem.ncbi.nlm.nih.gov/ pp. 1-140 (2020).
Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.
Qian, et al.: Neural network computation with DNA strand displacement cascades, Nature, 475(7356):368-372, 2011.
Quan et al.: Parallel on-chip gene synthesis and application to optimization of protein expression, Nature Biotechnology, 29(5):449-452, 2011.
Rafalski and Morgante. Corn and humans: recombination and linkage disequilibrium in two genomes of similar size. Trends in Genetics, 20(2):103-111, 2004.

(56) References Cited

OTHER PUBLICATIONS

Raje and Murma, A Review of electrohydrodynamic-inkjet printing technology. International Journal of Emerging Technology and Advanced Engineering, 4(5):174-183, 2014.
Rajpal et al.: A general method for greatly improving the affinity of antibodies by using combinatorial libraries. Proc. Natl. Acad. Sci. 102(24):8466-8471 (2005).
Rastegari et al.: XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond et al.: Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al.: Origin and evolution of spliceosomal introns. Biology Direct, 7:11, 2012.
Ruminy et al.: Long-range identification of hepatocyte nuclear factor-3 (FoxA) high and low-affinity binding Sites with a chimeric nuclease, J. Mol. Bioi., vol. 310, 523-535 (2001).
Saaem et al.: In situ synthesis of DNA microarray on functionalized cyclic olefin copolymer substrate ACS Applied Materials & Interfaces, 2(2):491-497, 2010.
Saboulard et al.: High-throughput site-directed mutagenesis using oligonucleotides synthesized on DNA chips. Biotechniques. Sep. 2005;39(3):363-8.
Sacconi et al.: Three-dimensional magneto-optic trap for micro-object manipulation, Optics Letters, vol. 26, No. 17, 1359-1361 (Sep. 1, 2001).
Saiki et al.: Analysis of enzymatically amplified beta-globin and HLA-DQ alpha DNA with allele-specific oligonucleotide probes. Nature 324:163-166 (1986).
Sandhu et al.: Dual asymmetric PCR: one-step construction of synthetic genes. Biotechniques. Jan. 1992;12(1):14-6.
Sargolzaei et al.: Extent of linkage disequilibrium in Holstein cattle in North America. J.Dairy Science, 91:2106-2117, 2007.
Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al.: Microchip electrophoresis: a method for high-speed SNP detection. Nucleic Acids Res 28(9):E43 (2000).
Schmitt et al.: New strategies in engineering T-cell receptor gene-modified T cells to more effectively target malignancies. Clinical Cancer Research, 21(23):5191-5197, 2015.
Seelig et al.: Enzyme-Free Nucleic Acid Logic Circuits, Science 314(5805):1585-1588, 2006.
Sharan et al.: Recombineering: a homologous recombination-based method of genetic engineering. Nat Profile 4(2):1-37 (originally pp. 206-223) (2009).
Sharpe and Mount. Genetically modified T cells in cancer therapy: opportunities and challenges. Disease Models and Mechanisms, 8:337-350, 2015.
Sierzchala, Agnieszka B. et al.: Solid-phase oligodeoxynucleotide synthesis : a two-step cycle using peroxy anion deprotection, J. Am. Chem. Soc., vol. 125, No. 44, 13427-13441 (2003).
Simonyan and Zisserman. Very Deep Convolutional Networks for Large-Scale Image Recognition, Published as a conference paper at Int. Conf. Learn. Represent., pp. 1-14, 2015.
Singh-Gasson. Sangeet et al.: Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith et al.: Removal of Polymerase-Produced mutant sequences from PCR products, Proc. Natl. Acad. Sci. USA, vol. 94, 6847-6850 (Jun. 1997).
Smith et al.: Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith et al.: Generation of cohesive ends on PCR products by UDG-mediated excision of dU, and application for cloning into restriction digest-linearized vectors. PCR Methods Appl. May 1993;2(4):328-32.
Smith et al.: Mutation detection with MutH, MutL, and MutS mismatch repair proteins, Proc. Natl. Acad. Sci. USA, vol. 93, 4374-4379 (Apr. 1996).
Smith et al.: Direct mechanical measurements of the elasticity of single DNA molecules using magnetic beads, Science, vol. 258, 1122-1126 (Nov. 13, 1992).
Solomon et al.: Genomics at Agilent: Driving Value in DNA Sequencing.https://www.agilent.com/labs/features/2010_genomics.html, 8 pages (Aug. 5, 2010).
Soni et al.: Progress toward ultrafast DNA sequencing using solid-state nanopores. Clin Chem. Nov. 2007;53(11):1996-2001. Epub Sep. 21, 2007.
Southern et al.: Analyzing and comparing nucleic acid sequences by hybridization to arrays of oligonucleotides: evaluation using experimental models. Genomics. Aug. 1992;13(4):1008-17.
Sproat et al.: An efficient method for the isolation and purification of oligoribonucleotides. Nucleosides & Nucleotides. 1995; 14(1 &2):255-273.
Srivannavit et al.: Design and fabrication of microwell array chips for a solution-based, photogenerated acid-catalyzed parallel oligonuclotide DNA synthesis. Sensors and Actuators A, 116:150-160, 2004.
Srivastava et al.: RNA synthesis: phosphoramidites for RNA synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel. The Flow-Thru Chip A Three-dimensional biochip platform. In: Schena, Microarray Biochip Technology, Chapter 5, Natick, MA: Eaton Publishing, 2000, 33 pages.
Stemmer et al.: Single-step assembly of a gene and entire plasmid from large numbers of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz et al.: Novel fluoride-labile nucleobase-protecting groups for the synthesis of 3'(2')-O-amino-acylated RNA sequences. Helv. Chim. Acta. 2000; 83(9):2477-2503.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning of the Stereoselectivity of an Epoxide Hydrolase. ACS Catal. 6:1590-1597 (2016).
Takahashi. Cell-free cloning using multiply-primed rolling circle amplification with modified RNA primers. Biotechniques. Jul. 2009;47(1):609-15. doi: 10.2144/000113155.
Tanase et al.: Magnetic trapping of multicomponent nanowires, The Johns Hopkins University, Baltimore, Maryland, p. 1-3 (Jun. 25, 2001).
Taylor et al.: Impact of surface chemistry and blocking strategies on DNA microarrays. Nucleic Acids Research, 31(16):e87, 19 pages, 2003.

(56) References Cited

OTHER PUBLICATIONS

The Hood Laboratory, Beta Group. Assembly Manual for the POSaM: The ISB Piezoelelctric Oligonucleotide Synthesizer and Microarrayer, Inkjet Microarrayer Manual Version 1.2, 50 pages, May 28, 2004.
The SLIC. Gibson, CPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-4.
Tsai et al.: Dimeric CRISPR RNA-guided Fokl nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
U.S. Appl. No. 14/241,874 Final Office Action dated Jan. 28, 2019.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/151,316 Office Action dated Oct. 4, 2019.
U.S. Appl. No. 15/151,316 Final Office Action dated Feb. 21, 2019.
U.S. Appl. No. 15/154,879 Notice of Allowance dated Feb. 1, 2017.
U.S. Appl. No. 15/156,134 Final Office Action dated Jan. 3, 2020.
U.S. Appl. No. 15/156,134 Office Action dated Apr. 4, 2019.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/272,004 Office Action dated Jun. 12, 2020.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/619,322 Final Office Action dated Mar. 30, 2020.
U.S. Appl. No. 15/619,322 Office Action dated Aug. 14, 2019.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated May 19, 2020.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Final Office Action dated Jun. 15, 2020.
U.S. Appl. No. 15/921,479 Office Action dated Nov. 12, 2019.
U.S. Appl. No. 15/921,479 Restriction Requirement dated May 24, 2019.
U.S. Appl. No. 15/921,537 Office Action dated Apr. 1, 2020.
U.S. Appl. No. 15/960,319 Office Action dated Aug. 16, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/006,581 Office Action dated Sep. 25, 2019.
U.S. Appl. No. 16/031,784 Office Action dated May 12, 2020.
U.S. Appl. No. 16/039,256 Restriction Requirement dated May 18, 2020.
U.S. Appl. No. 16/128,372 Restriction Requirement dated May 18, 2020.
U.S. Appl. No. 16/165,952 Office Action dated Mar. 12, 2020.
U.S. Appl. No. 16/239,453 Office Action dated May 11, 2020.
U.S. Appl. No. 16/239,453 Office Action dated Nov. 7, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Final Office Action dated Apr. 15, 2020.
U.S. Appl. No. 16/530,717 Office Action dated Sep. 6, 2019.
U.S. Appl. No. 16/535,777 Office Action dated Jan. 23, 2020.
U.S. Appl. No. 16/535,779 First Action Interview dated Feb. 10, 2020.
U.S. Appl. No. 14/452,429 Office Action dated Apr. 9, 2015.
U.S. Appl. No. 15/603,013 Office Action dated Jun. 26, 2019.
Unger et al.: Monolithic microfabricated valves and pumps by multilayer soft lithography. Science. Apr. 7, 2000;288(5463):113-6.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.

(56) References Cited

OTHER PUBLICATIONS

Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing, IEEE Journal of Selected Topics in Quantum Electronics, vol. 2, No. 4, 1066-1076 (Dec. 1996).
Voldmans et al.: Holding forces of single-particle dielectrophoretic traps. Biophysical Journal, vol. 80, No. 1, 531-541 (Jan. 2001).
Vos et al.: AFLP:A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah et al.: Structure of Fok I has implications for DNA cleavage, Proc. Natl. Acad. Sci. USA, vol. 95, 10564-10569 (Sep. 1998).
Wah et al.: Structure of the multimodular endonuclease Fok I bound to DNA, Nature, vol. 388, 97-100 (Jul. 1997).
Walker et al.: Strand displacement amplification—an isothermal, in vitro DNA amplification technique. Nucleic Acids Res. Apr. 11, 1992;20(7):1691-6.
Wan et al.: Deep Learning for Content-Based Image Retrieval: A comprehensive study, in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 18, 2011;6(2):e16765. doi: 10.1371/journal.pone.0016765.
Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse et al.: Analysis of the mismatch and insertion/deletion binding properties of Thermus thermophilus, HB8, MutS, Biochemical and Biophysical Research Communications, vol. 233, 834-837 (1997).
Wiedenheft et al.: RNA-guided genetic silencing systems in bacteria and archaea. Nature 482:331-338 (2012).
Wijshoff. Structure and fluid-dynamics in Piezo inkjet printheads. Thesis. Venio, The Netherlands, published 2008, p. 1-185.
Wirtz. Direct measurement of the transport properties of a single DNA molecule, Physical Review Letters, vol. 75, No. 12, 2436-2439 (Sep. 18, 1995).
Withers-Martinez et al.: PCR-based gene synthesis as an efficient approach for expression of the A+ T-rich malaria genome, Protein Engineering, vol. 12, No. 12, 1113-1120 (1999).
Wood et al.: Human DNA repair genes, Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: RNA-mediated gene assembly from DNA arrays. Angew Chem Int Ed Engl. May 7, 2012;51(19):4628-32. doi: 10.1002/anie.201109058.
Wu et al.: Sequence-Specific Capture of Protein-DNA Complexes for Mass Spectrometric Protein Identification PLoS ONE. Oct. 20, 2011, vol. 6, No. 10.
Wu et al.: Specificity of the nick-closing activity of bacteriophage T4 DNA ligase. Gene. 1989;76(2):245-54.
Wu et al.: An improvement of the on-line electrophoretic concentration method for capillary electrophoresis of proteins an experimental factors affecting he concentration effect, Analytical Sciences, vol. 16, 329-331 (Mar. 2000).
Xiong et al.: Chemical gene synthesis: Strategies, softwares, error corrections, and applications. FEMS Microbiol. Rev., 32:522-540, 2008.
Xiong et al.: A simple, rapid, high-fidelity and cost-effective PCR-based two-step DNA synthesis method for long gene sequences. Nucleic Acids Res. 2004, 32(12):e98.
Xiong et al.: Non-polymerase-cycling-assembly-based chemical gene synthesis: Strategies, methods, and progress. Biotechnology Advances. 26(2):121-134, 2008.
Xu et al.: Design of 240,000 orthogonal 25mer DNA barcode probes. PNAS, 106(7):2289-2294, 2009.
Yang et al.: Purification, cloning, and characterization of the CEL I nuclease, Biochemistry, 39(13):3533-35, 2000.
Yazdi et al.: A Rewritable, Random-Access DNA-Based Storage System, Scientific Reports, 5, Article No. 14138, 27 pages, 2015.
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil et al.: Detection of 81 of 81 known mouse Beta-Globin promoter mutations with T4 Endonuclease VII—The EMC Method. Genomics, 32:431-435, 1996.
Young et al.: Two-step total gene synthesis method. Nucleic Acids Res. 32(7):e59, 2004.
Zhang and Seelig. Dynamic DNA nanotechnology using strand-displacement reactions, Nat. Chem., 3(2):103-113, 2011.
Zheleznaya et al.: Nicking endonucleases. Biochemistry (Mosc). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Microfluidic PicoArray synthesis of oligodeoxynucleotides and simultaneous assembling of multiple DNA sequences Nucleic Acids Research, 32(18):5409-5417, 2004.
Zhou et al.: Establishment and application of a loop-mediated isothermal amplification (LAMP) system for detection of cry1Ac transgenic sugarcane Scientific Reports May 9, 2014, vol. 4, No. 4912.
Chervin et al.: Design of T-cell receptor libraries with diverse binding properties to examine adoptive T-cell responses. Gene Therapy. 20(6):634-644 (2012).
Cui et al.: Information Security Technology Based on DNA Computing. International Workshop on Anti-Counterfeiting, Security and Identification (ASID); IEEE Xplore 4 pages (2007).
European Patent Application No. 17872347.4 Extended European Search Report dated Jun. 30, 2020.
European Patent Application No. 17881617.9 European Search Report and Written Opinion dated Jul. 2, 2020.
Goodwin et al.: immunoglobulin heavy chain variable region, partial [*Homo sapiens*], Genbank entry (online). National Institute of Biotechnology Information. (2018) https://www.ncbi.nim.nih.gov/protein/AXA12486.1.
Hopcroft et al.: What is the Young's Modulus of Silicon?. Journal of Microelectromechanical Systems. 19(2):229-238 (2010).
Jaiswal et al.: An architecture for creating collaborative semantically capable scientific data sharing infrastructures. Proceeding

(56) References Cited

OTHER PUBLICATIONS

WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Malecek et al.: Engineering improved T cell receptors using an alanine-scan guided T cell display selection system. Journal of Immunological Methods. Elsevier Science Publishers. 392(1):1-11 (2013).
(Novartis Institutes for Biomedical Research) Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
(Novartis Institutes for Biomedical Research) Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.
PCT/US2019/012218 International Preliminary Report on Patentability dated Jul. 16, 2020.
PCT/US2020/019371 International Search Report and Written Opinion dated Jun. 25, 2020.
PCT/US2020/019986 International Search Report and Written Opinion dated Jul. 29, 2020.
PCT/US2020/019988 International Search Report and Written Opinion dated Jul. 29, 2020.
PubChem Data Sheet Dichloromethane. Printed from website https://pubchem.ncbi.nlm.nih.gov/compound/Dichloromethane (2020).
U.S. Appl. No. 15/151,316 Final Office Action dated Jul. 9, 2020.
U.S. Appl. No. 15/835,342 Final Office Action dated Sep. 8, 2020.
U.S. Appl. No. 16/039,256 Office Action dated Aug. 20, 2020.
U.S. Appl. No. 16/128,372 Office Action dated Oct. 8, 2020.
U.S. Appl. No. 16/384,678 Final Office Action dated Oct. 15, 2020.
U.S. Appl. No. 16/535,777 Final Office Action dated Oct. 20, 2020.
Van der Velde: Thesis. Finding the Strength of Glass. Delft University of Technology. 1-16 (2015).
De Graff et al.: Glucagon-Like Peptide-1 and its Class B G Protein-Coupled Receptors: A Long March to Therapeutic Successes. Pharmacol Rev. 68(4):954-1013 (2016).
Hood et al.: The digital code of DNA. Nature 421.6921:444-448 (2003).
PCT/US2020/019371 International Preliminary Report on Patentability dated Sep. 2, 2021.
PCT/US2020/019986 International Preliminary Report on Patentability dated Sep. 10, 2021.
PCT/US2020/019988 International Preliminary Report on Patentability dated Sep. 10, 2021.
U.S. Appl. No. 15/902,855 Office Action dated Dec. 9, 2021.
U.S. Appl. No. 16/128,372 Office Action dated Dec. 13, 2021.
U.S. Appl. No. 16/712,678 Office Action dated Nov. 26, 2021.
U.S. Appl. No. 16/737,401 Restriction Requirement dated Nov. 15, 2021.
U.S. Appl. No. 16/798,275 Final Office Action dated Aug. 30, 2021.
U.S. Appl. No. 16/802,439 Restriction Requirement dated Oct. 1, 2021.
U.S. Appl. No. 16/854,719 Office Action dated Nov. 24, 2021.
U.S. Appl. No. 16/879,705 Office Action dated Sep. 9, 2021.
U.S. Appl. No. 17/154,906 Office Action dated Nov. 10, 2021.
Wikipedia. Central dogma of molecular biology. URL: https://en.wikipedia.org/wiki/Central_dogma_of_molecular_biology. 9 pages (2021).
Bai. A Novel Human scFv Library with Non-Combinatorial Synthetic CDR Diversity. PLoS One. 10(10):1-18 (2015).
Berg: Biochemistry. 5th ED. New York (2002) 148-149.
Borda et al.: Secret writing by DNA hybridization. Acta Technica Napocensis Electronics and Telecommunications. 50(2):21-24 (2008).
Fernández-Quintero et al.: Characterizing the Diversity of the CDR-H3 Loop Conformational Ensembles in Relationship to Antibody Binding Properties. Front. Immunol. 9:1-11 (2019).
GE Healthcare. AKTA oligopilot plus. Data File 18-114-66 AD ©. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).
Hudson: Matrix Assisted Synthetic Transformations: A Mosaic of Diverse Contributions. Journal of Combinatorial Chemistry. 1(6):403-457 (1999).
Kalva et al.: Gibson Deletion: a novel application of isothermal in vitro recombination. Biological Procedures Online. 20(1):1-10 (2018).
Lebl et al.: Economical Parallel Oligonucleotide and Peptide Synthesizer—Pet Oligator. Int. J. Peptide Res. Ther. 13(1-2):367-376 (2007).
MLAB 2321 Molecular Diagnostics for Clinical Laboratory Science. Mar. 6, 2015.
Momentiv. Technical Data Sheet. Silquest A-1100. Momentiv. 1-6 (2020).
Nucleic acid thermodynamics. Wikipedia. Feb. 4, 2021.
O'Driscoll et al.: Synthetic DNA: The next generation of big data storage. Bioengineered. 4(3):123-125 (2013).
Opposition to European Patent No. 3030682 filed Mar. 3, 2021.
PCT/US2019/032992 International Preliminary Report on Patentability dated Nov. 24, 2020.
PCT/US2019/068435 International Preliminary Report on Patentability dated Jul. 8, 2021.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Ponsel. High Affinity, Developability and Functional Size: The Holy Grail of Combinatorial Antibody Library Generation. Molecules. 16:3675-3700 (2011).
Regep et al.: The H3 loop of antibodies shows unique structural characteristics. Proteins. 85(7):1311-1318 (2017).
Shipman et al.: Molecular recordings by directed CRISPR spacer acquisition. Science. 353(6298):1-16 (2016).
U.S. Appl. No. 15/156,134 Final Office Action dated Aug. 18, 2021.
U.S. Appl. No. 15/156,134 Office Action dated Nov. 25, 2020.
U.S. Appl. No. 15/245,054 Notice of Allowance dated Dec. 14, 2017.
U.S. Appl. No. 15/272,004 Final Office Action dated Mar. 18, 2021.
U.S. Appl. No. 15/619,322 Final Office Action dated Jul. 9, 2021.
U.S. Appl. No. 15/619,322 Office Action dated Nov. 4, 2020.
U.S. Appl. No. 15/835,342 Office Action dated Apr. 16, 2021.
U.S. Appl. No. 15/902,855 Restriction Requirement dated Apr. 6, 2021.
U.S. Appl. No. 15/921,479 Office Action dated Apr. 27, 2021.
U.S. Appl. No. 16/039,256 Final Office Action dated Mar. 30, 2021.
U.S. Appl. No. 16/128,372 Final Office Action dated Mar. 18, 2021.
U.S. Appl. No. 16/535,777 Office Action dated Feb. 8, 2021.
U.S. Appl. No. 16/712,678 Restriction Requirement dated Aug. 25, 2021.
U.S. Appl. No. 16/798,275 Office Action dated Feb. 10, 2021.
U.S. Appl. No. 16/854,719 Restriction Requirement dated Jul. 28, 2021.

(56) References Cited

OTHER PUBLICATIONS

U.S. Appl. No. 17/154,906 Restriction Requirement dated Jul. 26, 2021.
Yazdi et al.: DNA-Based Storage: Trends and Methods. IEEE Transactions on Molecular, Biological and Multi-Scale Communications. IEEE. 1(3):230-248 (2016).

* cited by examiner

Number of Pieces

CFUs (log scale)

Runaway : 10X above median (1480)

Dropout: 10X Below median (14.8)

Complete Dropout: 0 reads in IDX Stats

| Complete Dropouts | Dropout | Runaway |
|---|---|---|
| 191 (0.8% of the pool) | 267 (1.16% of the pool) | 50 (0.217% of the pool) |

BARCODE-BASED NUCLEIC ACID SEQUENCE ASSEMBLY

CROSS-REFERENCE

This application claims the benefit of U.S. Provisional Application No. 62/865,094, filed Jun. 21, 2019, which application is incorporated herein by reference.

SEQUENCE LISTING

The instant application contains a Sequence Listing which has been submitted electronically in ASCII format and is hereby incorporated by reference in its entirety. Said ASCII copy, created on Jul. 20, 2020, is named 44854-783_201_SL.txt and is 1,571 bytes in size.

BACKGROUND

De novo nucleic acid synthesis is a powerful tool for basic biological research and biotechnology applications. While various methods are known for the synthesis of relatively short fragments of nucleic acids on a small scale, these techniques suffer from scalability, automation, speed, accuracy, and cost. Thus, a need remains for efficient methods of variant nucleic acid assembly.

BRIEF SUMMARY

Provided herein are methods for nucleic acid assembly, comprising: (a) providing a first plurality of polynucleotides, wherein each polynucleotide of the first plurality of polynucleotides comprises a first terminal region of sequence homology; (b) providing a second plurality of polynucleotides, wherein each polynucleotide of the second plurality of polynucleotides comprises a second terminal region of sequence homology to the first terminal region of sequence homology; and (c) contacting the first plurality of polynucleotides and the second plurality of polynucleotides with a reaction mixture comprising an exonuclease, an endonuclease, a polymerase, and a ligase to assemble a library of nucleic acids, wherein at least 80% of the nucleic acids are each present in the library in an amount within 2× of a mean frequency for each of the nucleic acids in the library. Further provided herein are methods, wherein the first plurality of polynucleotides comprises up to 100 different sequences. Further provided herein are methods, wherein the second plurality of polynucleotides comprises up to 100 different sequences. Further provided herein are methods, wherein at least 10,000 nucleic acids are assembled. Further provided herein are methods, wherein at least 100,000 nucleic acids are assembled. Further provided herein are methods, wherein each polynucleotide of the first plurality of polynucleotides comprises up to 2500 bases in length. Further provided herein are methods, wherein each polynucleotide of the second plurality of polynucleotides comprises up to 2500 bases in length. Further provided herein are methods, wherein the exonuclease is exonuclease III. Further provided herein are methods, wherein the endonuclease is a flap endonuclease. Further provided herein are methods, wherein the flap endonuclease is flap endonuclease 1, exonuclease 1, XPG, Dna2, or GEN1. Further provided herein are methods, wherein the polymerase comprises 5' to 3' polymerase activity. Further provided herein are methods, wherein the polymerase is a DNA polymerase. Further provided herein are methods, wherein the ligase catalyzes joining of at least two nucleic acids.

Provided herein are methods for nucleic acid assembly, comprising: de novo synthesizing a first nucleic acid comprising in 5' to 3' order: a barcode sequence, a first restriction endonuclease site, a second restriction endonuclease site, and a first hypervariable region sequence; de novo synthesizing a second nucleic acid comprising in 5' to 3' order: a first region of any defined length sequence, a self-cleaving peptide sequence, a first complementary region adjacent to a first variable region sequence, and a first variable region sequence; contacting the first nucleic acid and the second nucleic to generate a third nucleic acid; providing a fourth nucleic acid comprising in 5' to 3' order: a vector sequence, a second complementary region adjacent to a second variable region sequence, a second variable region sequence, a second hypervariable region sequence, the first restriction endonuclease site, and the barcode sequence; contacting the third nucleic acid and the fourth nucleic acid with a restriction endonuclease; and assembling the third nucleic acid and the fourth nucleic acid using a reaction mixture comprising one or more enzymes. Further provided herein are methods, wherein the first restriction endonuclease site or the second restriction endonuclease site is a Type IIS restriction endonuclease (TIIS-RE) site. Further provided herein are methods, wherein the restriction endonuclease is a Type IIS restriction endonuclease. Further provided herein are methods, wherein the reaction mixture comprises a ligase. Further provided herein are methods, wherein the first hypervariable region sequence and the second hypervariable region sequence each comprises a complementary determining region (CDR). Further provided herein are methods, wherein the CDR is CDR3. Further provided herein are methods, wherein the self-cleaving peptide is P2A. Further provided herein are methods, wherein about 100 variants of the first variable region sequence are synthesized. Further provided herein are methods, wherein about 130 variants of the second variable region sequence are synthesized. Further provided herein are methods further comprising amplifying the nucleic acid with a first primer complementary to a first barcode sequence and a second primer wherein at least 99% of the amplicons have no deletions.

Provided herein are methods for nucleic acid assembly, comprising: de novo synthesizing a first nucleic acid comprising a first variable region sequence; de novo synthesizing a second nucleic acid comprising a second variable region sequence; de novo synthesizing a third nucleic acid comprising in 5' to 3' order: a first region of fixed variability sequence, a first region of any defined length sequence, a self-cleaving peptide sequence, a first complementary region adjacent to a first variable region sequence, and a second region of fixed variability sequence; and contacting the first nucleic acid, the second nucleic acid, and the third nucleic acid with a reaction mixture comprising an exonuclease, an endonuclease, a polymerase, and a ligase. Further provided herein are methods, wherein the first variable region sequence or the second variable region sequence is amplified with a hypervariable region sequence. Further provided herein are methods, wherein the hypervariable region sequence comprises a CDR. Further provided herein are methods, wherein the CDR is CDR3. Further provided herein are methods further comprising contacting with sequences comprising one or more regions of any defined length. Further provided herein are methods, wherein about 100 variants of the first variable region sequence are synthesized. Further provided herein are methods, wherein about 130 variants of the second variable region sequence are synthesized. Further provided herein are methods, wherein the self-cleaving peptide is P2A. Further provided herein are methods, wherein the exonuclease is exonuclease III. Further provided herein are methods, wherein the endonuclease is a flap endonuclease. Further provided herein are methods, wherein the flap endonuclease is flap endonuclease 1, exonuclease 1, XPG, Dna2, or GEN1. Further provided herein are methods, wherein the polymerase comprises 5' to 3' polymerase activity. Further provided herein are methods, wherein the polymerase is a DNA polymerase Further provided herein are methods, wherein the ligase catalyzes joining of at least two nucleic acids. Further provided herein are methods, wherein the first region of fixed variability sequence and the second region of fixed variability sequence are each about 10 to about 100 base pairs. Further provided herein are methods, wherein the first region of fixed variability sequence and the second region of fixed variability sequence are each about 40 base pairs.

Provided herein are methods for nucleic acid assembly, comprising: providing a first nucleic acid comprising a first region of any defined length sequence; providing a second nucleic acid comprising a second region of any defined length sequence; assembling a third nucleic acid comprising in 5' to 3' order: a first complementary region adjacent to a first variable region sequence, a first variable region sequence, and a first hypervariable region sequence; assembling a fourth nucleic acid comprising in 5' to 3' order: a second complementary region adjacent to a second variable region sequence, a second variable region sequence, and a second hypervariable region sequence; contacting the first nucleic acid, the second nucleic acid, the third nucleic acid, and the fourth nucleic acid; and amplifying the resulting product. Further provided herein are methods further comprising an error correction step. Further provided herein are methods further comprising contacting a reaction mixture comprising an exonuclease, an endonuclease, a polymerase, and a ligase during step of contacting the first nucleic acid, the second nucleic acid, the third nucleic acid, and the fourth nucleic acid. Further provided herein are methods, wherein the first hypervariable region sequence and the second hypervariable region sequence each comprises a complementary Further provided herein are methods, wherein the first nucleic acid comprises about 300 to about 700 base pairs. Further provided herein are methods, wherein the second nucleic acid comprises about 200 to about 600 base pairs. Further provided herein are methods, wherein the third nucleic acid comprises about 200 to about 600 base pairs. Further provided herein are methods, wherein the fourth nucleic acid comprises about 200 to about 600 base pairs.

Provided herein are methods for nucleic acid assembly, comprising: de novo synthesizing: a first nucleic acid comprising in 5' to 3' order: a first complementary region adjacent to a first variable region sequence and a first variable region sequence; a second nucleic acid comprising in 5' to 3' order: a first region of fixed variability sequence and a first hypervariable region sequence; a third nucleic acid comprising a second variable region sequence; a fourth nucleic acid comprising in 5' to 3' order: a restriction endonuclease site and a second region of fixed variability sequence; and a fifth nucleic acid comprising in 5' to 3' order: the second region of fixed variability sequence, a second hypervariable region sequence, and a variable constant region sequence; contacting the first nucleic acid, the second nucleic acid, the third nucleic acid, the fourth nucleic acid, and the fifth nucleic acid with a reaction mixture comprising an exonuclease, an endonuclease, a polymerase, and a ligase; and cloning a construct of step (b) into a vector sequence. Further provided herein are methods, wherein the first hypervariable region sequence and the second hypervariable region sequence each comprises a complementary determining region (CDR). Further provided herein are methods, wherein the CDR is CDR3. Further provided herein are methods further comprising contacting one or more variable constant regions. Further provided herein are methods, wherein the exonuclease is exonuclease III. Further provided herein are methods, wherein the flap endonuclease is flap endonuclease 1, exonuclease 1, XPG, Dna2, or GEN1. Further provided herein are methods, wherein the polymerase comprises 5' to 3' polymerase activity.

Provided herein are methods for nucleic acid assembly, comprising: providing a first nucleic acid comprising in 5' to 3' order: a first complementary region adjacent to a first variable region sequence and a first variable region sequence; providing a second nucleic acid sequence comprising in 5' to 3' order: a first region of fixed variability sequence, a first hypervariable region sequence, a restriction endonuclease site, a second hypervariable region sequence, and a universal primer; amplifying the first nucleic acid and the second nucleic acid to generate a third nucleic acid; providing a vector sequence comprising the first complementary region adjacent to the first variable region sequence and a first region of any defined length sequence; contacting the third nucleic acid and the vector sequence; contacting a fourth nucleic acid comprising in 5' to 3' order: a self-cleaving peptide sequence, a second complementary region adjacent to a second variable region sequence, and a second variable region sequence. Further provided herein are methods, wherein the first hypervariable region sequence and the second hypervariable region sequence each comprises a complementary determining region (CDR). Further provided herein are methods, wherein the CDR is CDR3. Further provided herein are methods, wherein the self-cleaving peptide is P2A.

Provided herein are methods for nucleic acid assembly, comprising: de novo synthesizing: a first nucleic acid comprising a first complementary region adjacent to a first variable region sequence and a first variable region sequence; a second nucleic acid comprising a first hypervariable region sequence; a third nucleic acid comprising a second variable region sequence; a fourth nucleic acid comprising in 5' to 3' order: a first hypervariable region sequence, a first region of fixed variability, and a barcode; amplifying the first nucleic acid and the second nucleic acid to generate a fifth nucleic acid; amplifying the third nucleic acid and the fourth nucleic acid to generate a fifth nucleic acid; contacting the fifth nucleic acid and the sixth nucleic acid with a reaction mixture comprising an exonuclease, an endonuclease, a polymerase, and a ligase to generate a seventh nucleic acid; circularizing the seventh nucleic acid; sequencing and identifying the seventh nucleic acid using the barcode; amplifying the seventh nucleic acid; and assembling the seventh nucleic acid in a vector using the reaction mixture comprising the exonuclease, the endonuclease, the polymerase, and the ligase. Further provided herein are methods, wherein the first variable region sequence or the second variable region sequence is amplified with a hypervariable region sequence. Further provided herein are methods, wherein the hypervariable region sequence comprises a CDR. Further provided herein are methods, wherein the CDR is CDR3. Further provided herein are methods further comprising contacting with sequences comprising one or more regions of any defined length. Further provided herein are methods, wherein about 100 variants of the first variable region sequence are synthesized. Further provided herein are methods, wherein about 130 variants of the second variable region sequence are synthesized. Further provided herein are methods, wherein the self-cleaving peptide is P2A. Further provided herein are methods, wherein the exonuclease is exonuclease III. Further provided herein are methods, wherein the endonuclease is a flap endonuclease. Further provided herein are methods, wherein the flap endonuclease is flap endonuclease 1, exonuclease 1, XPG, Dna2, or GEN1. Further provided herein are methods, wherein the polymerase comprises 5' to 3' polymerase activity. Further provided herein are methods, wherein the polymerase is a DNA polymerase. Further provided herein are methods, wherein the ligase catalyzes joining of at least two nucleic acids. Further provided herein are methods, wherein the first region of fixed variability sequence and the second region of fixed variability sequence are each about 10 to about 100 base pairs. Further provided herein are methods, wherein the first region of fixed variability sequence and the second region of fixed variability sequence are each about 40 base pairs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 12E is a graph of colony forming units (CFUs) for assembly of zero to six DNA fragments at once using an enzymatic assembly method.

DETAILED DESCRIPTION

Definitions

Figure 1A:
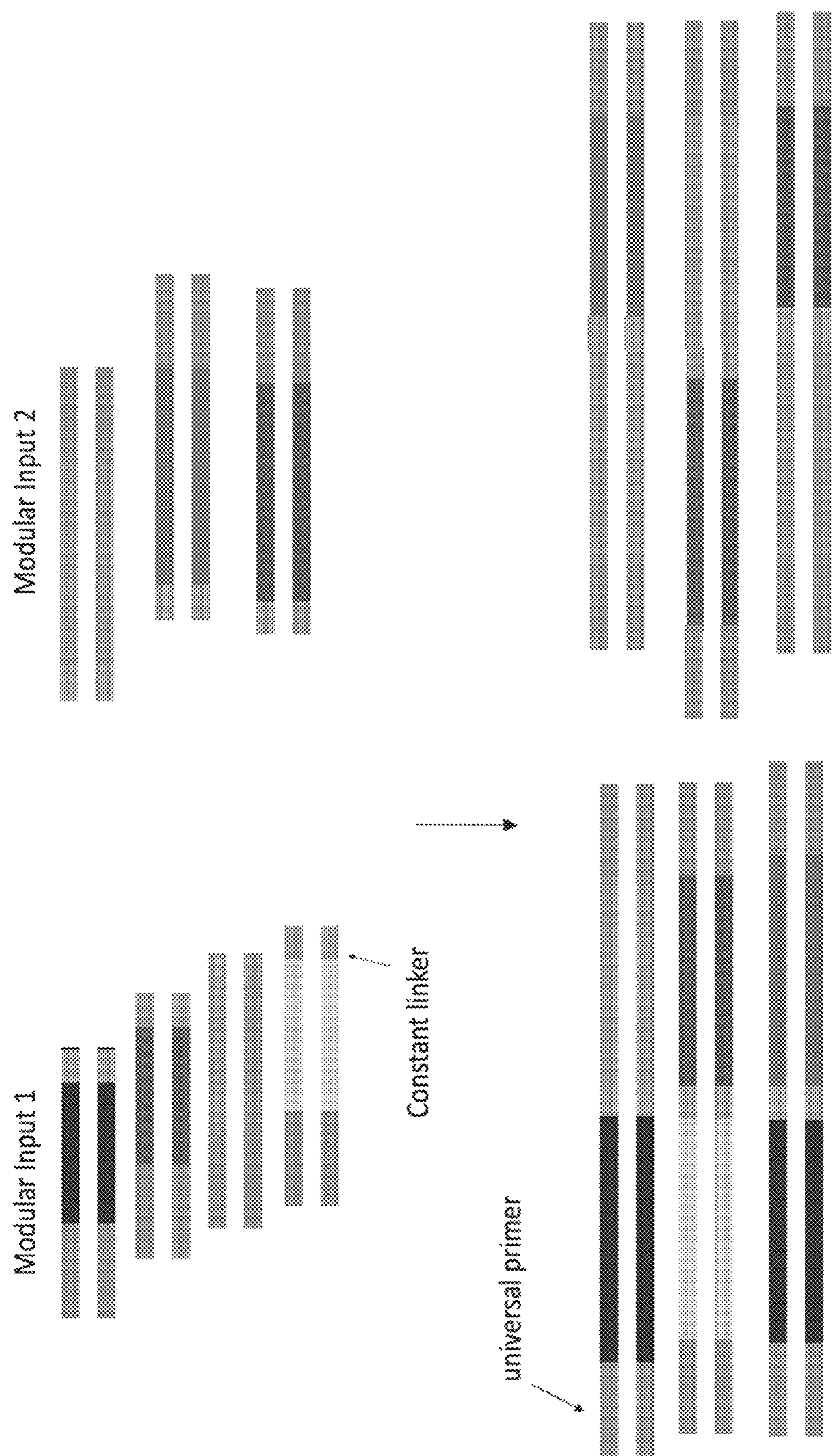
FIG. 1A illustrates a schematic of a combinatorial assembly with modular inputs (2 inputs or "domains" shown for illustration only) and pools connected by a unique linker region.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred to herein may comprise at least one region encoding for exon sequences without an intervening intron sequence in the genomic equivalent sequence.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Primers referred to in the exemplary workflows mentioned herein as "universal primers," are short polynucleotides that recognize a primer binding site common to multiple DNA fragments. However, these workflows are not limited to only use of universal primers, and fragment-specific primers may be incorporated in addition or alternatively. In addition, while exemplary workflows described herein refer to assembly of gene fragments, they are not limited as such and are applicable to the assembly of longer nucleic acids in general.

Sequence Assembly

Described herein are methods and compositions for the assembly of nucleic acid sequences. Assembly of such sequences may in some cases be challenging due to specific properties of the assembly fragments, such as GC content, repeating regions, and secondary structure. Additionally, assembly of libraries of such sequences may be assembled in parallel, with members of the library possessing regions of high variability across members. Such parallel assembly of fragments is challenging due to the presence of highly variable regions across members of the library for such fragments. Moreover, assembly may result in errors, such as incorrectly assembled nucleic acids. Nucleic acids comprising variable regions may include nucleic acids encoding for genes (such as proteins or antibodies), or non-coding nucleic acids. In some instances, a nucleic acid assembled herein comprises a region encoding for an immunoglobulin or fragment thereof. Assembly of libraries comprising nucleic acids of high variability may be accomplished by the methods described herein. Such methods in some instances comprise PCR/PCA-based overlap assembly, ligation, cloning with vectors, flapase-based assembly, exonuclease-based assembly, or other assembly method. Multiple methods are in some instances combined to generate a library of nucleic acids. Such methods are executed in any order, and in some instances comprise intervening purification or other steps. In some instances, assembled nucleic acids are amplified from a pool of partially and fully assembled nucleic acids to generate a library. In some instances, correctly assembled nucleic acids are amplified from a pool comprising correctly assembled and incorrectly assembled nucleic acids to generate a library.

Figure 1B:
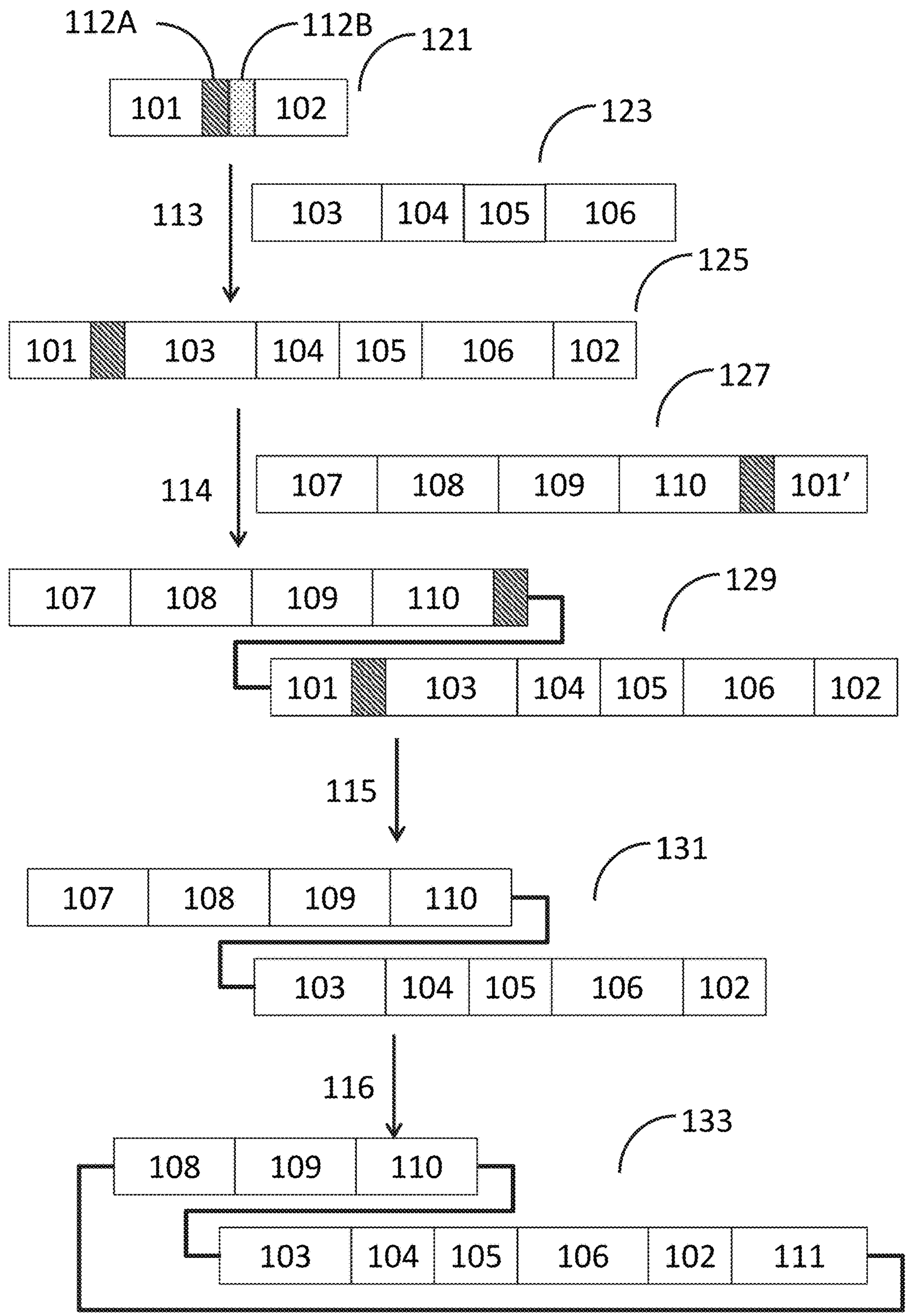
FIG. 1B illustrates a schematic of paired variant assembly using a Type IIS exposed barcode.

An exemplary process for sequence assembly using a barcode is seen in FIG. 1B. Gene fragment 121 is synthesized and comprises a barcode 101 followed by a first restriction endonuclease site 112A, a second restriction endonuclease site 112B, and a first hypervariable region 102. In some instances, the first hypervariable region comprises a CDR. In some instances, the CDR is CDR3. In some instances, the first restriction endonuclease site or the second restriction endonuclease site is a Type IIS restriction endonuclease (TIIS-RE) site. In some instances, the first restriction endonuclease site and the second restriction endonuclease site are different TIIS-RE sites. Gene fragment 123 is synthesized and comprises a first region of any defined length 103 followed by a self-cleaving peptide sequence 104, a first complementary region adjacent to a first variable region 105, and a first variable region 106. In some instances, the self-cleaving peptide sequence is P2A. In some instances, the number of first variable regions synthesized is about 100. In some instances, the number of first variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. Gene fragment 121 is combined 113 with gene fragment 123. The resulting fragment 125 comprises the barcode 101 followed by the restriction endonuclease site 112A, the first region of any defined length 103, the cleaving peptide sequence 104, the first complementary region adjacent to a first variable region 105, the first variable region 106, and the first hypervariable region 102. Gene fragment 127 is synthesized and comprises a vector sequence 107 followed by a second complementary region adjacent to a second variable region 108, a second variable region 109, a second hypervariable region 110, a TIIS-RE site 112A, and a second barcode 101'. In some instances, the number of second variable regions synthesized is about 130. In some instances, the number of second variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. Gene fragment 125 is then PCR amplified 114 with gene fragment 127. The resulting fragment 129 comprises the vector sequence 107 followed by the second complementary region adjacent to a second variable region 108, the second variable region 109, the second hypervariable region 110, the TIIS-RE site 112A, the barcode 101, the TIIS-RE site 112A, the first region of any defined length 103, the cleaving peptide sequence 104, the first complementary region adjacent to a first variable region 105, the first variable region 106, and the first hypervariable region 102. Gene fragment 129 is then cloned and the TIIS restriction endonucleases cut at the TIIS-RE sites to remove the barcode 101. The resulting fragment 131 comprises the vector sequence 107 followed by the second complementary region adjacent to a second variable region 108, the second variable region 109, the second hypervariable region 110, the first region of any defined length 103, the cleaving peptide sequence 104, the first complementary region adjacent to a first variable region 105, the first variable region 106, and the first hypervariable region 102. Gene fragment 131 is then cloned 116 to generate final construct 133. The final construct 133 comprises the second complementary region adjacent to a second variable region 108, the second variable region 109, the second hypervariable region 110, the first region of any defined length 103, the cleaving peptide sequence 104, the first complementary region adjacent to a first variable region 105, the first variable region 106, the first hypervariable region 102, and a first variable constant segment 111. In some instances, a number of final constructs generated is about 1000. In some instances, the number of gene fragments synthesized is about 50, 100, 250, 500, 1000, 2000, 3000, 5000, 7500, 10,000, or about 20,000. In some instances, the number of first variable regions synthesized is 100-5000, 200-5000, 500-5000, 100-2000, 250-1500, 750-1250, 2000-7500, 900-10,000, 3000-10,000, 750-5000, 500-2000, or 500-3000. In some instances, the number of final constructs synthesized is about 5000, 10,000, 25,000, 500,000, 100,000, 200,000, 300,000, 500,000, 750,000, 1,000,000, or about 5,000,000. In some instances, the number of final constructs synthesized is at least 5000, 10,000, 25,000, 500,000, 100,000, 200,000, 300,000, 500,000, 750,000, 1,000,000, or at least 5,000,000.

Figure 2:
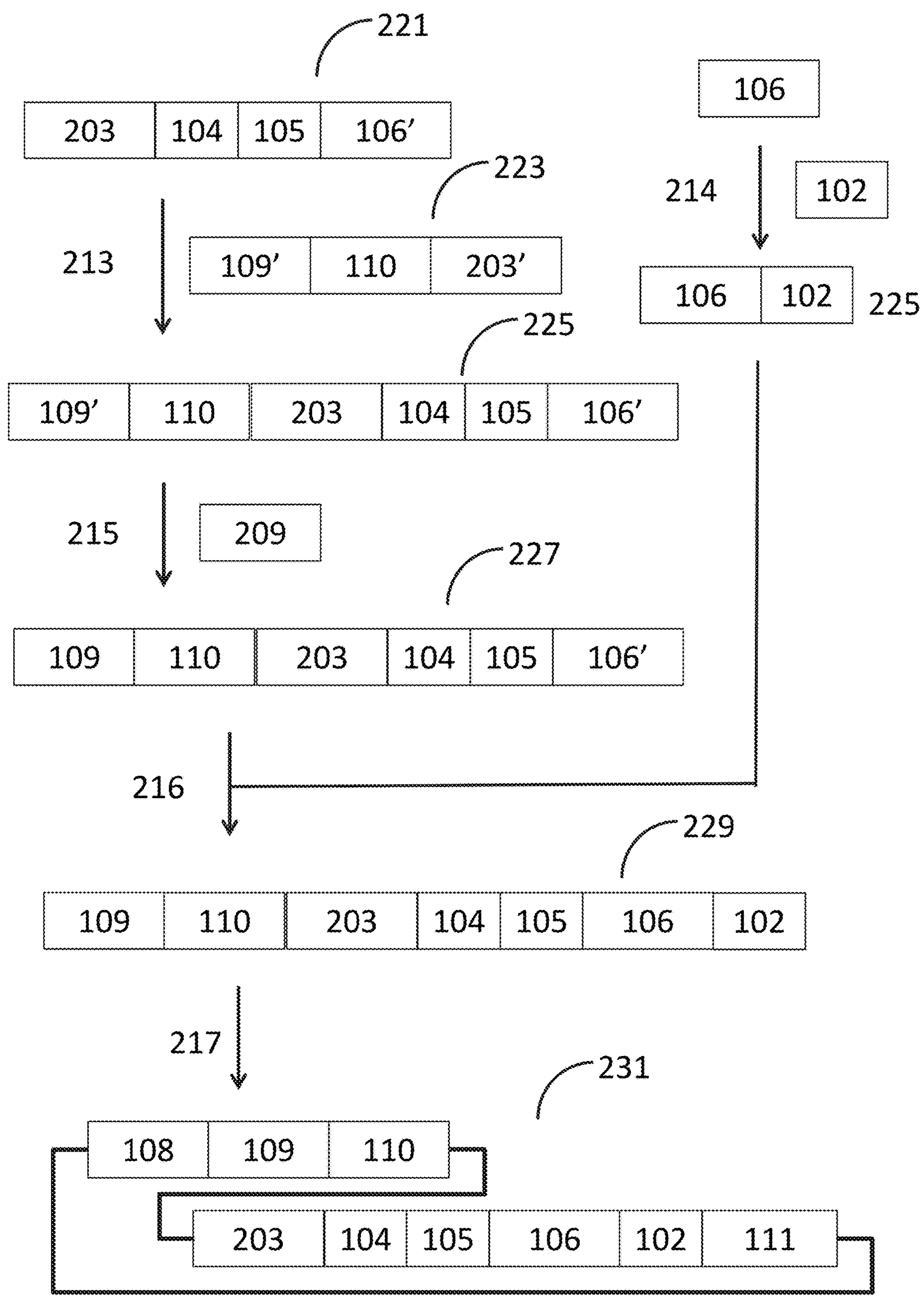
FIG. 2 illustrates a schematic of paired variant assembly using paired homology.

An exemplary process for sequence assembly is seen in FIG. 2. Gene fragment 221 is synthesized and comprises a second region of any defined length 203, a self-cleaving peptide sequence 104, a first complementary region adjacent to a first variable region 105, and a first region of fixed variability 106'. In some instances, the first region of fixed variability is at least 15, 20, 25, 30, 35, 40, 45, 50, or more than 50 bases in length. In some instances, the first region of fixed variability is about 15, 20, 25, 30, 35, 40, 45, 50, 55, 60 or about 65 bases in length. In some instances, the self-cleaving peptide sequence is P2A. Gene fragment 223 is synthesized and comprises a second region of fixed variability 109' followed by the second hypervariable region 110 and a region 203' that is homologous to the second region of any defined length 203. In some instances, the second hypervariable region comprises a CDR. In some instances, the CDR is CDR3. Gene fragment 221 is PCR amplified 213 with gene fragment 223 to generate gene fragment 225. Gene fragment 225 comprises segment 109', the second hypervariable region 110, the second region of any defined length 203, the self-cleaving peptide sequence 104, the first complementary region adjacent to a first variable region 105, and the first region of fixed variability 106'. Gene fragment 225 and gene fragment 209 are subject to enzymatic based assembly and PCR amplified 215 to generate gene fragment 227. Gene fragment 227 comprises the second variable region 109 followed by the second hypervariable region 110, the second region of any defined length 203, the self-cleaving peptide sequence 104, the first complementary region adjacent to a first variable region 105, and the first region of fixed variability 106'. In a separate reaction, a first variable region 106 is synthesized homologous to the first region of fixed variability 106'. The first variable region 106 is amplified 214 with the first hypervariable region 102 to generate gene fragment 225 comprising the first variable region 106 followed by the first hypervariable region 102. Gene fragment 225 and gene fragment 227 are then combined and subject to enzymatic based assembly 216 to generate gene fragment 229. Gene fragment 229 comprises the second variable region 109 followed by the second hypervariable region 110, the second region of any defined length 203, the self-cleaving peptide sequence 104, the first complementary region adjacent to a first variable region 105, the first variable region 106, and the first hypervariable region 102. Gene fragment 229 is cloned 217 into a vector to generate final construct 231. Construct 231 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, and the first variable constant segment 111. In some instances, the number of first variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of second variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of gene fragments synthesized is about 50, 100, 250, 500, 1000, 2000, 3000, 5000, 7500, 10,000, or about 20,000. In some instances, the number of first variable regions synthesized is 100-5000, 200-5000, 500-5000, 100-2000, 250-1500, 750-1250, 2000-7500, 900-10,000, 3000-10,000, 750-5000, 500-2000, or 500-3000.

Figure 3:
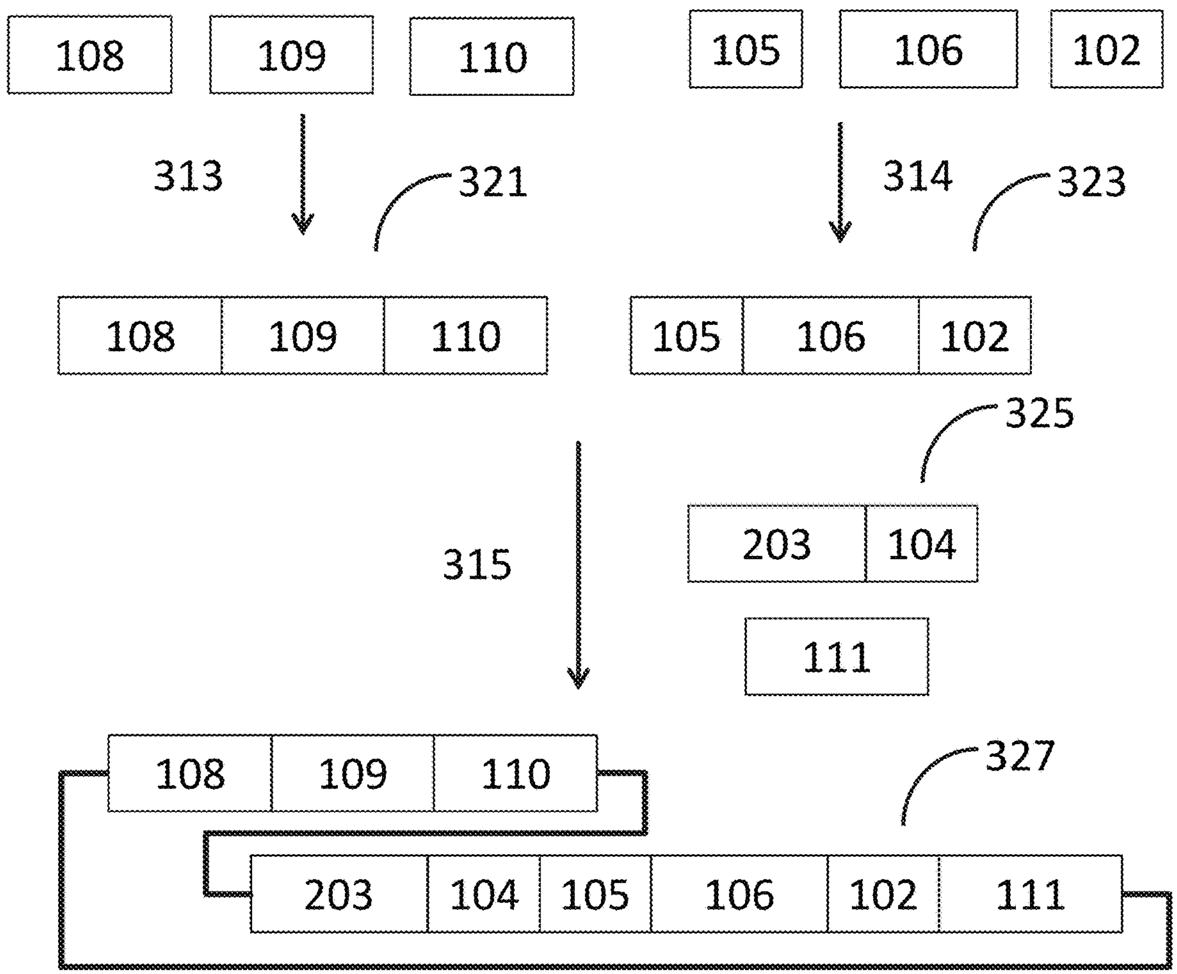
FIG. 3 illustrates a schematic of de novo synthesis of variant nucleic acids, such as those encoding for immunoglobulins or fragments thereof.

An exemplary de novo synthesis method is seen in FIG. 3. A first complementary region adjacent to a first variable region 105, a first variable region 106, and a first hypervariable region 102 are synthesized and then subject to polymerase cycling assembly (PCA) 314 to generate gene fragment 323. Gene fragment 323 comprises the first complementary region adjacent to a first variable region 105 followed by the first variable region 106 and the first hypervariable region 102. In some instances, the first hypervariable region comprises a CDR. In some instances, the CDR is CDR3. A second complementary region adjacent to a second variable region 108, a second variable region 109, and a second hypervariable region 110 are synthesized and subject to assembly PCR or PCA 313 to generate gene fragment 321. In some instances, the second hypervariable region comprises a CDR. In some instances, the CDR is CDR3. Gene fragment 321 comprises the second complementary region adjacent to a second variable region 108 followed by the second variable region 109 and the second hypervariable region 110. Clones of gene fragment 325 comprising a second region of any defined length 203 followed by a self-cleaving peptide sequence 104 and the first variable constant segment 111 are synthesized. Each gene fragment 321, 323, and 325 are synthesized in individual wells and PCR amplified. Gene fragment 325 and the first variable constant segment 111 are added to gene fragment 321 and gene fragment 323 to generate gene fragment 327 followed by PCR. In some instances, an error correction reaction is performed. Gene fragment 327 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, and the first variable constant segment 111. Gene fragment 327 is then cloned and subject to next generation sequencing. In some instances, the number of first variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of second variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of gene fragments synthesized is about 50, 100, 250, 500, 1000, 2000, 3000, 5000, 7500, 10,000, or about 20,000. In some instances, the number of first variable regions synthesized is 100-5000, 200-5000, 500-5000, 100-2000, 250-1500, 750-1250, 2000-7500, 900-10,000, 3000-10,000, 750-5000, 500-2000, or 500-3000.

Figure 4:
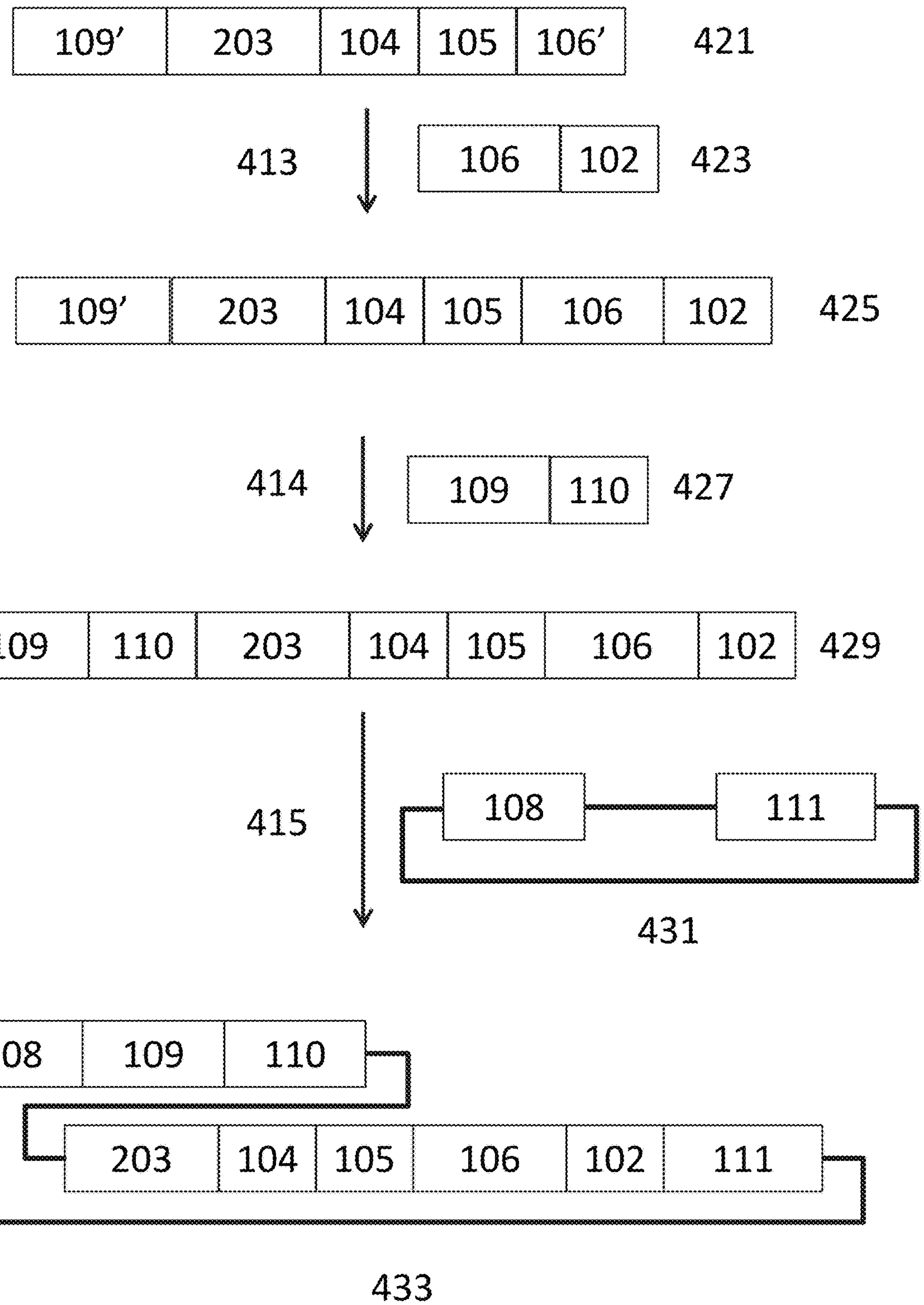
FIG. 4 illustrates a schematic of paired variant assembly using paired homology into a vector.

Provided herein are methods for paired variant assembly using paired homology. An exemplary process is seen in FIG. 4. Gene fragment 421 is synthesized comprising a second region of fixed variability 109' followed by the second region of any defined length 203, the self-cleaving peptide sequence 104, the first complementary region adjacent to a first variable region 105, and the first region of fixed variability 106'. In some instances, the base pair region complementary to the second variable region is at least 15, 20, 25, 30, 35, 40, 45, 50, or more than 50 bases in length. In some instances, the base pair region complementary to the second variable region is about 15, 20, 25, 30, 35, 40, 45, 50, 55, 60 or about 65 bases in length. In some instances, about 130 variants comprising the sequence homologous to the first hypervariable region, the second region of any defined length, the self-cleaving peptide sequence, the first complementary region adjacent to a first variable region, and the region of fixed variability are synthesized. In some instances, the first hypervariable region comprises a CDR. In some instances, the CDR is CDR3. Gene fragment 421 is combined 413 with gene fragment 423 that comprises the first variable region 106 and the first hypervariable region 102 to generate gene fragment 425. In some instances, about 100 variants comprising the first variable segment and the first hypervariable region are synthesized. Gene fragment 425 comprises the second region of fixed variability 109' followed by the second region of any defined length 203, a self-cleaving peptide sequence 104, the first complementary region adjacent to a first variable region 105, the first variable region 106, and the first hypervariable region 102. Gene fragment 425 is then combined 414 with gene fragment 427 comprising the second variable region 109 and the second hypervariable region 110 to generate gene fragment 429. In some instances, about 130 variants comprising the second variable region and the second hypervariable region are synthesized. In some instances, the second hypervariable region comprises a CDR. In some instances, the CDR is CDR3. Gene fragment 429 comprises the second variable region 109, the second hypervariable region 110, the second region of any defined length 203, a self-cleaving peptide sequence 104, the first complementary region adjacent to a first variable region 105, the first variable region 106, and the first hypervariable region 102. Gene fragment 429 is then pooled and cloned 415 into a destination vector 431. The destination vector 431 comprises the second complementary region adjacent to a second variable region 108 and the first variable constant segment 111. The resulting construct 433 comprises the second complementary region adjacent to a second variable region 108 followed by the second variable region 109, the second hypervariable region 110, the second region of any defined length 203, a self-cleaving peptide sequence 104, the first complementary region adjacent to a first variable region 105, the first variable region 106, and the first hypervariable region 102, and the first variable constant segment 111.

Figure 5A:
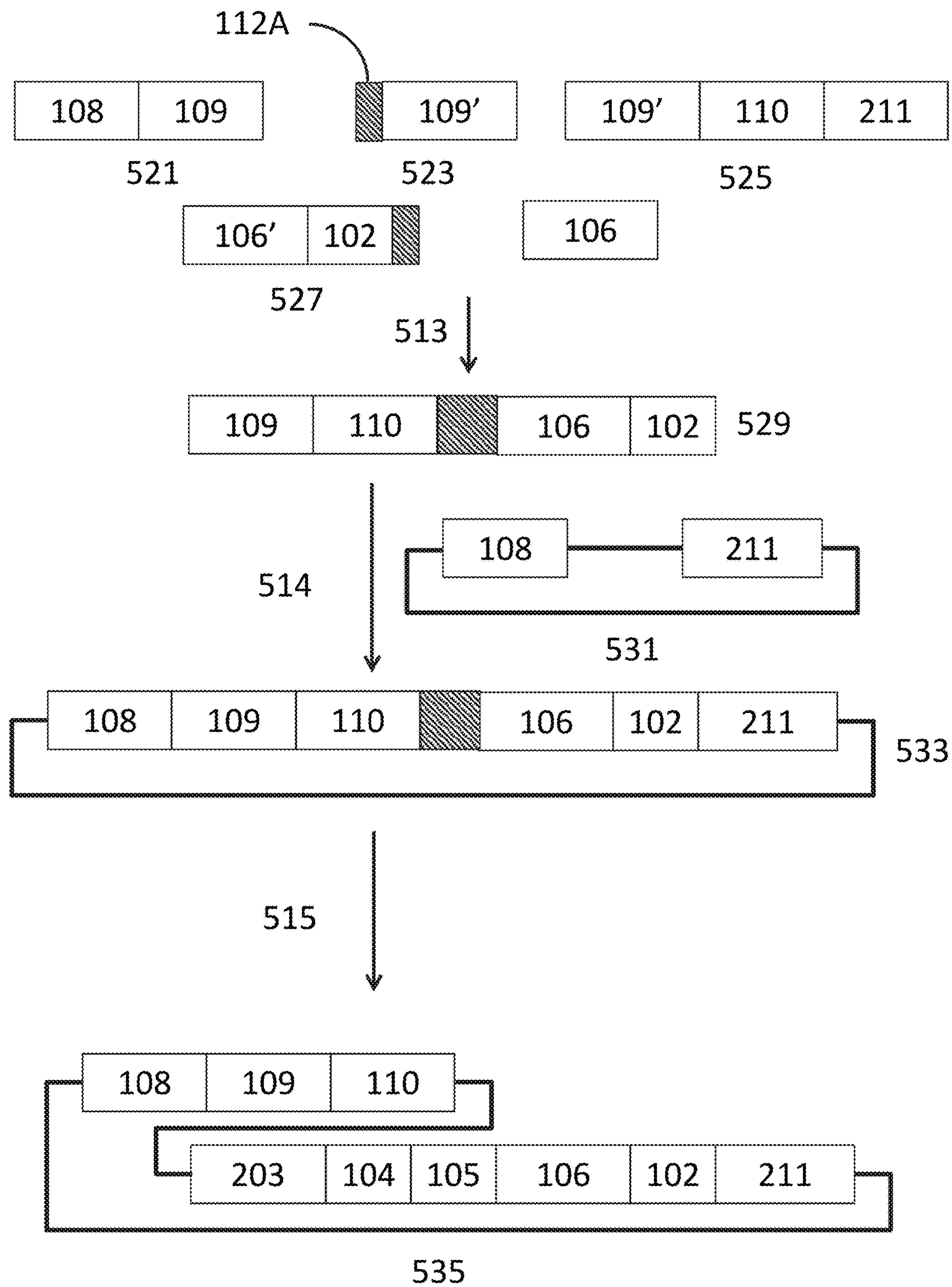
FIG. 5A illustrates a schematic paired variant assembly using Type IIS into a vector.

An exemplary process for sequence assembly is seen in FIG. 5A. Gene fragment 521 is synthesized and comprises the second complementary region adjacent to a second variable region 108 and the second variable region 109. Gene fragment 523 is synthesized and comprises the first restriction endonuclease site 112A followed by the second region of fixed variability 109'. In some instances, second region of fixed variability is at least 15, 20, 25, 30, 35, 40, 45, 50, or more than 50 bases in length. In some instances, the second region of fixed variability is about 15, 20, 25, 30, 35, 40, 45, 50, 55, 60 or about 65 bases in length. In some instances, second region of fixed variability is 10-60, 10-40, 15-60, 20-60, 20-80, 30-50, 20-45, 35-55, 40-80, or 50-80. Gene fragment 525 is synthesized and comprises the second region of fixed variability 109' followed by the second hypervariable region 110 and a second variable constant segment 211. Gene fragment 527 is synthesized and comprises the first region of fixed variability 106' followed by the first hypervariable region 102 and the first restriction endonuclease site 112A. In some instances, the first hypervariable region comprises a CDR. In some instances, the second hypervariable region comprises a CDR. In some instances, the CDR is CDR3. In some instances, the restriction endonuclease site is a TIIS-RE site. Gene fragments 521, 523, 525, 527, and the first variable region 106 are pooled and PCR amplified 513 in order to add the first hypervariable region 102 and the second hypervariable region 110. The resulting gene fragment 529 comprises the second variable region 109 followed by the second hypervariable region 110, the first restriction endonuclease site 112A, the first variable region 106, and the first hypervariable region 102. Gene fragment 529 and destination vector 531 comprising the second complementary region adjacent to a second variable region 108 and the second variable constant segment 211 are then subjected to flap endonuclease mediated nucleic acid assembly 514 to generate gene fragment 533. Gene fragment 533 comprises the second complementary region adjacent to a second variable region 108 followed by the second variable region 109, the second hypervariable region 110, the first restriction endonuclease site 112A, the first variable region 106, the first hypervariable region 102, and the second variable constant segment 211. Gene fragment 533 is then subjected to Golden Gate Assembly 515 to insert the second region of any defined length 203 to generate final construct 535. Final construct 535 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, and the second variable constant segment 211. A number of final constructs generated, in some instances, is about 10000. In some instances, the number of first variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of second variable regions synthesized is about 50, 100, 150, 200, 250, 300, 500, 1000, or about 2000. In some instances, the number of first variable regions synthesized is 10-100, 20-1000, 50-1000, 100-1000, 25-500, 75-125, 200-2000, 150-2000, 300-5000, 50-5000, 1000-5000, or 50-300. In some instances, the number of final constructs synthesized is about 5000, 10,000, 25,000, 500,000, 100,000, 200,000, 300,000, 500,000, 750,000, 1,000,000, or about 5,000,000. In some instances, the number of final constructs synthesized is at least 5000, 10,000, 25,000, 500,000, 100,000, 200,000, 300,000, 500,000, 750,000, 1,000,000, or at least 5,000,000. In some instances, the number of first variable regions synthesized is 1000-50,000, 2900-50,000, 5000-50,000, 1000-20,000, 2500-15,000, 7500-12,500, 20,000-75,000, 9000-100,000, 30,000-100,000, 7500-50,000, 5000-20,000, or 5000-30,000.

Figure 5B:
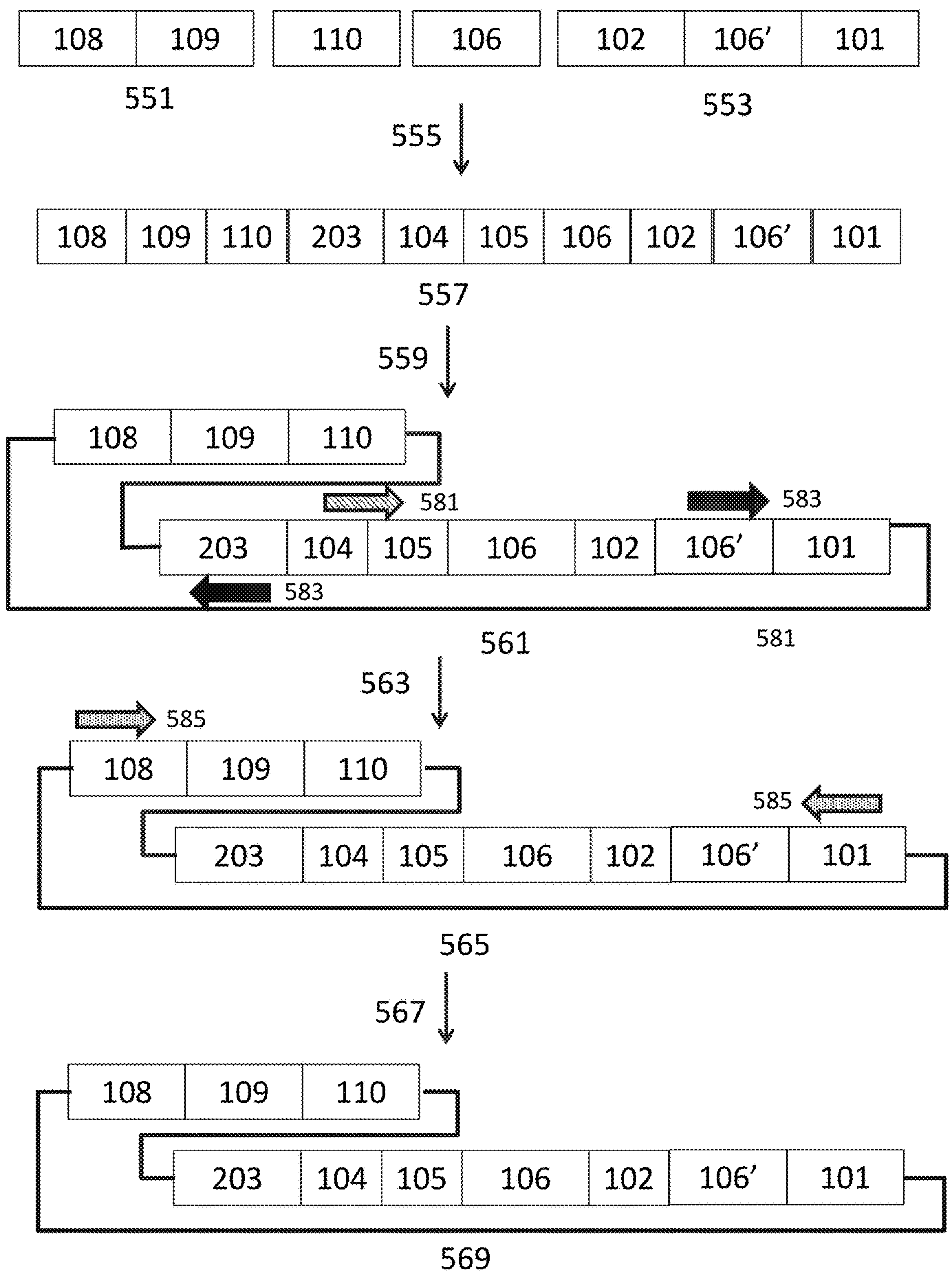
FIG. 5B illustrates a schematic of nucleic acid assembly using paired barcodes and dial out PCR.

An exemplary process for sequence assembly is seen in FIG. 5B. Gene fragment 551 is synthesized and comprises the second complementary region adjacent to a second variable region 108 and the second variable region 109. Gene fragment comprising the second hypervariable region 110 is synthesized. Gene fragment comprising the first variable region 106 is synthesized. Gene fragment 553 comprising a first hypervariable region 102 followed by the first region of fixed variability 106' and the barcode 101. A first combinatorial library of gene fragment 551 and the second hypervariable region 110 are generated using PCR. A second combinatorial library of gene fragment 553 and the first variable region 106 are generated using PCR. The first combinatorial library and the second combinatorial library are assembled using enzymatic based assembly 555 to generate fragment 559. Gene fragment 557 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, the first region of fixed variability 106', and the barcode 101. In some instances, gene fragment 559 comprises a region of a fixed number of base pairs. The number of base pairs, in some instances, is at least or about 5, 10, 15, 20, 25, 30, 35, 40, 45, 50, or more than 50 base pairs. Gene fragment 557 is circularized 559 to generate gene fragment 561. Gene fragment 561 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, the first region of fixed variability 106', and the barcode 101. The first variable region and the first hypervariable region may comprise varying lengths. In some instances, the length of the first variable region and the first hypervariable region is at least or about 15, 20, 25, 30, 35, 40, 45, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or more than 700 bases in length. In some instances, the length of the first variable region and the first hypervariable region is in a range of about 10-1000, 50-900, 100-800, or 200-600 base pairs. The second variable region and the second hypervariable region may comprise varying lengths. In some instances, the length of the second variable region and the second hypervariable region is at least or about 15, 20, 25, 30, 35, 40, 45, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, or more than 700 bases in length. In some instances, the length of the second variable region and the second hypervariable region is in a range of about 10-1000, 50-900, 100-800, or 200-600 base pairs. In some instances, the second region of any defined length, the self-cleaving peptide sequence, and the first complementary region adjacent to a first variable region comprise varying lengths. In some instances, the length of the second region of any defined length, the self-cleaving peptide sequence, and the first complementary region adjacent to a first variable region is at least or about 15, 20, 25, 30, 35, 40, 45, 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 1000, or more than 1000 bases in length. In some instances, the length of the second region of any defined length, the self-cleaving peptide sequence, and the first complementary region adjacent to a first variable region is in a range of about 10-1000, 50-900, 100-800, or 200-600 base pairs. In some instances, the first region of fixed variability comprises at least or about 15, 20, 25, 30, 35, 40, 45, 50, 60, 70, 80, 90, 100, or more than 100 base pairs. In some instances, the barcode comprises at least or about 1, 5, 10, 15, 20, 25, 30, 35, 40, 45, 50, or more than 50 base pairs. Gene fragment 561 is then sequenced with primers 581 and 583 and samples are identified having the barcode 563 to generate gene fragment 565. Gene fragment 565 is then subject to dial out PCR and enzymatic based assembly 567 into a final vector 569.

Figure 6:
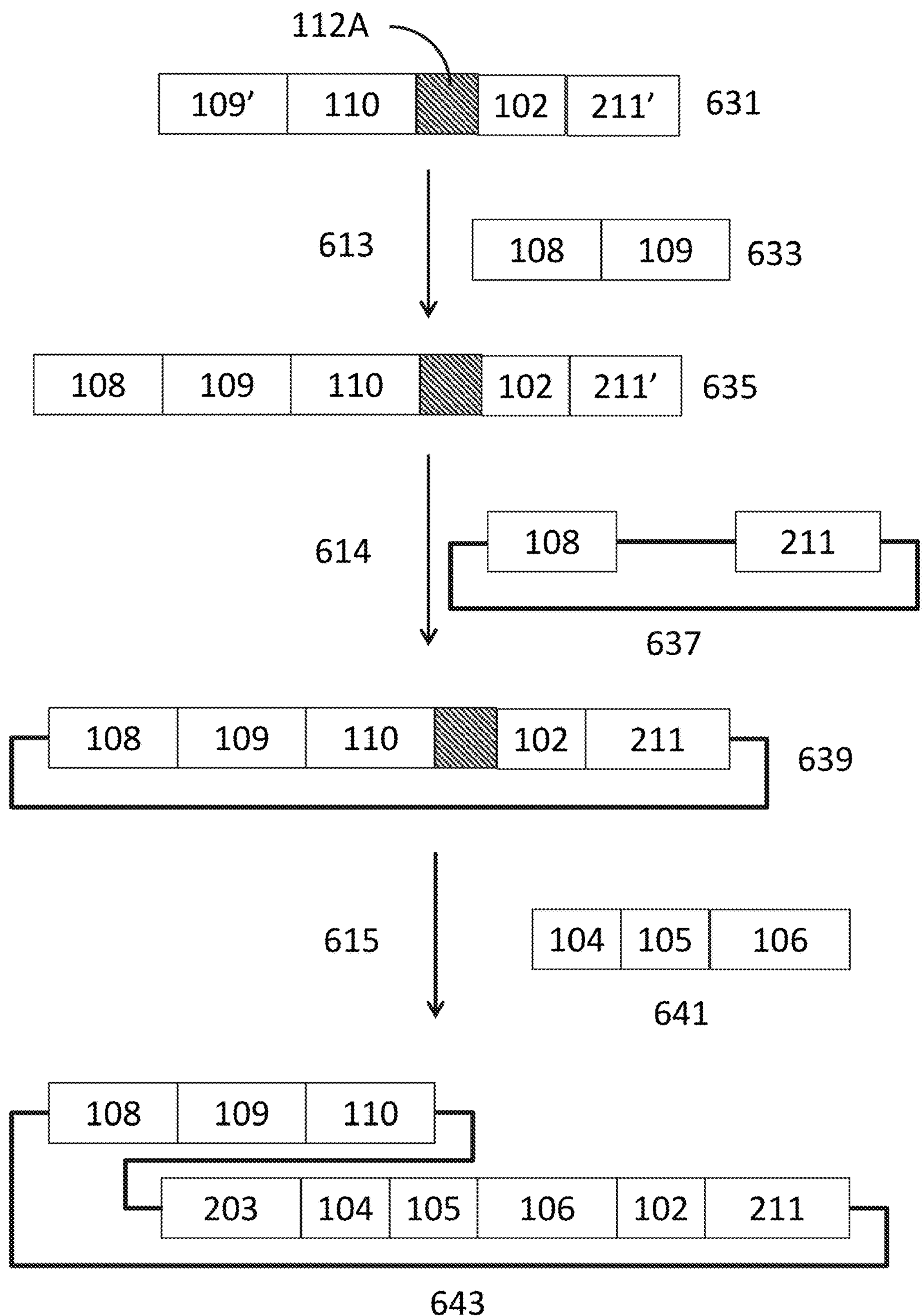
FIG. 6 illustrates a schematic of nucleic acid assembly using polynucleotide populations specific for each variable region.

An exemplary process using populations specific for each variant is seen in FIG. 6. Gene fragment 631 is synthesized comprising the second region of fixed variability 109' followed by the second hypervariable region 110, the first restriction endonuclease site 112A, the first hypervariable region 102, and universal primer 211'. In some instances, the first hypervariable region comprises a CDR. In some instances, the second hypervariable region comprises a CDR. In some instances, the CDR is CDR3. In some instances, the restriction endonuclease site is a TIIS-RE site. Gene fragment 631 is combined and PCR amplified 613 with a population of gene fragments 633 comprising the second complementary region adjacent to a second variable region 108 followed by the second variable region 109 to generate gene fragment 635. Gene fragment 635 comprises the second complementary region adjacent to a second variable region 108 followed by the second variable region 109, the second hypervariable region 110, the first restriction endonuclease site 112A, the first hypervariable region 106, and universal primer 211'. Gene fragment 635 is then assembled 614 into a destination vector 637 comprising the second complementary region adjacent to a second variable region 108 and the second variable constant segment 211 to generate gene fragment 639. Gene fragment 639 comprises the second complementary region adjacent to a second variable region 108 followed by the second variable region 109, the second hypervariable region 110, the first restriction endonuclease site 112A, the first hypervariable region 102, and the second variable constant segment 211. Gene fragment 641 is synthesized and comprises the self-cleaving peptide sequence 104, the first complementary region adjacent to a first variable region 105, and the first variable region 106. Gene fragment 639 and gene fragment 641 are assembled 615 to insert the second region of any defined length 203 to generate final construct 643. The final construct 643 comprises the second complementary region adjacent to a second variable region 108 followed by the second variable region 109, the second hypervariable region 110, the second region of any defined length 203, the self-cleaving peptide sequence 104, the first complementary region adjacent to a first variable region 105, the first variable region 106, the first hypervariable region 102, and the second variable constant segment 211. In some instances, a number of final constructs generated is about 10000. In some instances, a number of final constructs generated is about 1000, 2000, 5000, 8000, 10000, 15,000, 20,000, 100,000, or about 1,000,000. In some instances, a number of final constructs generated is at least 1000, 2000, 5000, 8000, 10000, 15,000, 20,000, 100,000, or at least 1,000,000.

Described herein are methods of de novo synthesis for nucleic acid sequence assembly. Such methods are in some instances used for the assembly of smaller nucleic acid fragments. In some instances, nucleic acid fragments comprise constant regions, variable regions, overlap regions, hypervariable regions, barcodes, regions encoding for peptide cleavage sites, regions encoding for genes or fragments of genes, restriction sites, or other region. In some instances, a first constant sequence, a first variable sequence, and a first sequence are synthesized and then subject to polymerase chain assembly (PCA) to generate a first plurality of gene fragments. In some instances, the first constant sequence is a leader sequence. In some instances, the second sequence is a CDR. In some instances, the first constant sequence is a leader sequence, and the second sequence is a CDR. In some instances, a second constant sequence, a second variable sequence and a second sequence are synthesized and then subject to assembly PCR or PCA to generate a second plurality of gene fragments. In some instances, the second constant sequence is a leader sequence. In some instances, the second sequence is a CDR. In some instances a third plurality of gene fragments comprising a third constant region followed by a first complementary sequence and a fourth plurality of gene fragments comprising a variable constant segment are synthesized. In some instances, the first complementary sequence comprises a sequence complementary region adjacent to one or more variable regions. In some instances, the first complementary sequence comprises a 20-60 bp, 10-20 bp, 15-45 bp, 20-60 bp, 30-40 bp, 30-60 bp, or a 40-60 bp region. In some instances, the first complementary sequence comprises about a 15, 20, 25, 30, 35, 40, 45, 50, 55, 60, or 65 bp region. In some instances, the first complementary sequence comprises about a 40 bp region. In some instances, the first complementary sequence comprises a self-cleaving peptide. In some instances a self-cleaving peptide sequence is P2A. In some instances, the third plurality of gene fragments and the fourth plurality of gene fragments are added to the first plurality of gene fragments and the second plurality of gene fragments followed by PCR. Optionally, an error correction reaction is performed. In some instances, resulting construct is pooled, cloned, and subject to next generation sequencing. In some instances, the resulting construct comprises one or more genes. In some instances, the resulting construct comprises an immunoglobulin, or fragment thereof.

Described herein are methods of de novo synthesis for nucleic acid sequence assembly. Such methods are in some instances used for the assembly of smaller nucleic acid fragments. In some instances, nucleic acid fragments comprise constant regions, variable regions, hypervariable regions, overlap regions, barcodes, regions encoding for peptide cleavage sites, regions encoding for genes or fragments of genes, restriction sites, or other region. In some instances, nucleic acid fragments comprise gene fragments. In some instances, the fragments are at least 50, 75, 100, 125, 150, 175, 200, 250, 500, 800, 1000, 2000, 5000, 8000, 10,000, or at least 20,000 bases in length. In some instances, the fragments are no more than 50, 75, 100, 125, 150, 175, 200, 250, 500, 800, 1000, 2000, 5000, 8000, 10,000, or no more than 20,000 bases in length. In some instances, the fragments are about 50, 75, 100, 125, 150, 175, 200, 250, 500, 800, 1000, 2000, 5000, 8000, 10,000, or about 20,000 bases in length. In some instances, the fragments are 50-5000, 50-1000, 50-500, 50-250, 100-500, 200-1000, 500-10,000, 500-5,000, 1000-8000, or 1500-10,000 bases in length. Nucleic acid fragments are synthesized comprising variants of a first variable region and amplified with fragments comprising a region of fixed variability. In some instances, the region of fixed variability comprises a region complementary to the first variable region and a first hypervariable region to generate a first plurality of fragments. In some instances, the first hypervariable region comprises a CDR and J segment. In some instances, the region of fixed variability comprises a 20-60 base pair (bp), 10-20 bp, 15-45 bp, 20-60 bp, 30-40 bp, 30-60 bp, or a 40-60 bp region. In some instances, the region of fixed variability comprises about a 15, 20, 25, 30, 35, 40, 45, 50, 55, 60, or 65 bp region. In some instances, the region of fixed variability comprises about a 40 bp region. Fragments can be synthesized comprising variants of a second variable region and amplified with fragments comprising a second CDR and J segment to generate a second plurality of fragments. A third plurality of fragments can be synthesized comprising a constant region, a first complementary region adjacent to the variable regions, a first leader sequence, and a second complementary region complementary to the second variable region and a second CDR and J segment. In some instances, the first complementary sequence comprises a 20-60 bp, 10-20 bp, 15-45 bp, 20-60 bp, 30-40 bp, 30-60 bp, or a 40-60 bp region. In some instances, the first complementary sequence comprises about a 15, 20, 25, 30, 35, 40, 45, 50, 55, 60, or 65 bp region. In some instances, the first complementary sequence comprises about a 40 bp region. In some instances, the second complementary sequence comprises a 20-60 bp, 10-20 bp, 15-45 bp, 20-60 bp, 30-40 bp, 30-60 bp, or a 40-60 bp region. In some instances, the second complementary sequence comprises about a 15, 20, 25, 30, 35, 40, 45, 50, 55, 60, or 65 bp region. In some instances, the second complementary sequence comprises about a 40 bp region. Constant regions may be adjusted for the construct size. In some instances, the constant region is at least 50, 75, 100, 125, 150, 175, 200, 250, 500, 800, 1000, 2000, 5000, 8000, 10,000, or at least 20,000 bases in length. In some instances, the constant region is no more than 50, 75, 100, 125, 150, 175, 200, 250, 500, 800, 1000, 2000, 5000, 8000, 10,000, or no more than 20,000 bases in length. In some instances, the constant region is about 50, 75, 100, 125, 150, 175, 200, 250, 500, 800, 1000, 2000, 5000, 8000, 10,000, or about 20,000 bases in length. In some instances, the constant region is 50-5000, 50-1000, 50-500, 50-250, 100-500, 200-1000, 500-10,000, 500-5,000, 1000-8000, or 1500-10,000 bases in length. In some instances, the first plurality of fragments, the second plurality of fragments, and the third plurality of fragments are assembled using an enzymatic based assembly method, PCR purified, and pooled. In some instances, substantially all non-assembled fragments are purified away. In some instances, at least 90%, 95%, 97%, 98%, 99%, 99.5%, 99.9%, or at least 99.99% of the non-assembled fragments are purified away. In some instances, the final construct is cloned into large nucleic acid. In some instances, the large nucleic acid is a vector.

Described herein are methods of de novo synthesis for nucleic acid sequence assembly. Such methods are in some instances used for the assembly of smaller nucleic acid fragments. In some instances, nucleic acid fragments comprise constant regions, variable regions, hypervariable regions, overlap regions, barcodes, regions encoding for peptide cleavage sites, regions encoding for genes or fragments of genes, restriction sites, or other region. In some instances, nucleic acid fragments comprise gene fragments. In some instances, the gene fragments are variant gene fragments. In some instances fragments comprising a first variable region are synthesized. In some instances, the fragments are at least 50, 75, 100, 125, 150, 175, 200, 250, 500, 800, 1000, 2000, 5000, 8000, 10,000, or at least 20,000 bases in length. In some instances, the fragments are no more than 50, 75, 100, 125, 150, 175, 200, 250, 500, 800, 1000, 2000, 5000, 8000, 10,000, or no more than 20,000 bases in length. In some instances, the fragments are about 50, 75, 100, 125, 150, 175, 200, 250, 500, 800, 1000, 2000, 5000, 8000, 10,000, or about 20,000 bases in length. In some instances, the fragments are 50-5000, 50-1000, 50-500, 50-250, 100-500, 200-1000, 500-10,000, 500-5,000, 1000-8000, or 1500-10,000 bases in length. In some instances, the fragments are amplified with a first hypervariable segment to generate a first plurality of gene fragments. In some instances, another set of fragments comprising a second variable region are synthesized. In some instances, an different set of fragments are amplified with a second hypervariable segment to generate a second plurality of gene fragments. In some instances, the hypervariable segment comprises a CDR3 and J segment. In some instances, a third plurality of gene fragments comprising a sequence homologous to the first hypervariable segment followed by a constant region, a complementary sequence, a first leader sequence, and a region complementary to the second variable region is synthesized. In some instances, the region complementary to the second variable region is 20-60 bp, 10-20 bp, 15-45 bp, 20-60 bp, 30-40 bp, 30-60 bp, or a 40-60 in length. In some instances, the region complementary to the second variable region is about a 15, 20, 25, 30, 35, 40, 45, 50, 55, 60, or 65 bp in length. In some instances, the first complementary sequence comprises a sequence complementary region adjacent to one or more variable regions. In some instances, the first complementary sequence comprises a 20-60 bp, 10-20 bp, 15-45 bp, 20-60 bp, 30-40 bp, 30-60 bp, or a 40-60 bp region. In some instances, the first complementary sequence comprises about a 15, 20, 25, 30, 35, 40, 45, 50, 55, 60, or 65 bp region. In some instances, the first complementary sequence comprises about a 40 bp region. In some instances, the first complementary sequence comprises a self-cleaving peptide. In some instances a self-cleaving peptide sequence is P2A. In some instances, the third plurality of nucleic acids comprises 10-1000, 100-500, 50-5,000, 50-10,000, 100-1000, 200-1000, 500-10,000 or 1000-10,000 variants. In some instances, the first plurality of gene fragments, the second plurality of gene fragments, and the third plurality of gene fragments are assembled. In some instances, the first plurality of gene fragments, the second plurality of gene fragments, and the third plurality of gene fragments are assembled and cloned into a destination vector. In some instances, the final construct comprises a second leader sequence followed by the second variable region, the second hypervariable segment, the second constant region, the first complementary sequence, the first leader sequence, the first variable region, the first hypervariable segment, and the variable constant region.

Provided herein are methods for nucleic acid assembly, wherein gene fragments or genes for assembly comprise a homology sequence. In some instances, the homology sequence comprises at least or about 5, 10, 20, 30, 40, 50, 60, 70, 80, 90, 100, or more than 100 base pairs. In some instance, the number of base pairs is 40 base pairs. In some instances, the number of base pairs has a range of about 5 to 100, 10 to 90, 20 to 80, 30 to 70, or 40 to 60 base pairs.

Gene fragments described herein may comprise homology sequences. In some instances, the gene fragment or genes for assembly comprise one or more homology sequences. In some instances, the one or more homology sequences is a high diversity region. In some instances, the one or more homology sequences is complementary to a variable region. In some instances, the one or more homology sequences is a hypervariable region.

Provided herein are methods for synthesizing nucleic acids, wherein gene fragments or genes for assembly comprise a barcode. In some instances, the barcode comprises at least or about 5, 10, 20, 30, 40, 50, 60, 70, 80, 90, 100, or more than 100 base pairs. In some instances, the barcode is recognized by a restriction enzyme. In some instances, the restriction enzyme recognizes asymmetric DNA sequences. In some instances, a first population of gene fragments and a second population of gene fragments are designed having complementary barcode sequences, such that subsequent to cleavage of the nucleic acids in each population, the first population and the second population are able to anneal to each other.

Various restriction enzymes and restriction sites may be used herein. In some instances, the restriction enzyme is an endonuclease. In some instances, the restriction enzyme recognizes palindromic sequences and cleaves both strands symmetrically within the recognition sequence. In some instances, the restriction enzyme recognizes asymmetric nucleic acid sequences and cleaves both nucleic acid strands outside the recognition sequence. In some instances, the endonuclease is a Type II endonuclease. Exemplary Type II endonucleases include, but are not limited to, HhaI, HindIII, NotI, BbvCI, EcoRI, and BglI. In some instances, the endonuclease is a Type IIS endonuclease. Exemplary Type IIS endonucleases include, but are not limited to, AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI.

Methods as described herein, in some embodiments, comprise synthesizing nucleic acids from genes or gene fragments that encode a self-cleaving peptide. In some instances, the self-cleaving peptide is a 2A peptide. In some instances, the 2A peptide is T2A, P2A, E2A, or F2A. In some instances, the 2A peptide is P2A.

Provided herein are methods for synthesizing nucleic acids from genes or gene fragments that encode a hypervariable region. In some instances, the hypervariable region is a complementarity-determining region (CDR). In some instances, the CDR is CDR1, CDR2, or CDR3. In some instances, the CDR is a heavy domain including, but not limited to, CDR-H1, CDR-H2, and CDR-H3. In some instances, the CDR is a light domain including, but not limited to, CDR-L1, CDR-L2, and CDR-L3.

The CDR region may have varying lengths. In some instances, the CDR region comprises at least or about 5, 10, 20, 30, 40, 50, 60, 70, 80, 90, 100, 125, 150, 175, 200, 225, 250, 275, 300, 325, 350, 375, 400, or more than 400 base pairs. In some instances, the CDR region comprises about 100 base pairs.

Composition and methods described herein may comprise gene or gene fragments comprising antigen binding sequences, such as CDRs or other sequence. In some instances, the gene fragment or genes encode a CDR region and a V segment, D segment, J segment, or a combination thereof. In some instances, the gene fragment or genes comprise a CDR region and a V segment. In some instances, the gene fragment or genes comprising a CDR region and a V segment comprises at least or about 5, 10, 20, 30, 40, 50, 60, 70, 80, 90, 100, 125, 150, 175, 200, 225, 250, 275, 300, 325, 350, 375, 400, or more than 400 base pairs. In some instances, the gene fragment or genes comprise a CDR region and a D segment. In some instances, the gene fragment or genes comprising a CDR region and a D segment comprises at least or about 5, 10, 20, 30, 40, 50, 60, 70, 80, 90, 100, 125, 150, 175, 200, 225, 250, 275, 300, 325, 350, 375, 400, or more than 400 base pairs. In some instances, the gene fragment or genes comprise a CDR region and a J segment. In some instances, the gene fragment or genes comprising a CDR region and a J segment comprises at least or about 5, 10, 20, 30, 40, 50, 60, 70, 80, 90, 100, 125, 150, 175, 200, 225, 250, 275, 300, 325, 350, 375, 400, or more than 400 base pairs. In some instances, the CDR is CDR1, CDR2, or CDR3. In some instances, the CDR is CDR3.

Methods as described herein, in some embodiments, comprise synthesizing nucleic acids from genes or gene fragments that encode a variable region. In some instances, the variable region is of an immunoglobulin. In some instances, a plurality of variant variable regions are synthesized. In some instances, at least or about 10, $10^1$, $10^2$, $10^3$, $10^4$, $10^5$, $10^6$, or more than $10^6$ variant variable regions are synthesized. In some instances, at least or about 10, 20, 30, 40, 50, 60, 70, 80, 90, 100, 110, 120, 130, 140, 150, 160, 170, 180, 190, 200, or more than 200 variant variable regions are synthesized.

Methods as described herein, in some embodiments, comprise synthesizing nucleic acids from genes or gene fragments that encode a region of any defined length. In some instances, the region of any defined length is a constant region. In some instances, the constant region is of an immunoglobulin. In some instances, at least or about 10, $10^1$, $10^2$, $10^3$, $10^4$, $10^5$, $10^6$, or more than $10^6$ variant regions of any defined length are synthesized. In some instances, at least or about 10, 20, 30, 40, 50, 60, 70, 80, 90, 100, 110, 120, 130, 140, 150, 160, 170, 180, 190, 200, or more than 200 variant regions of any defined length are synthesized. In some instances, the constant region is at least 50, 75, 100, 125, 150, 175, 200, 250, 500, 800, 1000, 2000, 5000, 8000, 10,000, or at least 20,000 bases in length. In some instances, the constant region is no more than 50, 75, 100, 125, 150, 175, 200, 250, 500, 800, 1000, 2000, 5000, 8000, 10,000, or no more than 20,000 bases in length. In some instances, the constant region is about 50, 75, 100, 125, 150, 175, 200, 250, 500, 800, 1000, 2000, 5000, 8000, 10,000, or about 20,000 bases in length. In some instances, the constant region is 50-5000, 50-1000, 50-500, 50-250, 100-500, 200-1000, 500-10,000, 500-5,000, 1000-8000, or 1500-10,000 bases in length.

Provided herein are methods for nucleic acid assembly, wherein a number of gene fragments are assembled. In some instances, the gene fragments are assembled processively or sequentially. In some instances, the gene fragments are assembled into a vector. In some instances, the gene fragments are assembled for long linear gene assembly. In some instances, the number of gene fragments is at least or about 2, 3, 4, 5, 6, 7, 8, 9, 10, or more than 10 gene fragments. In some instances, the number of gene fragments is at least or about 10, 11, 12, 13, 14, 15, 16, 17, 18, 19, 20, or more than 20 gene fragments. In some instances, the number of gene fragments is in a range of about 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10. In some instances, the number of gene fragments is about 1 to about 20, about 2 to about 18, about 3 to about 17, about 4 to about 16, about 6 to about 14, or about 8 to about 12.

Provided herein are methods for nucleic acid assembly, wherein a ratio of gene fragments assembled is about 0.2:1, 0.25:1, 0.5:1, 0.75:1, 1:1, 1:1.5, 1:2, 1:3, 1:4, 1:5, or more than 1:5. For example, if two gene fragments are assembled, a ratio of the first gene fragment to the second gene fragment is 1:1. In some instances, a ratio of the first gene fragment to the second gene fragment is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Methods as described herein for nucleic acid assembly may comprise assembly of one or more gene fragments into a vector, wherein a ratio of the one or more gene fragments to the vector varies. In some instances, a ratio of the one or more gene fragments to the vector is at least or about 0.2:1, 0.25:1, 0.5:1, 0.75:1, 1:1, 1:1.5, 1:2, 1:3, 1:4, 1:5, or more than 1:5. In some instances, a ratio of the one or more gene fragments to the vector is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Methods as described herein for nucleic acid assembly may comprise assembly of polynucleotide populations for assembly into a vector. In some instances, PCR is performed for assembly of polynucleotide populations. In some instances, the polynucleotide population comprises at least or about 2, 3, 4, 5, 6, 7, 8, 9, 10, 15, 20, 25, 30, 35, 40, 45, 50, 60, 70, 80, 90, 100, 200, or more than 200 polynucleotides. In some instances, the polynucleotide population are assembled to generate a long nucleic acid comprising at least or about 50, 100, 200, 250 300, 400, 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, 20000, 30000, 40000, 50000, 60000, 70000, 80000, 90000, 100000 or more than 100000 bases.

Nucleic acid assembly, in some embodiments, result in generation of nucleic acids encoding an immunoglobulin. In some instances, the immunoglobulin is an antibody. As used herein, the term antibody will be understood to include proteins having the characteristic two-armed, Y-shape of a typical antibody molecule as well as one or more fragments of an antibody that retain the ability to specifically bind to an antigen. Exemplary antibodies include, but are not limited to, a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv) (including fragments in which the VL and VH are joined using recombinant methods by a synthetic or natural linker that enables them to be made as a single protein chain in which the VL and VH regions pair to form monovalent molecules, including single chain Fab and scFab), a single chain antibody, a Fab fragment (including monovalent fragments comprising the VL, VH, CL, and CH1 domains), a F(ab')2 fragment (including bivalent fragments comprising two Fab fragments linked by a disulfide bridge at the hinge region), a Fd fragment (including fragments comprising the VH and CH1 fragment), a Fv fragment (including fragments comprising the VL and VH domains of a single arm of an antibody), a single-domain antibody (dAb or sdAb) (including fragments comprising a VH domain), an isolated complementarity determining region (CDR), a diabody (including fragments comprising bivalent dimers such as two VL and VH domains bound to each other and recognizing two different antigens), a fragment comprised of only a single monomeric variable domain, disulfide-linked Fvs (sdFv), an intrabody, an anti-idiotypic (anti-Id) antibody, or ab antigen-binding fragments thereof. In some instances, the libraries disclosed herein comprise nucleic acids encoding for a scaffold, wherein the scaffold is a Fv antibody, including Fv antibodies comprised of the minimum antibody fragment which contains a complete antigen-recognition and antigen-binding site. In some embodiments, the Fv antibody consists of a dimer of one heavy chain and one light chain variable domain in tight, non-covalent association, and the three hypervariable regions of each variable domain interact to define an antigen-binding site on the surface of the VH-VL dimer. In some embodiments, the six hypervariable regions confer antigen-binding specificity to the antibody. In some embodiments, a single variable domain (or half of an Fv comprising only three hypervariable regions specific for an antigen, including single domain antibodies isolated from camelid animals comprising one heavy chain variable domain such as VHH antibodies or nanobodies) has the ability to recognize and bind antigen. In some instances, the libraries disclosed herein comprise nucleic acids encoding for a scaffold, wherein the scaffold is a single-chain Fv or scFv, including antibody fragments comprising a VH, a VL, or both a VH and VL domain, wherein both domains are present in a single polypeptide chain. In some embodiments, the Fv polypeptide further comprises a polypeptide linker between the VH and VL domains allowing the scFv to form the desired structure for antigen binding. In some instances, a scFv is linked to the Fc fragment or a VHH is linked to the Fc fragment (including minibodies). In some instances, the antibody comprises immunoglobulin molecules and immunologically active fragments of immunoglobulin molecules, e.g., molecules that contain an antigen binding site. Immunoglobulin molecules are of any type (e.g., IgG, IgE, IgM, IgD, IgA and IgY), class (e.g., IgG 1, IgG 2, IgG 3, IgG 4, IgA 1 and IgA 2) or subclass.

Methods as described herein for nucleic acid assembly may comprise synthesis of gene fragments in individual reactions. In some instances, synthesis of gene fragments is followed by multiplexed gene assembly. In some instances, multiplexed gene assembly results in at least or about 2, 3, 4, 5, 6, 7, 8, 9, 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10000, 20000, 40000, or more than 40000 sequences or gene fragments assembled. In some instances, at least or about 10, 15, 20, 25, 30, 35, 40, 45, 50, 55, 60, 65, 70, 75, 80, 85, 90, 95, 100, or more than 100 genes are assembled. In some instances, multiplexed gene assembly results in assembly of at least or about 2, 3, 4, 5, 6, 7, 8, 9, 10, 15, 20, 25, 30, 35, 40, 45, 50, 60, 70, 80, 90, 100, 200, 300, 400, 500, 600, 700, 800, or more than 800 base pairs (bp).

Nucleic acid assembly using methods as described herein may result in libraries of nucleic acids comprising low error rate, low dropout rate, low runaway, low percentage of chimeric genes, or a combination thereof. In some instances, libraries of nucleic acids assembled using methods described herein comprise base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% AT dropout. In some instances, libraries of nucleic acids assembled using methods described herein result in less than 1.0%, 1.5%, 2.0%, 2.5%, 3.0%, 3.5%, 4.0%, 4.5%, or 5.0% AT dropout. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% GC dropout. In some instances, libraries of nucleic acids assembled using methods described herein result in less than 1.0%, 1.5%, 2.0%, 2.5%, 3.0%, 3.5%, 4.0%, 4.5%, or 5.0% GC dropout. In some instances, libraries of nucleic acids assembled using methods described herein comprise at most 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% of chimeric genes.

Methods as described herein for nucleic acid assembly may comprise enzymatic based assembly of one or more gene fragments. In some instances, the enzymatic mediated nucleic acid assembly comprises addition of homologous sequences to gene fragments. In some instances, de novo synthesized gene fragments already comprise homology sequences. In some instances, the enzymatic mediated nucleic acid assembly comprises use of an enzymatic mixture. In some instances, the enzymatic mixture comprises an endonuclease. In some instances, the enzymatic mixture optionally comprises an exonuclease, a polymerase, or a ligase. In some instances, the enzymatic mixture comprises an exonuclease, an endonuclease, a polymerase, and a ligase. In some instances, the enzymatic mixture comprises an endonuclease, a polymerase, and a ligase. In some instances, the endonuclease is a flap endonuclease. In some instances, enzymatic mediated nucleic acid assembly results in improved efficiency. In some instances, the enzymatic mixture comprises enzymes that are not restriction enzymes. In some instances, the enzymatic mixture comprises enzymes that are structure specific enzymes. In some instances, the enzymatic mixture comprises enzymes that are structure specific enzymes and not sequence specific enzymes.

Methods for enzymatic mediated nucleic acid assembly, in some embodiments, comprise contacting a nucleic acid using an enzyme comprising exonuclease activity. In some instances, the exonuclease comprises 3' exonuclease activity. Exemplary exonucleases comprising 3'exonuclease activity include, but are not limited to, exonuclease I, exonuclease III, exonuclease V, exonuclease VII, and exonuclease T. In some instances, the exonuclease comprises 5' exonuclease activity. Exemplary exonucleases comprising 5' exonuclease activity include, but are not limited to, exonuclease II, exonuclease IV, exonuclease V, exonuclease VI, exonuclease VII, exonuclease VIII, T5 exonuclease, and T7 exonuclease. In some instances, the exonuclease is exonuclease III (ExoIII). Exonucleases include wild-type exonucleases and derivatives, chimeras, and/or mutants thereof. Mutant exonucleases include enzymes comprising one or more mutations, insertions, deletions or any combination thereof within the amino acid or nucleic acid sequence of an exonuclease.

In some instances, the exonuclease is used at a temperature optimal for enzymatic activity, for example, a temperature in a range of about 25-80° C., 25-70° C., 25-60° C., 25-50° C., or 25-40° C. In some instances, the temperature is about 37° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

In some instances, methods for enzymatic mediated nucleic acid assembly do not comprise using an exonuclease. In some instances, methods for enzymatic mediated nucleic acid assembly comprise using an exonuclease. In some instances, one or more exonucleases are used. For example, at least or about 1, 2, 3, 4, 5, 6, or more than 6 exonucleases are used. In some instances, the exonuclease comprises 5' to 3' exonuclease activity. In some instances, the exonuclease comprises 3' to 5' exonuclease activity. In some instances, methods comprise contacting double stranded DNA with an endonuclease. In some instances, the endonuclease is a flap endonuclease. In some instances, methods comprise contacting double stranded DNA with a flap endonuclease, a ligase, or a polymerase. In some instances, the flap endonuclease is flap endonuclease 1.

Methods for enzymatic mediated nucleic acid assembly, in some embodiments, comprise contacting a nucleic acid using an enzyme comprising endonuclease activity. In some instances, the endonuclease comprises 5' nuclease activity. In some instances, the endonuclease comprises 3' nuclease activity. In some instances, the endonuclease is a flap endonuclease. In some instances, the flap endonuclease comprises 5' nuclease activity. In some instances, the flap endonuclease is a member of a 5'-nuclease family of enzymes. Exemplary 5'-nuclease enzymes include, but are not limited to, flap endonuclease 1, exonuclease 1, xeroderma pigmentosum complementation group G (XPG), Dna2, and gap endonuclease 1 (GEN1). In some instances, the flap endonuclease is flap endonuclease 1. In some instances, the flap endonuclease comprises 3' nuclease activity. Exemplary flap endonucleases with 3' nuclease activity include, but are not limited to, RAG1, RAG2, and MUS81. In some instances, the flap endonuclease is an archaeal, bacteria, yeast, plant, or mammalian flap endonuclease.

In some instances, the endonuclease is used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C. In some instances, the endonuclease is a thermostable endonuclease. A thermostable endonuclease may include endonucleases that are functional at temperatures at least or about 60° C., 65° C., 70° C., 75° C., 80° C., or more than 80° C. In some instances, the endonuclease is a flap endonuclease. In some instances, the flap endonuclease is a thermostable flap endonuclease.

Provided herein are methods for nucleic acid assembly, wherein the ratio of the endonuclease to the exonuclease is from about 0.1:1 to about 1:5. In some instances, the endonuclease is a flap endonuclease. In some instances, the ratio of the endonuclease to the exonuclease is at least or about 0.2:1, 0.25:1, 0.5:1, 0.75:1, 1:1, 1:1.5, 1:2, 1:3, 1:4, 1:5, or more than 1:5. In some instances, the ratio of the endonuclease to the exonuclease is at least or about 1:1, 1:0.9, 1:0.85, 1:0.8, 1:0.75, 1:0.7, 1:0.65, 1:0.6, 1:0.55, 1:0.5, 1:0.45, 1:0.4, 1:0.35, 1:0.3, 1:0.25, 1:0.2, 1:0.15, 1:0.1, or less than 1:0.1.

Provided herein are methods for nucleic acid assembly comprising an exonuclease, wherein the concentration of the exonuclease is from about 0.1 U to about 20 U or more. For example, the concentration of the exonuclease is at least or about 0.1 U, 0.25 U, 0.5 U, 0.75 U, 1 U, 1.6 U, 2 U, 3 U, 4 U, 5 U, 6 U, 7 U, 8 U, 9 U, 10 U, 12 U, 14 U, 16 U, 18 U, 20 U, or more than 20 U. In some instances, the concentration of the exonuclease is in a range of about 0.5 U to about 1.0 U. In some instances, the concentration of the exonuclease is from about 1.0 U to about 2.0 U. In some instances, the concentration of the exonuclease is about 1.6 U. In some instances, the concentration of the exonuclease is about 5.0 U. In some instances, the concentration of the exonuclease from about 0.1 U to 20 U, 0.25 U to 18 U, 0.5 U to 16 U, 0.75 U to 14 U, 1 U to 12 U, 2 U to 10 U, 3 U to 9 U, or 4 U to 8 U.

Methods described herein for enzymatic mediated nucleic acid assembly may comprise an endonuclease, wherein the concentration of the endonuclease is from about 0.25 U to about 12 U or more. In some instances, the endonuclease is a flap endonuclease. Exemplary concentrations of the endonuclease, include, but are not limited to, at least or about 0.25 U, 0.5 U, 0.75 U, 1 U, 2 U, 3 U, 4 U, 5 U, 6 U, 7 U, 8 U, 9 U, 10 U, 11 U, 12 U, or more than 12 U. In some instances, the concentration of the endonuclease is 0.32 U. In some instances, the concentration of the endonuclease is 1.6 U. In some instances, the concentration of the endonuclease is in a range of about 0.32 U to about 4.8 U. In some instances, the concentration of the endonuclease is in a range of about 0.25 U to 12 U, 0.5 U to 11 U, 0.75 U to 10 U, 1 U to 9 U, 2 U to 8 U, 3 U to 7 U, or 4 U to 6 U.

Provided herein are methods for enzymatic mediated nucleic acid assembly, wherein a nucleic acid is mixed with a polymerase. In some instances, the polymerase is a DNA polymerase. In some instances, the polymerase is a high fidelity polymerase. A high fidelity polymerase may include polymerases that result in accurate replication or amplification of a template nucleic acid. In some instances, the DNA polymerase is a thermostable DNA polymerase. The DNA polymerase may be from any family of DNA polymerases including, but not limited to, Family A polymerase, Family B polymerase, Family C polymerase, Family D polymerase, Family X polymerase, and Family Y polymerase. In some instances, the DNA polymerase is from a genus including, but not limited to, *Thermus, Bacillus, Thermococcus, Pyrococcus, Aeropyrum, Aquifex, Sulfolobus, Pyrolobus*, or *Methanopyrus.*

Polymerases described herein for use in an amplification reaction may comprise various enzymatic activities. Polymerases are used in the methods of the invention, for example, to extend primers to produce extension products. In some instances, the DNA polymerase comprises 5' to 3' polymerase activity. In some instances, the DNA polymerase comprises 3' to 5' exonuclease activity. In some instances, the DNA polymerase comprises proofreading activity. Exemplary polymerases include, but are not limited to, DNA polymerase (I, II, or III), T4 DNA polymerase, T7 DNA polymerase, Bst DNA polymerase, Bca polymerase, Vent DNA polymerase, Pfu DNA polymerase, and Taq DNA polymerase. Non-limiting examples of thermostable DNA polymerases include, but are not limited to, Taq, Phusion® DNA polymerase, Q5® High Fidelity DNA Polymerase, LongAmp® DNA polymerase, Expand High Fidelity polymerase, HotTub polymerase, Pwo polymerase, Tfl polymerase, Tli polymerase, UlTma polymerase, Pfu polymerase, KOD DNA polymerase, JDF-3 DNA polymerase, PGB-D DNA polymerase, Tgo DNA polymerase, *Pyrolobus furmarius* DNA polymerase, Vent polymerase, and Deep Vent polymerase.

Described herein are methods comprising a DNA polymerase, wherein a concentration of the DNA polymerase is from about 0.1 U to about 2 U, or more than 2 U. In some instances, the concentration of the DNA polymerase is about 0.1 U. In some instances, the concentration of the DNA polymerase is about 0.2 U. In some instances, the concentration of the DNA polymerase is about 0.01 U. In some instances, the concentration of the DNA polymerase is in a range of at least or about 0.005 U to 2 U, 0.005 U to 1 U, 0.005 U to 0.5 U, 0.01 U to 1 U, 0.1 U to 0.5 U, 0.1 U to 0.5 U, 0.1 U to 1 U, 0.1 U to 1.5 U, 0.1 U to 2 U, 0.5 U to 1.0 U, 0.5 U to 1.5 U, 0.5 U to 2 U, 1 U to 1.5 U, 1.0 U to 2.0 U, or 1.5 U to 2 U.

The DNA polymerase for use in methods described herein are used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

Methods for enzymatic mediated nucleic acid assembly as described herein, in some embodiments, comprise treating a nucleic acid using a ligase. Ligases as described herein may function to join nucleic acid fragments. For example, the ligase functions to join adjacent 3'-hydroxylated and 5'-phosphorylated termini of DNA. Ligases include, but are not limited to, *E. coli* ligase, T4 ligase, mammalian ligases (e.g., DNA ligase I, DNA ligase II, DNA ligase III, DNA ligase IV), thermostable ligases, and fast ligases. In some instances, the ligase is a thermostable ligase. In some instances, the ligase is Ampligase.

The concentration of the ligase may vary. In some instances, the concentration of the ligase is in a range of about 0 U to about 2 U. An exemplary concentration of the ligase is about 0.5 U. In some instances, the concentration of the ligase is about 1.0 U. In some instances, the concentration of the ligase is about 5.0 U. In some instances, the concentration of the ligase is in a range of at least or about 0 U to 0.25 U, 0 U to 0.5 U, 0 U to 1 U, 0 U to 1.5 U, 0 U to 2 U, 0.25 U to 0.5 U, 0.25 U to 1.0 U, 0.25 U to 1.5 U, 0.25 U to 2.0 U, 0.5 U to 1.0 U, 0.5 U to 1.5 U, 0.5 U to 2.0 U, 1.0 U to 1.5 U, 1.0 U to 2.0 U, or 1.5 U to 2.0 U, 2.0 U to 4.0 U, 4.0 U to 6.0 U, 4.0 U to 8.0 U, 6.0 U to 10.0 U.

In some instances, the ligase is used at a temperature optimal for enzymatic activity, for example, a temperature of 25-80° C., 25-70° C., 25-60° C., 25-50° C., or 25-40° C. In some instances, the temperature is about 50° C. In some instances, the temperature is about 55° C. In some instances, the temperature is about 65° C. In some instances, the temperature is at least or about 15° C., 20° C., 25° C., 30° C., 35° C., 40° C., 45° C., 50° C., 55° C., 60° C., 65° C., 70° C., 75° C., 80° C., or more than 80° C.

Methods described herein for nucleic acid assembly may comprise a ligation reaction. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some instances, after the PCA reaction is complete, an error correction step is conducted using mismatch repair detecting enzymes to remove mismatches in the sequence.

In some instances, methods described herein comprise an amplification reaction. In some instances, the amplification reaction is polymerase chain reaction (PCR). In some instances, the amplification reaction is dial-out PCR. In some instances, the amplification reaction comprises hybridization of a universal primer binding sequence during amplification. In some instances, the universal primer binding sequence is capable of binding the same 5' or 3' primer. In some instances, the universal primer binding sequence is shared among a plurality of target nucleic acids in the amplification reaction.

Provided herein are methods for nucleic acid assembly that may comprise an error correction step. Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some instances, DNA mismatch-binding protein MutS (*Therms aquaticus*) is used to remove failure products from a population of synthesized products. In some instances, error correction is performed using the enzyme Correctase. In some instances, error correction is performed using SURVEYOR endonuclease (Transgenomic), a mismatch-specific DNA endonuclease that scans for known and unknown mutations and polymorphisms for heteroduplex DNA.

The resulting nucleic acids can be verified. In some cases, the nucleic acids are verified by sequencing. In some instances, the nucleic acids are verified by high-throughput sequencing such as by next generation sequencing. Sequencing of the sequencing library can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

Methods as described herein, in some embodiments, result in generation of libraries comprising at least or about $10^1$, $10^2$, $10^3$, $10^4$, $10^5$, $10^6$, $10^7$, $10^8$, $10^9$, $10^{10}$, or more than $10^{10}$ variants. In some instances, sequences for each variant of the libraries comprising at least or about $10^1$, $10^2$, $10^3$, $10^4$, $10^5$, $10^6$, $10^7$, $10^8$, $10^9$, or $10^{10}$ variants are known. In some instances, the libraries comprise a predicted diversity of variants. In some instances, the diversity represented in the libraries is at least or about 60%, 65%, 70%, 75%, 80%, 85%, 90%, 95%, or more than 95% of the predicted diversity. In some instances, the diversity represented in the libraries is at least or about 70% of the predicted diversity. In some instances, the diversity represented in the libraries is at least or about 80% of the predicted diversity. In some instances, the diversity represented in the libraries is at least or about 90% of the predicted diversity. In some instances, the diversity represented in the libraries is at least or about 99% of the predicted diversity. As described herein the term "predicted diversity" refers to a total theoretical diversity in a population comprising all possible variants.

Nucleic acid assembly using methods as described herein may efficiently assemble fragments despite high GC content, direct repeats, or secondary structures. In some instances, the fragments for assembly comprise GC content of at least or about 5%, 10%, 15%, 20%, 25%, 30%, 35%, 40%, 45%, 50%, 60%, 65%, 70%, 75%, 80%, 85%, 90%, 95%, or more than 95%. In some instances, the fragments for assembly comprise at least or about 10, 15, 20, 25, 30, 35, 40, 45, 50, 55, 60, 65, 70, 75, or 80 base pairs (bp) adjacent direct repeats. In some instances, the fragments for assembly comprise secondary structures such as hairpin structures with dG values of at least or about −5, −6, −7, −8, −9, −10, −11, −12, −13, −14, −15, −16, −17, −18, −19, −20, −21, −22, −23, −24, −25, or −26 dG. In some instances, the fragments for assembly comprise secondary structures such as hairpin structures with dG values in a range of about −11 to about −18 dG.

Provided herein are methods for assembly of highly uniform libraries of nucleic acids. In some cases, more than about 80% of synthesized of nucleic acids (RNA or DNA) are represented within 5× of the mean for of nucleic acid representation for a nucleic acid library. In some cases, more than about 90% of synthesized of nucleic acids (RNA or DNA) are represented within 5× of the mean for of nucleic acid representation for a nucleic acid library. In some cases, more than about 90% of nucleic acids are represented within 2× of the mean for nucleic acid representation for the library. In some cases, more than about 90% of nucleic acids are represented within 1.5× of the mean for nucleic acid representation for the library. In some cases, more than about 80% of nucleic acids are represented within 1.5× of the mean for nucleic acid representation for the library.

Nucleic acid libraries assembled by methods described herein comprise a high percentage of correct sequences compared to predetermined sequences. In some instances, nucleic acids libraries disclosed herein have greater than 70% correct sequence compared to predetermined sequences for nucleic acids. In some instances, nucleic acids libraries disclosed herein have greater than 75% correct sequence compared to predetermined sequences for the nucleic acids. In some instances, nucleic acids libraries disclosed herein have greater than 80% correct sequence compared to predetermined sequences for the nucleic acids. In some instances, nucleic acids libraries disclosed herein have greater than 85% correct sequence compared to predetermined sequences for the nucleic acids. In some instances, nucleic acids libraries disclosed herein have greater than 90% correct sequence compared to predetermined sequences for the nucleic acids. In some instances, nucleic acids libraries disclosed herein have greater than 95% correct sequence compared to predetermined sequences for the nucleic acids. In some instances, nucleic acids libraries disclosed herein have greater than 100% correct sequence compared to predetermined sequences for the nucleic acids.

In some instances, nucleic acids libraries disclosed herein have greater than 70% correct sequence compared to predetermined sequences for the nucleic acids following an amplification reaction. In some instances, nucleic acids libraries disclosed herein have greater than 75% correct sequence compared to predetermined sequences for the nucleic acids following an amplification reaction. In some instances, nucleic acids libraries disclosed herein have greater than 80% correct sequence compared to predetermined sequences for the nucleic acids following an amplification reaction. In some instances, nucleic acids libraries disclosed herein have greater than 85% correct sequence compared to predetermined sequences for the nucleic acids following an amplification reaction. In some instances, nucleic acids libraries disclosed herein have greater than 90% correct sequence compared to predetermined sequences for the nucleic acids following an amplification reaction. In some instances, nucleic acids libraries disclosed herein have greater than 95% correct sequence compared to predetermined sequences for the nucleic acids following an amplification reaction. In some instances, nucleic acids libraries disclosed herein have 100% correct sequence compared to predetermined sequences for the nucleic acids following an amplification reaction.

Provided herein are nucleic acid libraries having high uniformity following amplification. In some instances, more than 80% of nucleic acids are represented within at least about 1.5× the mean representation for the entire library following amplification. In some instances, more than 90% of nucleic acids described herein are represented within at least about 1.5× the mean representation for the entire library following amplification. In some instances, more than 80% of nucleic acids are represented within at least about 2× the mean representation for the entire library following amplification. In some instances, more than 80% of nucleic acids are represented within at least about 2× the mean representation for the entire library following amplification.

Systems for Nucleic Acid Sequence Assembly

Polynucleotide Synthesis

Figure 7:
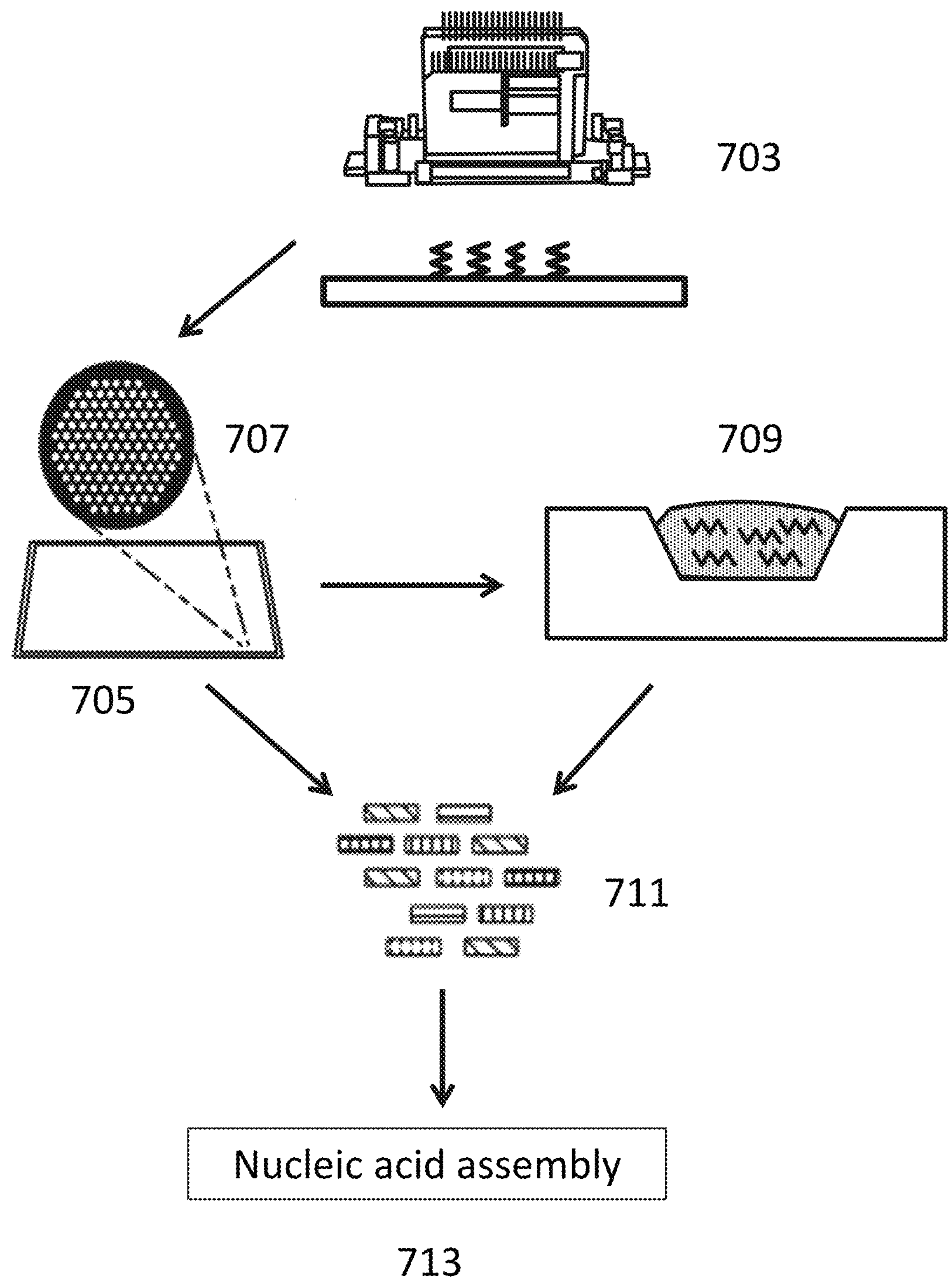
FIG. 7 depicts systems for polynucleotide synthesis and nucleic acid assembly.

Provided herein are methods for barcode nucleic acid sequence assembly of nucleic acids following generation of polynucleotides by de novo synthesis by methods described herein. An exemplary workflow is seen in FIG. 7. A computer readable input file comprising a nucleic acid sequence is received. A computer processes the nucleic acid sequence to generate instructions for synthesis of the polynucleotide sequence or a plurality of polynucleotide sequences collectively encoding the nucleic acid sequence. Instructions are transmitted to a material deposition device 703 for synthesis of the plurality of polynucleotides based on the plurality of nucleic acid sequences. The material deposition device 703, such as a polynucleotide acid synthesizer, is designed to release reagents in a step wise fashion such that multiple polynucleotides extend, in parallel, one residue at a time to generate oligomers with a predetermined nucleic acid sequence. The material deposition device 703 generates oligomers on an array 705 that includes multiple clusters 707 of loci for polynucleotide acid synthesis and extension. However, the array need not have loci organized in clusters. For example, the loci can be uniformly spread across the array. De novo polynucleotides are synthesized and removed from the plate and an assembly reaction commenced in a collection chamber 709 followed by formation population of longer polynucleotides 711. The collection chamber may comprise a sandwich of multiple surfaces (e.g., a top and bottom surface) or well or channel in containing transferred material from the synthesis surface. De novo polynucleotides can also be synthesized and removed from the plate to form a population of longer polynucleotides 711. The population of longer polynucleotides 711 can then be partitioned into droplets or subject to PCR. The population of longer polynucleotides 711 is then subject to nucleic acid assembly 713. In some instances, nucleic acid assembly comprises variant homology sequences. In some instances, nucleic acid assembly comprises paired variant assembly using paired homology sequences. In some instances, the paired variant assembly comprises a barcode. In some instances, the barcode is exposed by a restriction endonuclease such as a Type IIS restriction endonuclease.

Provided herein are systems for sequence assembly of nucleic acids following generation of polynucleotides by de novo synthesis by methods described herein. In some instances, the system comprises a computer, a material deposition device, a surface, and a nucleic acid assembly surface. In some instances, the computer comprises a readable input file with a nucleic acid sequence. In some instances, the computer processes the nucleic acid sequence to generate instructions for synthesis of the polynucleotide sequence or a plurality of polynucleotide sequences collectively encoding for the nucleic acid sequence. In some instances, the computer provides instructions to the material deposition device for the synthesis of the plurality of polynucleotide acid sequences. In some instances, the material deposition device deposits nucleosides on the surface for an extension reaction. In some instances, the surface comprises a locus for the extension reaction. In some instances, the locus is a spot, well, microwell, channel, or post. In some instances, the plurality of polynucleotide acid sequences is synthesized following the extension reaction. In some instances, the plurality of polynucleotide acid sequences is removed from the surface and prepared for nucleic acid assembly. In some instances, the nucleic acid assembly comprises barcode immunoglobulin sequence assembly.

Provided herein are methods for polynucleotide synthesis involving phosphoramidite chemistry. In some instances, polynucleotide synthesis comprises coupling a base with phosphoramidite. In some instances, polynucleotide synthesis comprises coupling a base by deposition of phosphoramidite under coupling conditions, wherein the same base is optionally deposited with phosphoramidite more than once, i.e., double coupling. In some instances, polynucleotide synthesis comprises capping of unreacted sites. In some cases, capping is optional. In some instances, polynucleotide synthesis comprises oxidation. In some instances, polynucleotide synthesis comprises deblocking or detritylation. In some instances, polynucleotide synthesis comprises sulfurization. In some cases, polynucleotide synthesis comprises either oxidation or sulfurization. In some instances, between one or each step during a polynucleotide synthesis reaction, the substrate is washed, for example, using tetrazole or acetonitrile. Time frames for any one step in a phosphoramidite synthesis method include less than about 2 min, 1 min, 50 sec, 40 sec, 30 sec, 20 sec or 10 sec.

Polynucleotide synthesis using a phosphoramidite method comprises the subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the substrate is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

In some instances, following addition of a nucleoside phosphoramidite, and optionally after capping and one or more wash steps, the substrate bound growing nucleic acid is oxidized. The oxidation step comprises oxidation of the phosphite triester into a tetracoordinated phosphate triester, a protected precursor of the naturally occurring phosphate diester internucleoside linkage. In some cases, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the substrate bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the invention described herein provide for controlled deblocking conditions limiting undesired depurination reactions. In some cases, the substrate bound polynucleotide is washed after deblocking. In some cases, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some cases, one or more wash steps precede or follow one or all of the steps.

Methods for phosphoramidite based polynucleotide synthesis comprise a series of chemical steps. In some instances, one or more steps of a synthesis method involve reagent cycling, where one or more steps of the method comprise application to the substrate of a reagent useful for the step. For example, reagents are cycled by a series of liquid deposition and vacuum drying steps. For substrates comprising three-dimensional features such as wells, microwells, channels and the like, reagents are optionally passed through one or more regions of the substrate via the wells and/or channels.

Polynucleotides synthesized using the methods and/or substrates described herein comprise at least about 20, 30, 40, 50, 60, 70, 75, 80, 90, 100, 120, 150, 200, 500 or more bases in length. In some instances, at least about 1 pmol, 10 pmol, 20 pmol, 30 pmol, 40 pmol, 50 pmol, 60 pmol, 70 pmol, 80 pmol, 90 pmol, 100 pmol, 150 pmol, 200 pmol, 300 pmol, 400 pmol, 500 pmol, 600 pmol, 700 pmol, 800 pmol, 900 pmol, 1 nmol, 5 nmol, 10 nmol, 100 nmol or more of an polynucleotide is synthesized within a locus. Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on a substrate. For example, a substrate comprising about or at least about 100; 1,000; 10,000; 100,000; 1,000,000; 2,000,000; 3,000,000; 4,000,000; or 5,000,000 resolved loci is able to support the synthesis of at least the same number of distinct polynucleotides, wherein a polynucleotide encoding a distinct sequence is synthesized on a resolved locus.

Various suitable methods are known for generating high density polynucleotide arrays. In an exemplary workflow, a substrate surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes a single nucleotide extension process to extend multiple oligomers in parallel. A deposition device, such as a polynucleotide synthesizer, is designed to release reagents in a step wise fashion such that multiple polynucleotides extend, in parallel, one residue at a time to generate oligomers with a predetermined nucleic acid sequence. In some cases, polynucleotides are cleaved from the surface at this stage. Cleavage includes gas cleavage, e.g., with ammonia or methylamine.

Substrates

Devices used as a surface for polynucleotide synthesis may be in the form of substrates which include, without limitation, homogenous array surfaces, patterned array surfaces, channels, beads, gels, and the like. Provided herein are substrates comprising a plurality of clusters, wherein each cluster comprises a plurality of loci that support the attachment and synthesis of polynucleotides. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus is on a three-dimensional surface, e.g., a well, microwell, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some cases, a surface of a substrate is inclusive of one or a plurality of surfaces of a substrate. The average error rates for polynucleotides synthesized within a library described here using the systems and methods provided are often less than 1 in 1000, less than about 1 in 2000, less than about 1 in 3000 or less often without error correction.

Provided herein are surfaces that support the parallel synthesis of a plurality of polynucleotides having different predetermined sequences at addressable locations on a common support. In some instances, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the surfaces provide support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the substrate provides a surface environment for the growth of polynucleotides having at least 80, 90, 100, 120, 150, 175, 200, 225, 250, 275, 300, 325, 350, 375, 400, 425, 450, 475, 500 bases or more.

Provided herein are methods for polynucleotide synthesis on distinct loci of a substrate, wherein each locus supports the synthesis of a population of polynucleotides. In some cases, each locus supports the synthesis of a population of polynucleotides having a different sequence than a population of polynucleotides grown on another locus. In some instances, each polynucleotide sequence is synthesized with 1, 2, 3, 4, 5, 6, 7, 8, 9 or more redundancy across different loci within the same cluster of loci on a surface for polynucleotide synthesis. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a substrate comprises about 10,000 distinct loci. The amount of loci within a single cluster is varied in different instances. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci.

In some instances, the number of distinct polynucleotides synthesized on a substrate is dependent on the number of distinct loci available on the substrate. In some instances, the density of loci within a cluster of a substrate is at least or about 1, 10, 25, 50, 65, 75, 100, 130, 150, 175, 200, 300, 400, 500, 1,000 or more loci per $mm^2$. In some cases, a substrate comprises 10-500, 25-400, 50-500, 100-500, 150-500, 10-250, 50-250, 10-200, or 50-200 $mm^2$. In some instances, the distance between the centers of two adjacent loci within a cluster is from about 10-500, from about 10-200, or from about 10-100 um. In some instances, the distance between two centers of adjacent loci is greater than about 10, 20, 30, 40, 50, 60, 70, 80, 90 or 100 um. In some instances, the distance between the centers of two adjacent loci is less than about 200, 150, 100, 80, 70, 60, 50, 40, 30, 20 or 10 um. In some instances, each locus independently has a width of about 0.5, 1, 2, 3, 4, 5, 6, 7, 8, 9, 10, 20, 30, 40, 50, 60, 70, 80, 90 or 100 um. In some cases, each locus independently has a width of about 0.5-100, 0.5-50, 10-75, or 0.5-50 um.

In some instances, the density of clusters within a substrate is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a substrate comprises from about 1 cluster per 10 $mm^2$ to about 10 clusters per 1 $mm^2$. In some instances, the distance between the centers of two adjacent clusters is at least or about 50, 100, 200, 500, 1000, 2000, or 5000 um. In some cases, the distance between the centers of two adjacent clusters is between about 50-100, 50-200, 50-300, 50-500, or 100-2000 um. In some cases, the distance between the centers of two adjacent clusters is between about 0.05-50, 0.05-10, 0.05-5, 0.05-4, 0.05-3, 0.05-2, 0.1-10, 0.2-10, 0.3-10, 0.4-10, 0.5-10, 0.5-5, or 0.5-2 mm. In some cases, each cluster independently has a cross section of about 0.5 to 2, about 0.5 to 1, or about 1 to 2 mm. In some cases, each cluster independently has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster independently has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some instances, a substrate is about the size of a standard 96 well plate, for example between about 100 to about 200 mm by between about 50 to about 150 mm. In some instances, a substrate has a diameter less than or equal to about 1000, 500, 450, 400, 300, 250, 200, 150, 100 or 50 mm. In some instances, the diameter of a substrate is between about 25-1000, 25-800, 25-600, 25-500, 25-400, 25-300, or 25-200 mm. In some instances, a substrate has a planar surface area of at least about 100; 200; 500; 1,000; 2,000; 5,000; 10,000; 12,000; 15,000; 20,000; 30,000; 40,000; 50,000 $mm^2$ or more. In some instances, the thickness of a substrate is between about 50-2000, 50-1000, 100-1000, 200-1000, or 250-1000 mm.

Surface Materials

Substrates, devices, and reactors provided herein are fabricated from any variety of materials suitable for the methods, compositions, and systems described herein. In certain instances, substrate materials are fabricated to exhibit a low level of nucleotide binding. In some instances, substrate materials are modified to generate distinct surfaces that exhibit a high level of nucleotide binding. In some instances, substrate materials are transparent to visible and/or UV light. In some instances, substrate materials are sufficiently conductive, e.g., are able to form uniform electric fields across all or a portion of a substrate. In some instances, conductive materials are connected to an electric ground. In some instances, the substrate is heat conductive or insulated. In some instances, the materials are chemical resistant and heat resistant to support chemical or biochemical reactions, for example polynucleotide synthesis reaction processes. In some instances, a substrate comprises flexible materials. For flexible materials, materials can include, without limitation: nylon, both modified and unmodified, nitrocellulose, polypropylene, and the like. In some instances, a substrate comprises rigid materials. For rigid materials, materials can include, without limitation: glass; fuse silica; silicon, plastics (for example polytetrafluoroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Architecture

Provided herein are substrates for the methods, compositions, and systems described herein, wherein the substrates have a surface architecture suitable for the methods, compositions, and systems described herein. In some instances, a substrate comprises raised and/or lowered features. One benefit of having such features is an increase in surface area to support polynucleotide synthesis. In some instances, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as a polynucleotide synthesizer. In some cases, reagents and/or fluids collect in a larger well in fluid communication with one or more channels. For example, a substrate comprises a plurality of channels corresponding to a plurality of loci within a cluster, and the plurality of channels are in fluid communication with one well of the cluster. In some methods, a library of polynucleotides is synthesized in a plurality of loci of a cluster.

Provided herein are substrates for the methods, compositions, and systems described herein, wherein the substrates are configured for polynucleotide synthesis. In some instances, the structure is configured to allow for controlled flow and mass transfer paths for polynucleotide synthesis on a surface. In some instances, the configuration of a substrate allows for the controlled and even distribution of mass transfer paths, chemical exposure times, and/or wash efficacy during polynucleotide synthesis. In some instances, the configuration of a substrate allows for increased sweep efficiency, for example by providing sufficient volume for growing a polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are substrates for the methods, compositions, and systems relating to enzymatic mediated nucleic acid assembly and polynucleotide synthesis described herein, wherein the substrates comprise structures configured for housing enzymatic reactions described herein. In some instances, segregation is achieved by physical structure. In some instances, segregation is achieved by differential functionalization of the surface generating active and passive regions for polynucleotide synthesis. In some instances, differential functionalization is achieved by alternating the hydrophobicity across the substrate surface, thereby creating water contact angle effects that cause beading or wetting of the deposited reagents. Employing larger structures can decrease splashing and cross-contamination of distinct polynucleotide synthesis locations with reagents of the neighboring spots. In some cases, a device, such as a polynucleotide synthesizer, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000; 1:3,000; 1:5,000; or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a substrate may have the same or different width, height, and/or volume as another well of the substrate. A channel of a substrate may have the same or different width, height, and/or volume as another channel of the substrate. In some instances, the diameter of a cluster or the diameter of a well comprising a cluster, or both, is between about 0.05-50, 0.05-10, 0.05-5, 0.05-4, 0.05-3, 0.05-2, 0.05-1, 0.05-0.5, 0.05-0.1, 0.1-10, 0.2-10, 0.3-10, 0.4-10, 0.5-10, 0.5-5, or 0.5-2 mm. In some instances, the diameter of a cluster or well or both is less than or about 5, 4, 3, 2, 1, 0.5, 0.1, 0.09, 0.08, 0.07, 0.06, or 0.05 mm. In some instances, the diameter of a cluster or well or both is between about 1.0 and about 1.3 mm. In some instances, the diameter of a cluster or well, or both is about 1.150 mm. In some instances, the diameter of a cluster or well, or both is about 0.08 mm. The diameter of a cluster refers to clusters within a two-dimensional or three-dimensional substrate.

In some instances, the height of a well is from about 20-1000, 50-1000, 100-1000, 200-1000, 300-1000, 400-1000, or 500-1000 um. In some cases, the height of a well is less than about 1000, 900, 800, 700, or 600 um.

In some instances, a substrate comprises a plurality of channels corresponding to a plurality of loci within a cluster, wherein the height or depth of a channel is 5-500, 5-400, 5-300, 5-200, 5-100, 5-50, or 10-50 um. In some cases, the height of a channel is less than 100, 80, 60, 40, or 20 um.

In some instances, the diameter of a channel, locus (e.g., in a substantially planar substrate) or both channel and locus (e.g., in a three-dimensional substrate wherein a locus corresponds to a channel) is from about 1-1000, 1-500, 1-200, 1-100, 5-100, or 10-100 um, for example, about 90, 80, 70, 60, 50, 40, 30, 20 or 10 um. In some instances, the diameter of a channel, locus, or both channel and locus is less than about 100, 90, 80, 70, 60, 50, 40, 30, 20 or 10 um. In some instances, the distance between the center of two adjacent channels, loci, or channels and loci is from about 1-500, 1-200, 1-100, 5-200, 5-100, 5-50, or 5-30, for example, about 20 um.

Surface Modifications

Provided herein are methods for polynucleotide synthesis on a surface, wherein the surface comprises various surface modifications. In some instances, the surface modifications are employed for the chemical and/or physical alteration of a surface by an additive or subtractive process to change one or more chemical and/or physical properties of a substrate surface or a selected site or region of a substrate surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some instances, a substrate surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a substrate surface is modified with one or more different layers of compounds. Such modification layers of interest include, without limitation, inorganic and organic layers such as metals, metal oxides, polymers, small organic molecules and the like.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in a polynucleotide acid synthesis reaction. The surface energy, or hydrophobicity, of a surface is a factor for determining the affinity of a nucleotide to attach onto the surface. In some instances, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. Methods and functionalizing agents are described in U.S. Pat. No. 5,474,796, which is herein incorporated by reference in its entirety.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions.

Computer Systems

Any of the systems described herein, may be operably linked to a computer and may be automated through a computer either locally or remotely. In some instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. The computer systems may be programmed to interface between the user specified base sequence and the position of a material deposition device to deliver the correct reagents to specified regions of the substrate.

Figure 8:
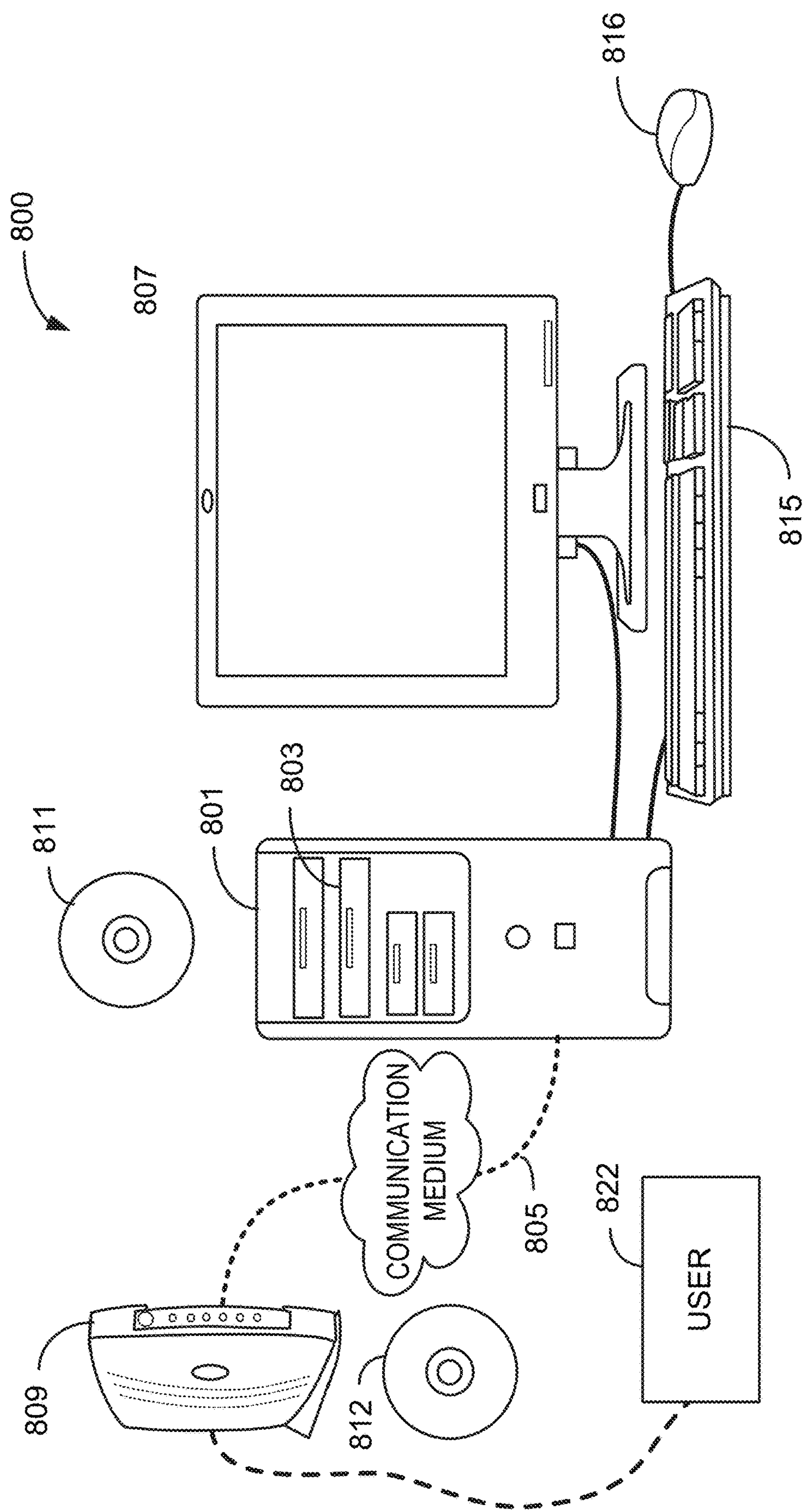
FIG. 8 illustrates a computer system.

The computer system 800 illustrated in FIG. 8 may be understood as a logical apparatus that can read instructions from media 811 and/or a network port 805, which can optionally be connected to server 809 having fixed media 812. The system, such as shown in FIG. 8, can include a CPU 801, disk drives 803, optional input devices such as a keyboard 815 and/or mouse 816 and optional monitor 807. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 822 as illustrated in FIG. 8.

Figure 9:
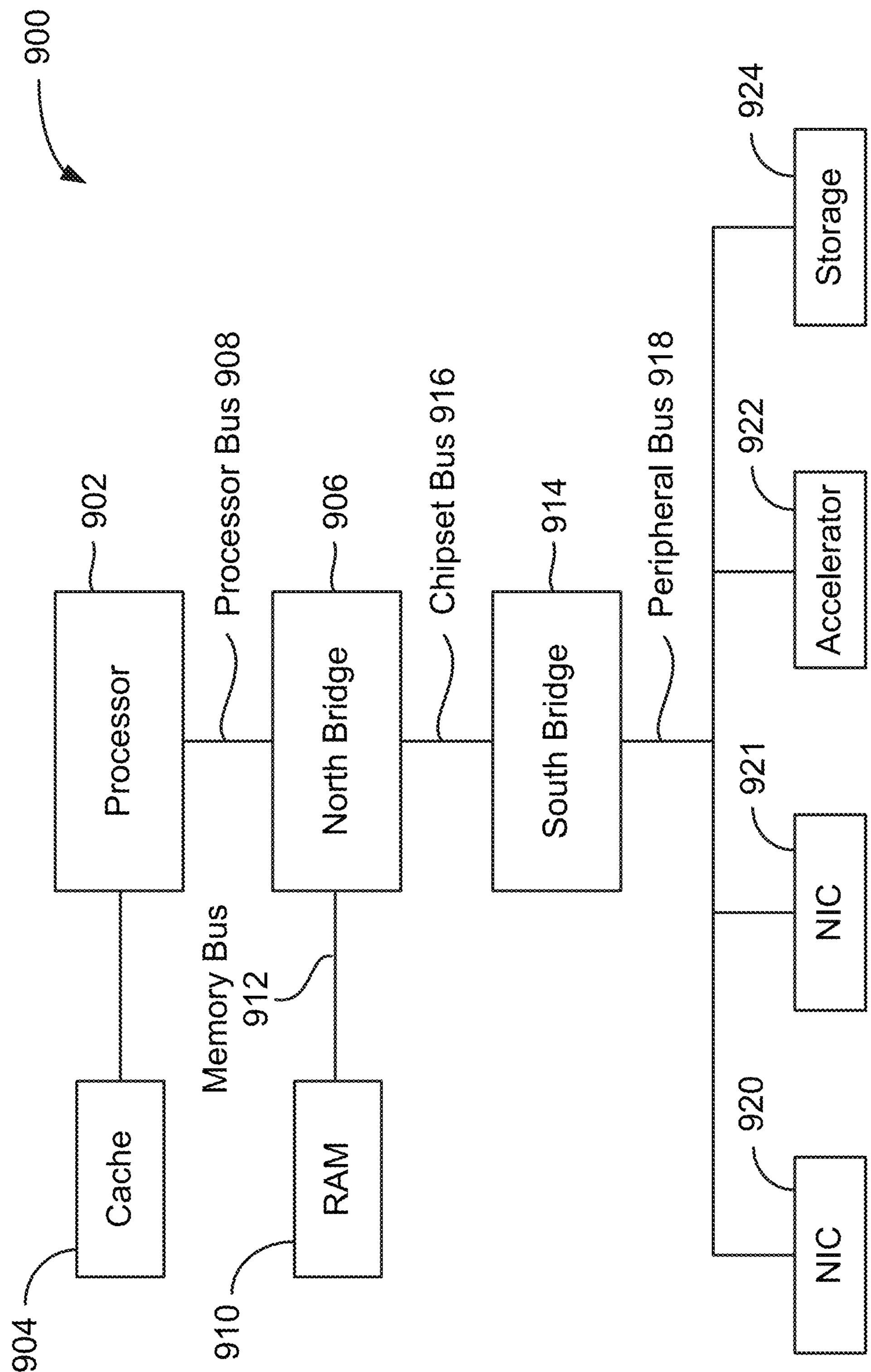
FIG. 9 is a block diagram illustrating architecture of a computer system.

FIG. 9 is a block diagram illustrating architecture of a computer system 900 that can be used in connection with example embodiments of the present invention. As depicted in FIG. 9, the example computer system can include a processor 902 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 9, a high speed cache 904 can be connected to, or incorporated in, the processor 902 to provide a high speed memory for instructions or data that have been recently, or are frequently, used by processor 902. The processor 902 is connected to a north bridge 906 by a processor bus 908. The north bridge 906 is connected to random access memory (RAM) 910 by a memory bus 912 and manages access to the RAM 910 by the processor 902. The north bridge 906 is also connected to a south bridge 914 by a chipset bus 916. The south bridge 914 is, in turn, connected to a peripheral bus 918. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 918. In some alternative architectures, the functionality of the north bridge can be incorporated into the processor instead of using a separate north bridge chip. In some instances, system 900 can include an accelerator card 922 attached to the peripheral bus 918. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 924 and can be loaded into RAM 910 and/or cache 904 for use by the processor. The system 900 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention. In this example, system 900 also includes network interface cards (NICs) 920 and 921 connected to the peripheral bus for providing network interfaces to external storage, such as Network Attached Storage (NAS) and other computer systems that can be used for distributed parallel processing.

Figure 10:
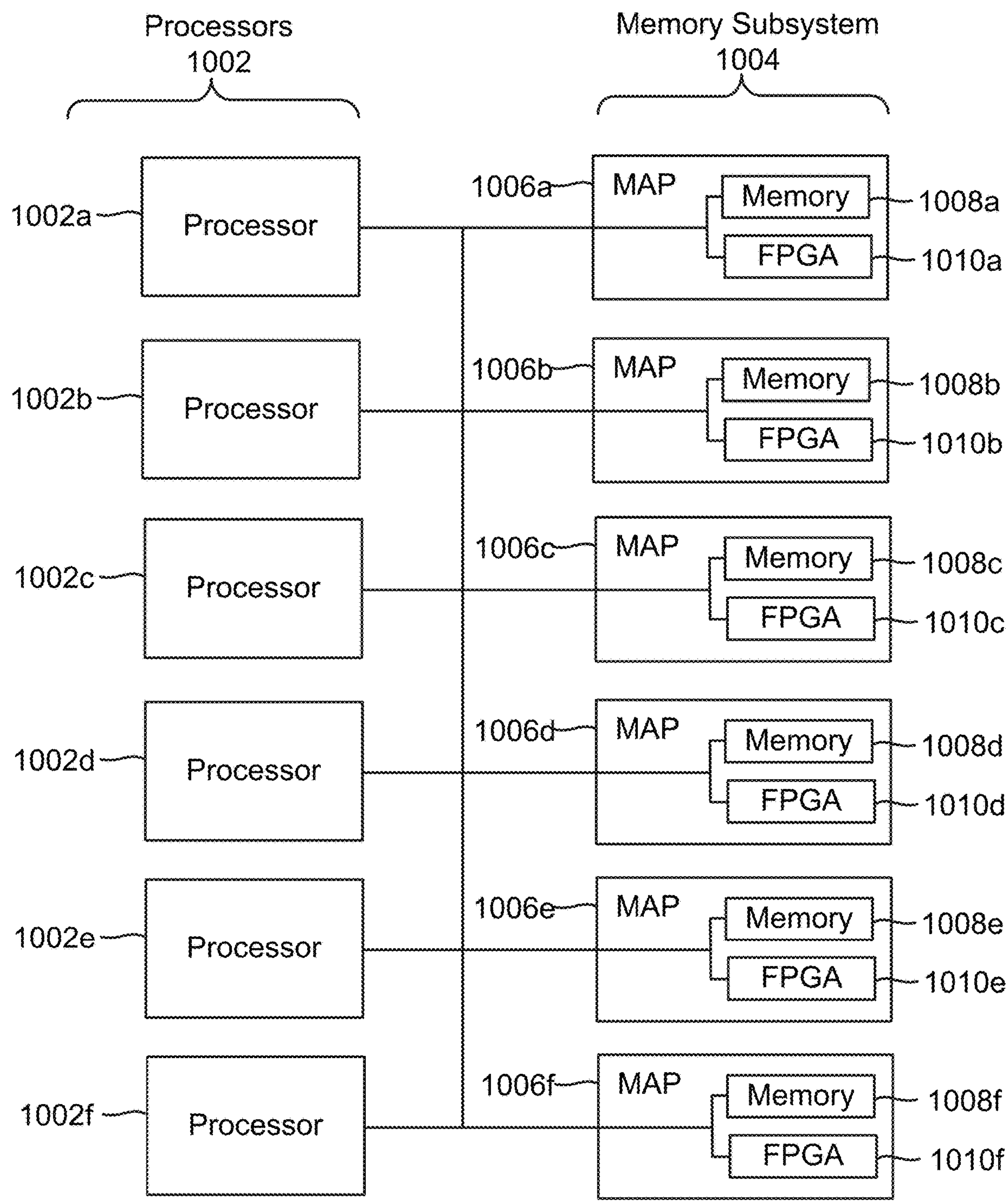
FIG. 10 is a block diagram of a multiprocessor computer system using a shared virtual address memory space.

FIG. 10 is a block diagram of a multiprocessor computer system using a shared virtual address memory space in accordance with an example embodiment. The system includes a plurality of processors 1002*a-f* that can access a shared memory subsystem 1004. The system incorporates a plurality of programmable hardware memory algorithm processors (MAPs) 1006*a-f* in the memory subsystem 1004. Each MAP 1006*a-f* can comprise a memory 1008*a-f* and one or more field programmable gate arrays (FPGAs) 1010*a-f*. The MAP provides a configurable functional unit and particular algorithms or portions of algorithms can be provided to the FPGAs 1010*a-f* for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1008*a-f*, allowing it to execute tasks independently of, and asynchronously from, the respective microprocessor 1002*a-f*. In this configuration, a MAP can feed results directly to another MAP for pipelining and parallel execution of algorithms.

Figure 11:
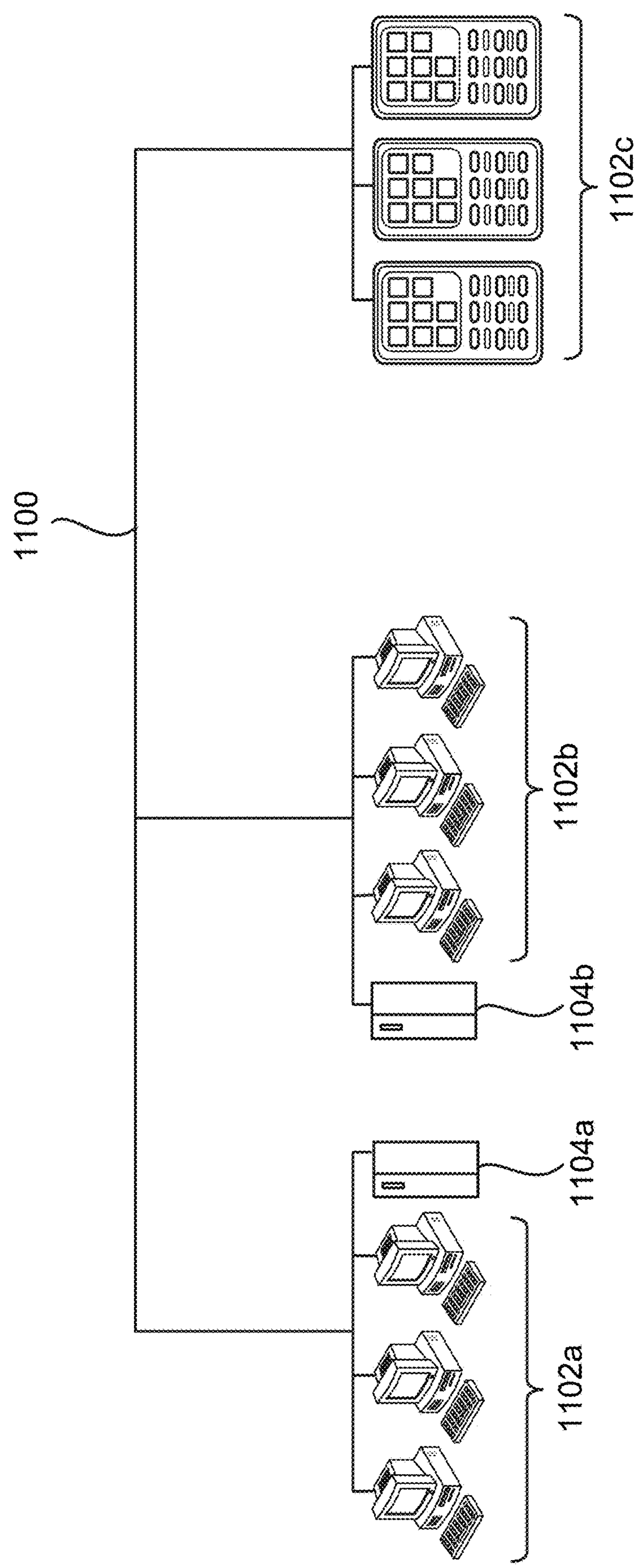
FIG. 11 is a diagram demonstrating a network configured to incorporate a plurality of computer systems, a plurality of cell phones and personal data assistants, and Network Attached Storage (NAS).

FIG. 11 is a diagram showing a network with a plurality of computer systems 1102*a* and 1102*b*, a plurality of cell phones and personal data assistants 1102*c*, and Network Attached Storage (NAS) 1104*a* and 1104*b*. In example embodiments, systems 1102*a*, 1102*b*, and 1102*c* can manage data storage and optimize data access for data stored in Network Attached Storage (NAS) 1104*a* and 1104*b*. A mathematical model can be used for the data and be evaluated using distributed parallel processing across computer systems 1102*a* and 1102*b*, and cell phone and personal data assistant systems 1102*c*. Computer systems 1102*a* and 1102*b*, and cell phone and personal data assistant systems 1102*c* can also provide parallel processing for adaptive data restructuring of the data stored in Network Attached Storage (NAS) 1104*a* and 1104*b*. FIG. 11 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some instances, processors can maintain separate memory spaces and transmit data through network interfaces, back plane or other connectors for parallel processing by other processors. In some instances, some or all of the processors can use a shared virtual address memory space.

Any of the systems described herein may comprise sequence information stored on non-transitory computer readable storage media. In some instances, any of the systems described herein comprise a computer input file. In some instances, the computer input file comprises sequence information. In some instances, the computer input file comprises instructions for synthesis of a plurality of polynucleotide sequences. In some instances, the instructions are received by a computer. In some instances, the instructions are processed by the computer. In some instances, the instructions are transmitted to a material deposition device. In some instances, the non-transitory computer readable storage media is encoded with a program including instructions executable by the operating system of an optionally networked digital processing device. In some instances, a computer readable storage medium is a tangible component of a digital processing device. In some instances, a computer readable storage medium is optionally removable from a digital processing device. In some instances, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Functionalization of a Substrate Surface

A substrate was functionalized to support the attachment and synthesis of a library of polynucleotides. The substrate surface was first wet cleaned using a piranha solution comprising 90% $H_2SO_4$ and 10% $H_2O_2$ for 20 minutes. The substrate was rinsed in several beakers with deionized water, held under a deionized water gooseneck faucet for 5 min, and dried with $N_2$. The substrate was subsequently soaked in $NH_4OH$ (1:100; 3 mL:300 mL) for 5 min, rinsed with DI water using a handgun, soaked in three successive beakers with deionized water for 1 min each, and then rinsed again with deionized water using the handgun. The substrate was then plasma cleaned by exposing the substrate surface to $O_2$. A SAMCO PC-300 instrument was used to plasma etch $O_2$ at 250 watts for 1 min in downstream mode.

The cleaned substrate surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The substrate surface was resist coated using a Brewer Science 200X spin coater. SPR™ 3612 photoresist was spin coated on the substrate at 2500 rpm for 40 sec. The substrate was pre-baked for 30 min at 90° C. on a Brewer hot plate. The substrate was subjected to photolithography using a Karl Suss MA6 mask aligner instrument. The substrate was exposed for 2.2 sec and developed for 1 min in MSF 26A. Remaining developer was rinsed with the handgun and the substrate soaked in water for 5 min. The substrate was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The substrate surface was passively functionalized with a 100 μL solution of perfluorooctyltrichlorosilane mixed with 10 μL light mineral oil. The substrate was placed in a chamber, pumped for 10 min, and then the valve was closed to the pump and left to stand for 10 min. The chamber was vented to air. The substrate was resist stripped by performing two soaks for 5 min in 500 mL NMP at 70° C. with ultrasonication at maximum power (9 on Crest system). The substrate was then soaked for 5 min in 500 mL isopropanol at room temperature with ultrasonication at maximum power. The substrate was dipped in 300 mL of 200 proof ethanol and blown dry with $N_2$. The functionalized surface was activated to serve as a support for polynucleotide synthesis.

Example 2: Synthesis of a 50-mer Sequence on an Oligonucleotide Synthesis Device A two dimensional oligonucleotide synthesis device was assembled into a flowcell, which was connected to a flowcell (Applied Biosystems ("ABI394 DNA Synthesizer")). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described in SEQ ID NO.: 1. 5'AGACAATCAACCATTTGGGGTGGACAGCCTTGACCTCTAGACTTCGGCAT##TTT TTTTTTT3' (SEQ ID NO.: 1), where # denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 3 and an ABI synthesizer.

TABLE 3

| Synthesis Protocol | | |
|---|---|---|
| General DNA Synthesis Process Name | Process Step | Time (sec) |
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |

TABLE 3-continued

Synthesis Protocol

| General DNA Synthesis Process Name | Process Step | Time (sec) |
|---|---|---|
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (Cap A+B, 1:1, Flow) | Cap A + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (DeblockFlow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI394 DNA Synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and 0x (0.02M I2 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip (data not shown).

Example 3: Synthesis of a 100-mer Sequence on an Oligonucleotide Synthesis Device The same process as described in Example 2 for the synthesis of the 50-mer sequence was used for the synthesis of a 100-mer polynucleotide ("100-mer polynucleotide"; 5' CGGGATCCTTATCGTCATCGTCGTACA-GATCCCGACCCATTTGCTGTCCACCAGT CATGCTAGCCATACCATGATGATGATGATGATG-AGAACCCCGCAT##TTTTTTTTT T3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYLPROPYL)-4-HYDROXYBUTYRAMIDE and the second one functionalized with 5/95 mix of 11-acetoxyundecyltriethoxysilane and n-decyltriethoxysilane, and the polynucleotides extracted from the surface were analyzed on a BioAnalyzer instrument (data not shown).

All ten samples from the two chips were further PCR amplified using a forward (5'ATGCGGGGTTCTCATCATC3; SEQ ID NO.: 3) and a reverse (5'CGGGATCCTTATCGTCATCG3; SEQ ID NO.: 4) primer in a 50 uL PCR mix (25 uL NEB Q5 mastermix, 2.5 uL 10 uM Forward primer, 2.5 uL 10 uM Reverse primer, 1 uL polynucleotide extracted from the surface, and water up to 50 uL) using the following thermal cycling program:

98° C., 30 sec

98° C., 10 sec; 63° C., 10 sec; 72° C., 10 sec; repeat 12 cycles

72° C., 2 min

The PCR products were also run on a BioAnalyzer (data not shown), demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

Sequencing Results

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized polynucleotides were repeated on two chips with different surface chemistries. Overall, 89%, corresponding to 233 out of 262 of the 100-mers that were sequenced were perfect sequences with no errors. Table 5 summarizes error characteristics for the sequences obtained from the polynucleotides samples from spots 1-10.

TABLE 5

| Error Characteristics | | | | | | | | | | |
|---|---|---|---|---|---|---|---|---|---|---|
| Sample ID/Spot no. | OSA0046/ 1 | OSA0047/ 2 | OSA0048/ 3 | OSA0049/ 4 | OSA0050/ 5 | OSA0051/ 6 | OSA0052/ 7 | OSA0053/ 8 | OSA0054/ 9 | OSA0055/ 10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate | Err ~1 in 834 | Err ~1 in 1350 | Err ~1 in 1282 | Err: ~1 in 708 | Err: ~1 in 2500 | Err: ~1 in 2667 | Err: ~1 in 876 | Err ~1 in 2900 | Err ~1 in 1400 | Err: ~1 in 2349 |
| ROI Minus Primer Error Rate | MP Err: ~1 in 763 | MP Err: ~1 in 824 | MP Err: ~1 in 780 | MP Err: ~1 in 429 | MP Err: ~1 in 1525 | MP Err: ~1 in 1615 | MP Err: ~1 in 531 | MP Err: ~1 in 1769 | MP Err: ~1 in 854 | MP Err: ~1 in 1451 |

Example 4: Exemplary Formulations for Enzymatic Based Assembly

Various reaction conditions are seen in Tables 6-14. The reagents are added in various orders. Alternatively, the reagents are added in step wise fashion, for example, reagents are added in order listed as in Table 14.

TABLE 6

| Reaction Conditions 1 | |
|---|---|
| Reagent | Final Concentration |
| Vector | 4 nM |
| Gene Fragment 1 | 4 nM |
| dNTP | .2 mM |
| 10X Ampligase buffer | 1X |
| ExoIII | 10 U |
| Phusion | 0.2 U |
| Ampligase | 1 U |
| Fen1 | 3.2 U |
| Water | Remaining water up to 10 uL |

TABLE 7

| Reaction Conditions 2 | |
|---|---|
| Reagent | Final Concentration |
| Vector | 4 nM |
| Gene Fragment | 4 nM |
| dNTP | 0.2 mM |
| 10X Ampligase buffer | 1X |
| ExoIII | 1 U |
| Phusion | 0.2 U or 0.1 U |
| Ampligase | 1 U |

TABLE 7-continued

| Reaction Conditions 2 | |
|---|---|
| Reagent | Final Concentration |
| Fen1 | 0.32 U |
| Water | Remaining water up to 10 uL |

TABLE 8

| Enzyme Concentrations | |
|---|---|
| | Reaction Condition |
| 1 | 0.32 U Fen1<br>1 U ExoIII<br>0.2 U Phusion<br>1 U Ampligase |
| 2 | 0.32 U Fen1<br>1 U ExoIII<br>0.1 U Phusion<br>0.5 U Ampligase |
| 3 | 0.32 U Fen1<br>1 U ExoIII<br>0.1 U Phusion<br>1.0 U Ampligase |
| 4 | 0.32 U Fen1<br>1 U ExoIII<br>0.05 U Phusion<br>1.0 U Ampligase |
| 5 | 0.32 U Fen1<br>1.5 U ExoIII<br>0.2 U Phusion<br>1.0 U Ampligase |
| 6 | 4.8 U Fen1<br>1.0 U ExoIII<br>0.2 U Phusion<br>1.0 U Ampligase |
| 7 | 0.32 U Fen1<br>0.5 U ExoIII<br>0.05 U Phusion<br>1.0 U Ampligase |

TABLE 8-continued

| Enzyme Concentrations | |
|---|---|
| | Reaction Condition |
| 8 | 0.32 U Fen1<br>1.0 U ExoIII<br>0.1 U Phusion<br>0.1 U Ampligase |
| 9 | 0.32 U Fen1<br>1.0 U ExoIII<br>0.1 U Phusion<br>0.25 U Ampligase |
| 10 | 0.32 U Fen1<br>1.0 U ExoIII<br>0.2 U Phusion<br>0.5 U Ampligase |
| 11 | 0.32 U Fen1<br>1.0 U ExoIII<br>0.2 U Phusion<br>0.25 U Ampligase |
| 12 | 0.32 U Fen1<br>0.5 U ExoIII<br>0.1 U Phusion<br>1.0 U Ampligase |
| 13 | 3.2 U Fen1<br>1.0 U ExoIII<br>0.2 U Phusion<br>1.0 U Ampligase |
| 14 | 0.32 U Fen1<br>0.5 U ExoIII<br>0.2 U Phusion<br>1.0 U Ampligase |
| 15 | 0.32 U Fen1<br>1.5 U ExoIII<br>0.1 U Phusion<br>1.0 U Ampligase |
| 16 | 0.32 U Fen1<br>1.5 U ExoIII<br>0.05 U Phusion<br>1.0 U Ampligase |
| 17 | 3.2 U Fen1<br>0.5 U ExoIII<br>0.2 U Phusion<br>0.5 U Ampligase |
| 18 | 3.2 U Fen1<br>1.0 U ExoIII<br>0.2 U Phusion<br>0.5 U Ampligase |
| 19 | 3.2 U Fen1<br>1.0 U ExoIII<br>0.2 U Phusion<br>0 U Ampligase |
| 20 | 4.8 U Fen1<br>0.5 U ExoIII<br>0.2 U Phusion<br>1.0 U Ampligase |
| 21 | 0.32 U Fen1<br>1.5 U ExoIII<br>0.5 U Phusion<br>1.0 U Ampligase |
| 22 | 3.2 U Fen1<br>0.5 U ExoIII<br>0.2 U Phusion<br>1.0 U Ampligase |
| 23 | 0.32 U Fen1<br>1.0 U ExoIII<br>0.2 U Phusion<br>0.1 U Ampligase |
| 24 | 0.32 U Fen1<br>0.5 U ExoIII<br>0.5 U Phusion<br>1.0 U Ampligase |
| 25 | 0.32 U Fen1<br>1.0 U ExoIII<br>0.5 U Phusion<br>1.0 U Ampligase |
| 26 | 3.2 U Fen1<br>10.0 U ExoIII<br>0.2 U Phusion<br>1.0 U Ampligase |
| 27 | 3.2 U Fen1<br>5.0 U ExoIII<br>0.2 U Phusion<br>1.0 U Ampligase |

TABLE 9

Method 1 Reaction Concentrations

| Reagent | 5 uL reaction | Final Concentration |
|---|---|---|
| dNTP (10 mM) | 0.1 | .2 mM |
| 10x Ampligase buffer | 0.5 | 1X |
| ExoIII (100 U/uL) | 0.005 | 0.1 U/uL |
| Phusion (2 U/uL) | 0.05 | 0.02 U/uL |
| Ampligase (5 U/uL) | 0.1 | 0.1 U/uL |
| Fen1 (32 U/uL) | 0.005 | 0.032 U/uL |
| Vector DNA | | 20 fmol |
| Insert DNA | | 40 fmol/Insert |
| Water * | To 5 uL | |

TABLE 10

Method 2 Reaction Concentrations

| Reagent | 5 uL reaction | Final Concentration |
|---|---|---|
| dNTP (10 mM) | 0.1 | .2 mM |
| 10x Ampligase buffer | 0.5 | 1x |
| ExoIII 100 U/uL | 0.08 | 1.6 U/uL |
| Phusion 2 U/uL | 0.05 | 0.02 U/uL |
| Ampligase 5 U/uL | 0.1 | 0.1 U/uL |
| Fen1 32 U/uL | 0.005 | 0.032 U/uL |
| Vector DNA | | 20 fmol |
| Insert DNA | | 40 fmol/Insert |
| Water * | To 5 uL | |

TABLE 11

Method 3 Reaction Conditions

| Master Mix | 5 uL reaction | Final Concentration |
|---|---|---|
| dNTP | 0.1 | .4 mM |
| 10x Ampligase buffer (Epicenter) | 0.5 | 2x |
| ExoIII 100 U/uL (NEB) | 0.08 | 1.6 U/uL |
| Phusion 2 U/uL (NEB) | 0.005 | 0.002 U/uL |
| Ampligase 5 U/uL (Epicenter) | 0.1 | 0.1 U/uL |
| Fen1 32 U/uL (NEB) | 0.005 | 0.032 U/uL |
| Water * | 1.695 | |

TABLE 12

| Method 4 Reaction Conditions | | |
|---|---|---|
| Master Mix | 50 ul reaction | Final Concentration (for 2x MM) |
| ExoII 100 U/uL | 0.05 | 0.2 U/uL |
| Phusion 2 U/uL | 0.05 | 0.004 U/uL |
| Fen1 32 U/uL | 0.05 | 0.064 U/uL |
| dNTP | 1 | .4 mM |
| Ampligase 5 U/uL | 1 | 0.2 U/uL |
| 10x Ampligase buffer | 5 | 2x |
| Water * | | |

TABLE 13

| Method 5 Reaction Conditions | | | |
|---|---|---|---|
| Stepwise addition step | Component | Final Concentration (for 2x MM) | Volume for 250 uL Master Mix |
| 1 | Water | | 179.75 |
| 2 | 10x Taq HiFi DNA ligase buffer | 2x | 50 |
| 3 | dNTP | .4 mM | 10 |
| 4 | ExoIII 100 U/uL | 3.2 U/uL | 8 |
| 5 | Phusion 2 U/uL | 0.004 U/uL | 0.5 |
| 6 | Taq DNA ligase 40 U/uL | 0.2 U/uL | 1.25 |
| 7 | Fen1 32 U/uL | 0.064 U/uL | 0.5 |

TABLE 14

| Reaction Conditions | |
|---|---|
| Component | Final Concentration (for 2x MM) |
| Water | |
| 10x Taq HIFI DNA ligase buffer | 0.5-5x |
| dNTP | 0.1-1.0 mM |
| ExoIII 100 U/uL | 0.8-8 U/uL |
| Phusion 2 U/uL | 0.001-0.01 U/uL |
| Taq DNA ligase 40 U/uL | 0.05-5.0 U/uL |
| Fen1 32 U/uL | 0.01-0.1 U/uL |

Example 5: Enzymatic Mediated Nucleic Acid Assembly

Figure 12A:
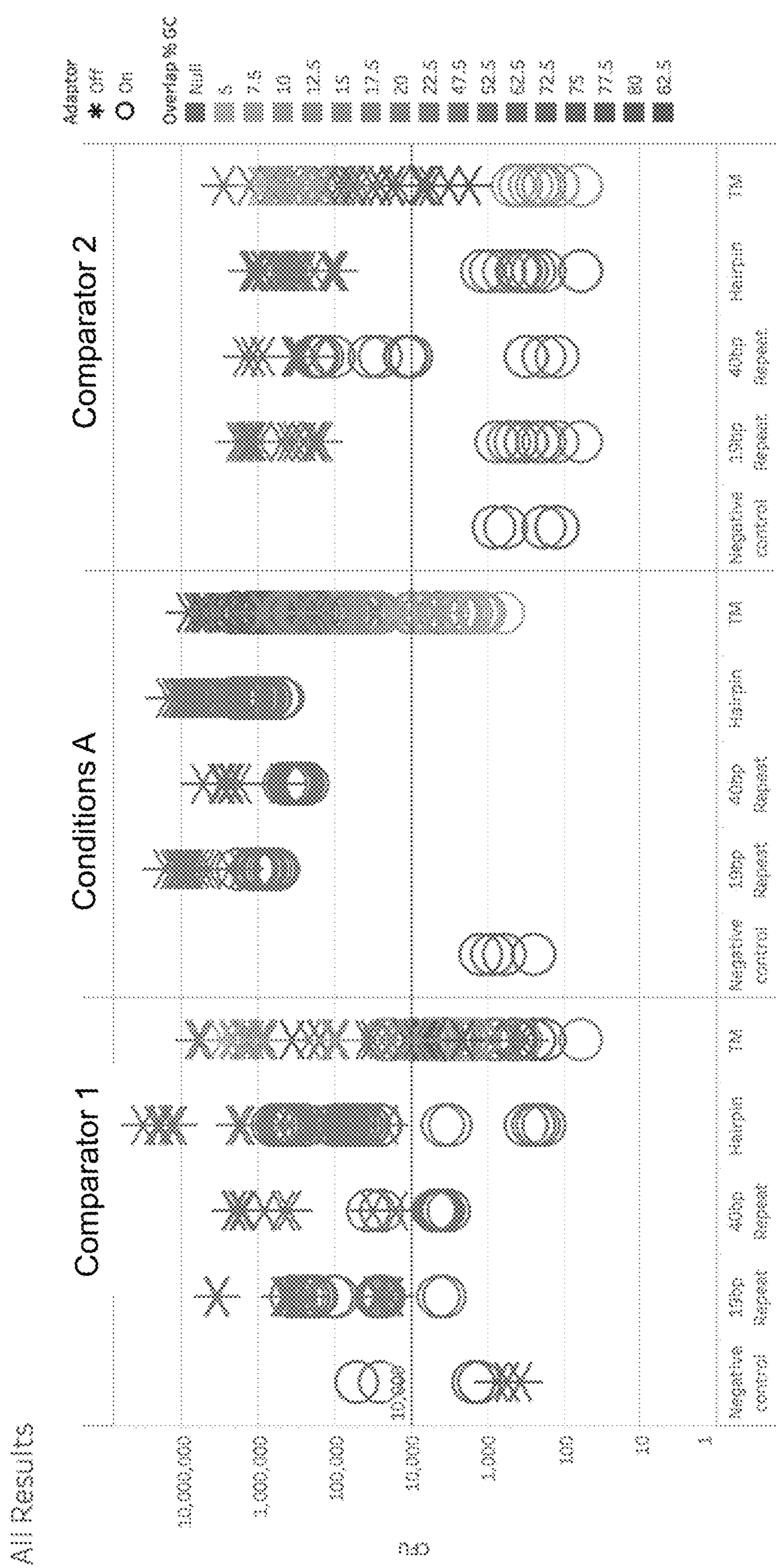
FIG. 12A is a graph of colony forming units (CFUs).
Figure 12B:
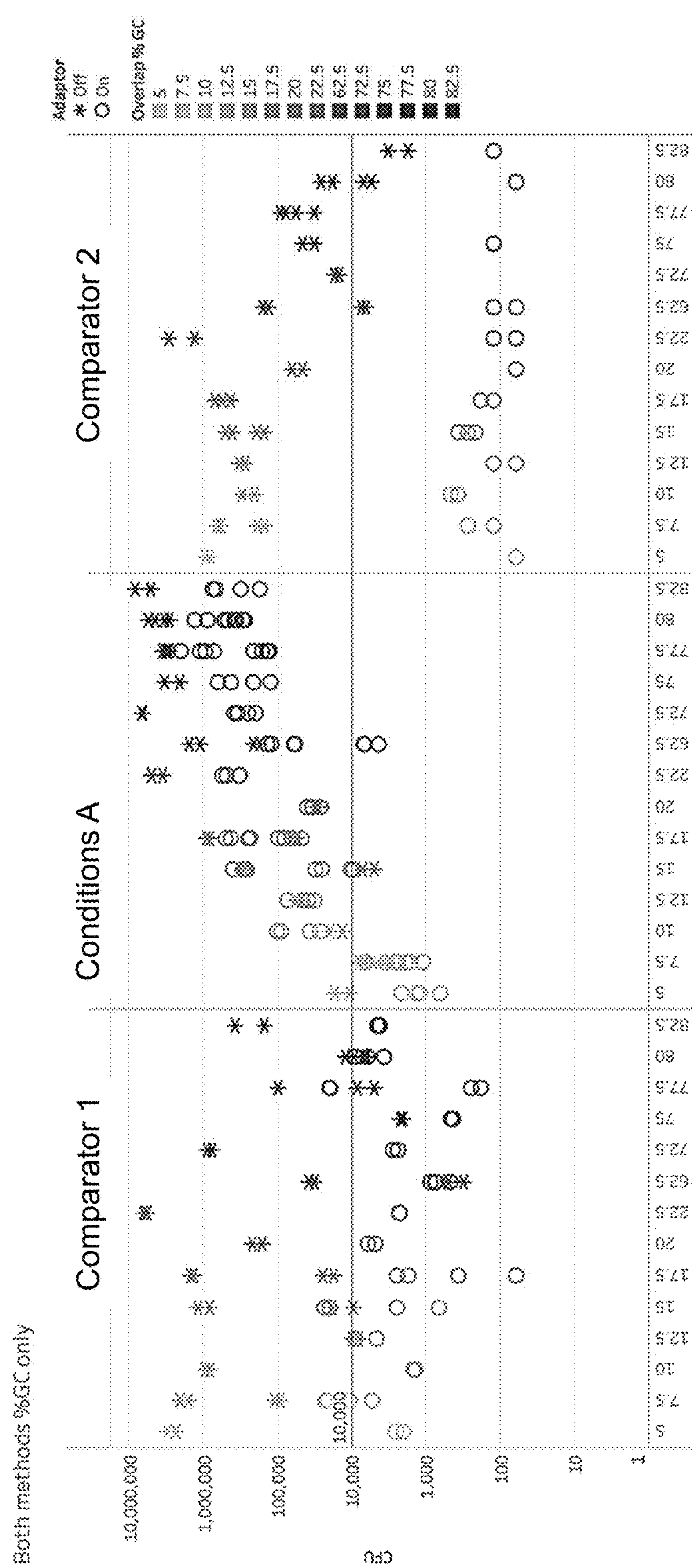
FIG. 12B is a graph of colony forming units (CFUs) of A/T rich overlap homology sequences.
Figure 12C:
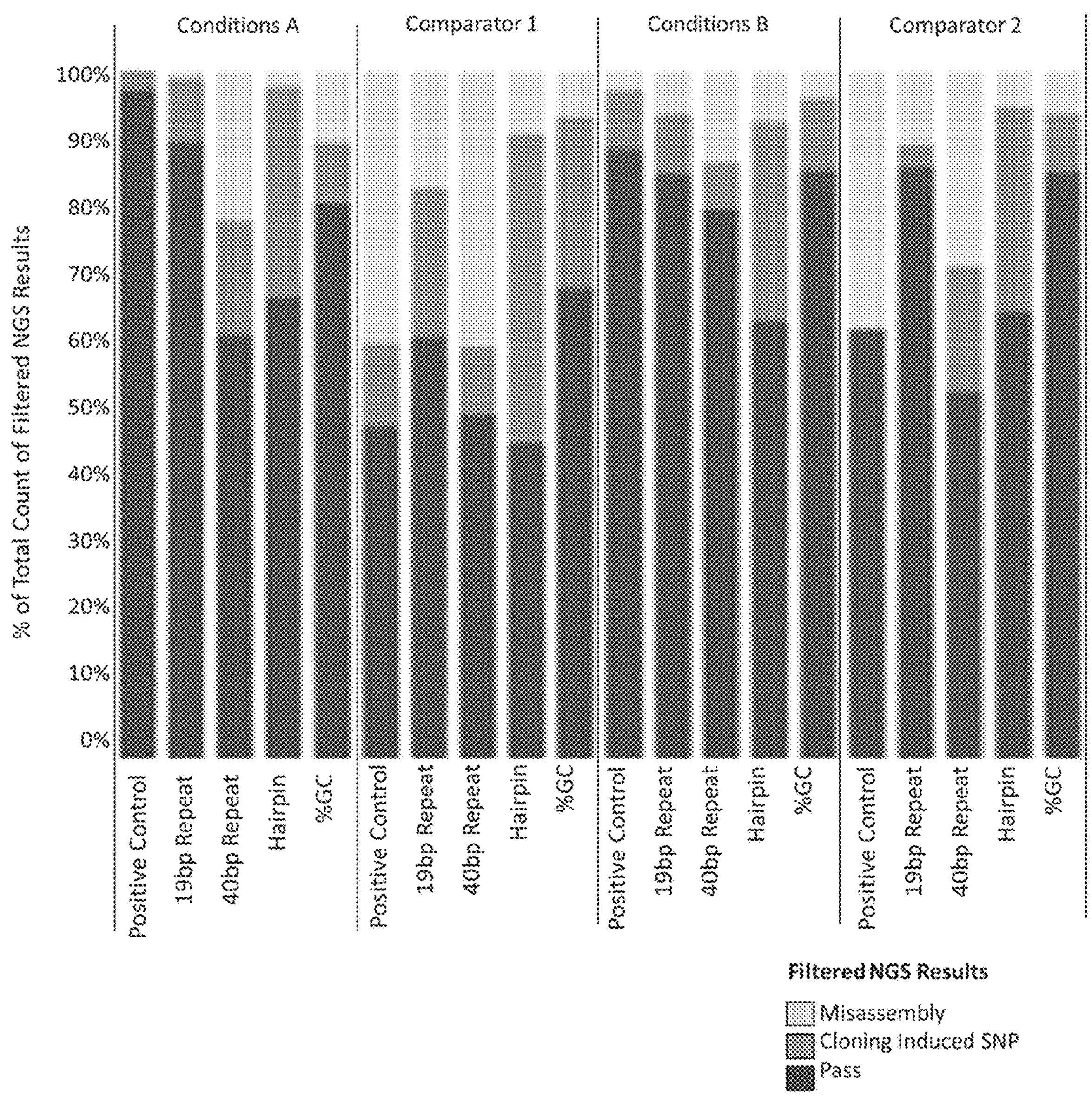
FIG. 12C is a graph of pass rates of Comparator 1 and Comparator 2.

Enzymatic mediated nucleic acid (guided assembly) using reaction conditions as described in Example 4 was performed ("Conditions A"). Enzymatic mediated nucleic acid assembly resulted in high colony forming units (CFUs) even in the presence of direct repeats flanking homology sequences and secondary structures (FIG. 12A). Furthermore, CFUs from the enzymatic mediated nucleic acid assembly were tightly distributed, demonstrating robust reaction conditions. A/T rich overlap homology sequences contained less than 10% GC as seen in FIG. 12B. As compared to Comparator 1 and Comparator 2 assembly (alternative exonuclease/ligase-based assembly methods), enzymatic mediated nucleic acid assembly was significantly more efficient with homology regions over 72.5% GC. Accuracy was also measured by NGS sequencing 8-12 clones. There was no significant impact to enzymatic mediated nucleic acid assembly accuracy with the extreme GC %, hairpins or direct repeats; average enzymatic mediated nucleic acid assembly pass rates ranged from 56% to 88% regardless of the presence or absence of universal adapter sequences. Comparator 1 and Comparator 2 assembly performed more poorly. Comparator 2 assembly reactions had pass rates ranging from 41% to 56% and Comparator 1 had pass rates ranging 53% to 75% (FIG. 12C).

Figure 12D:
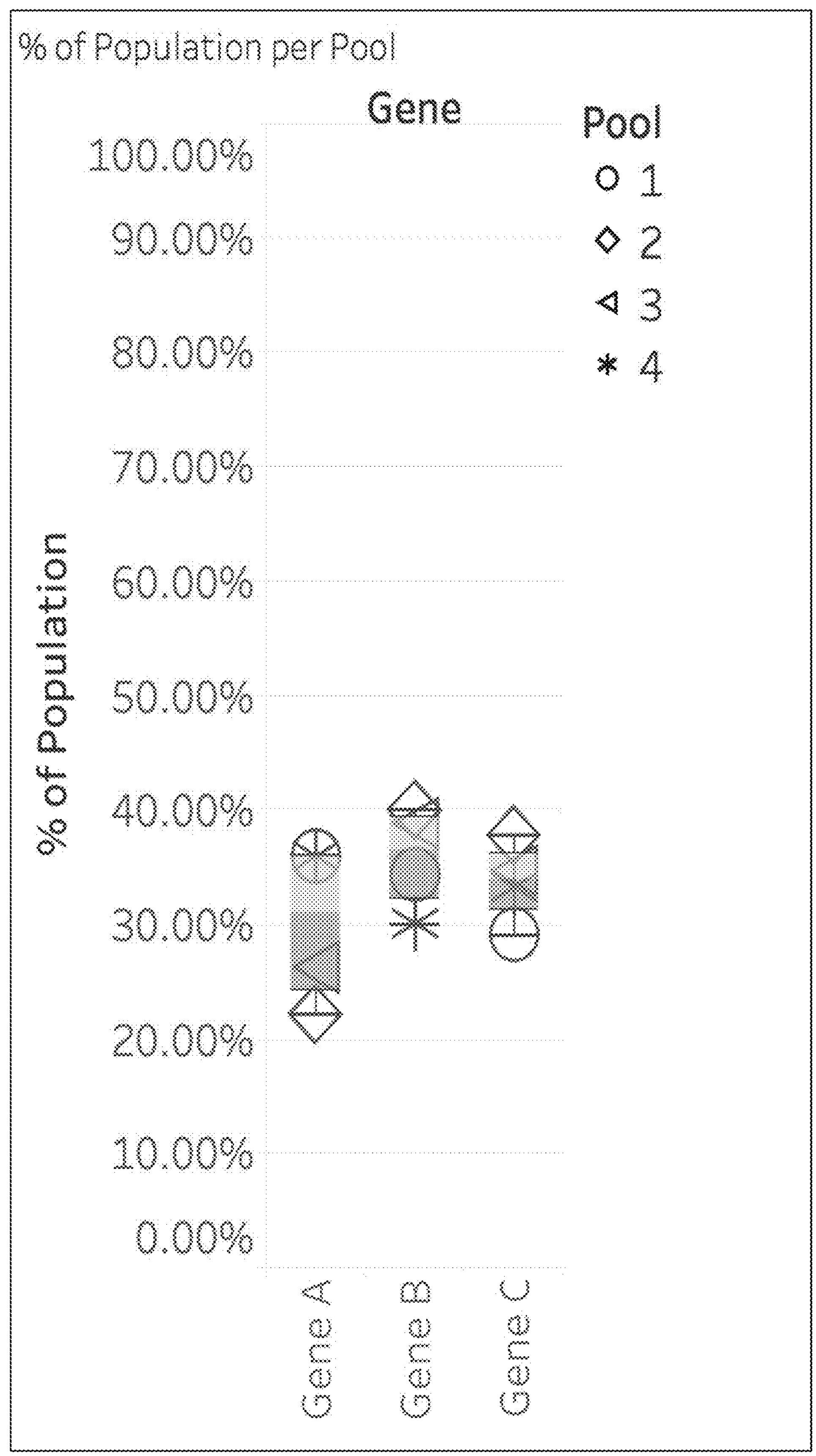
FIG. 12D is a graph of assembly specificity and sequence bias by an enzymatic assembly method by percent of the population comprising three assembled genes. Assembly of three different genes (Gene A, Gene B, Gene C), composed of 9 dsDNA input fragments with adapters were assembled in a single reaction.
Figure 12E:
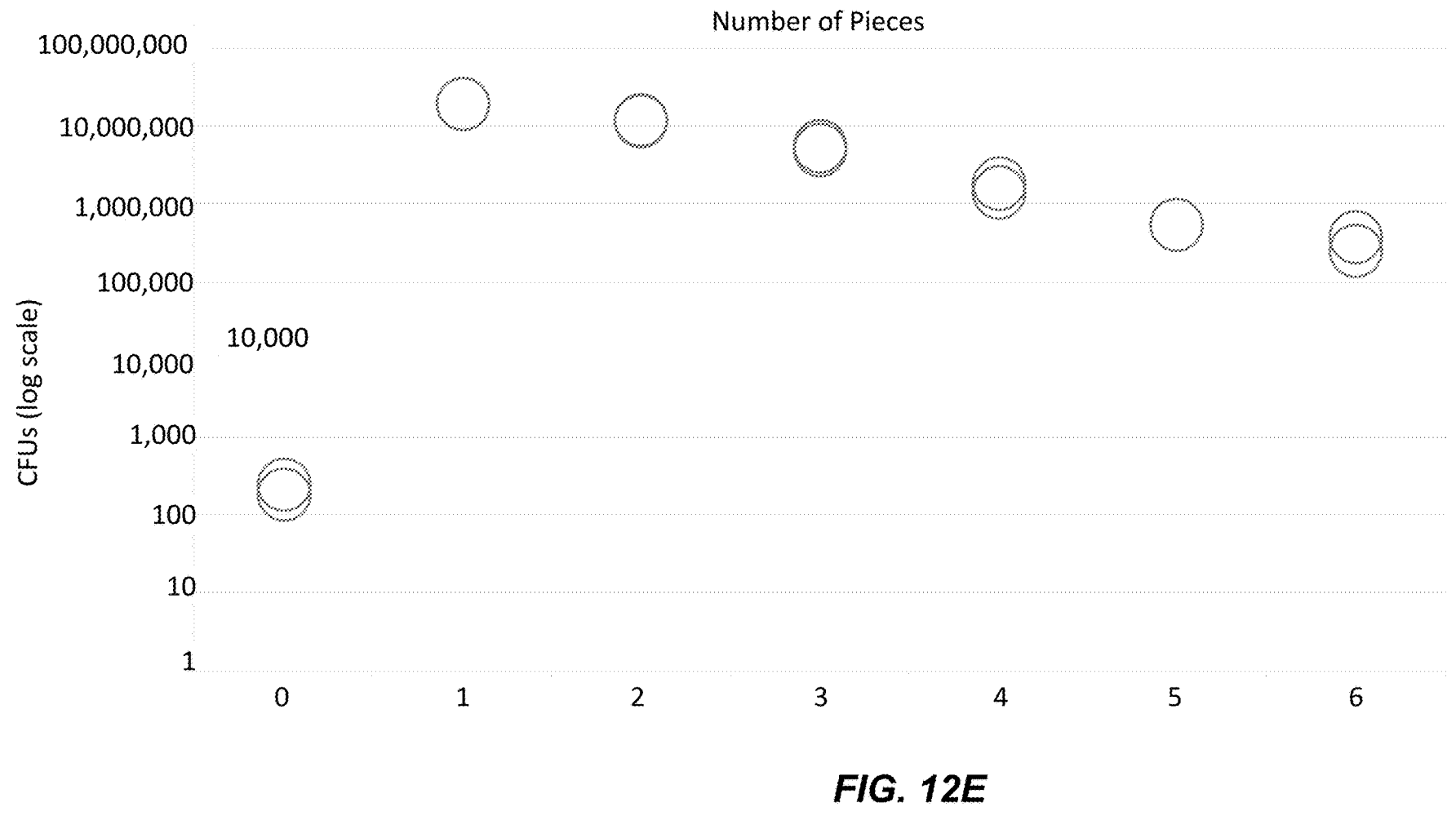
Figure 12F:
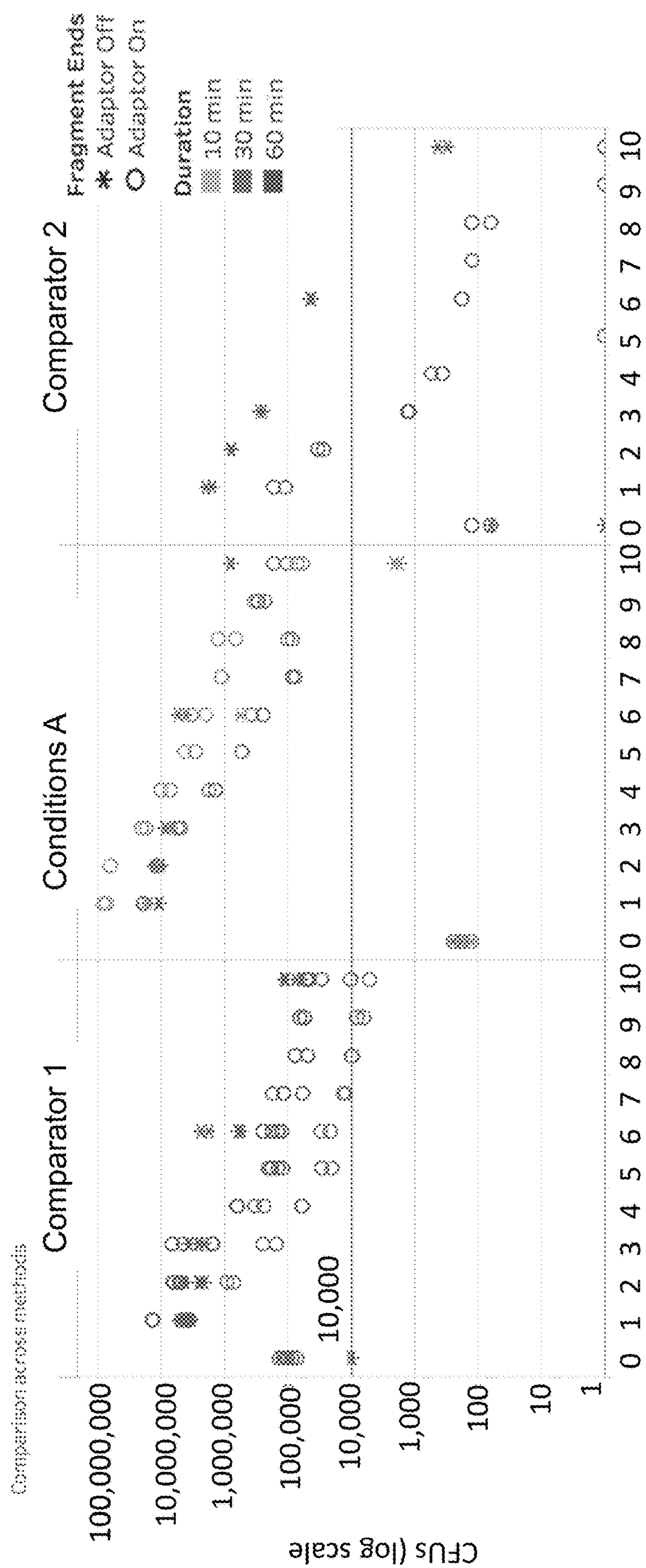
FIG. 12F is a graph of colony forming units (CFUs) for assembly of zero to ten DNA fragments at once using an enzymatic assembly method, Comparator 1, or Comparator 2.
Figure 12G:
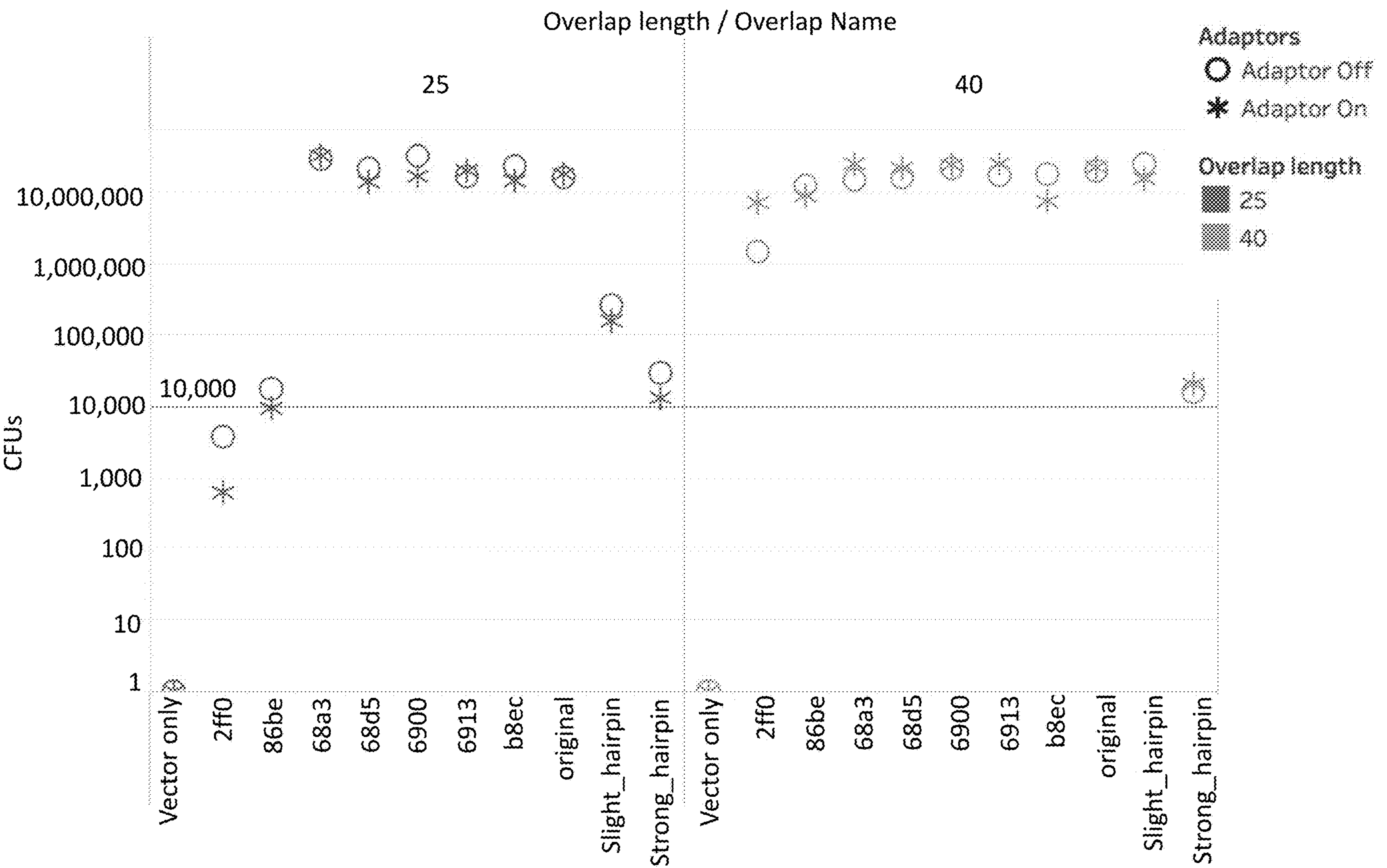
FIG. 12G is a graph of colony forming units (CFUs) for either 25 bp or 40 bp overlap homology regions using an enzymatic assembly method.

Assembly specificity and sequence bias were evaluated through multiplexed gene assembly (FIG. 12D). Assembly of three different genes (Gene A, Gene B, Gene C), composed of nine dsDNA input fragments with universal adapters were assembled in a single reaction. Homology sequence similarities ranged between 28-60%. In parallel independent reactions (N=4), the nine input fragments were subjected to enzymatic mediated nucleic acid assembly to form three genes. All constructs shared 5' and 3' primer sites, PCR amplified to enrich for the full length gene, cloned into a plasmid using the enzymatic mediated nucleic acid assembly and transformed into *E. coli*. Ninety six colonies from each reaction pool were isolated for Sanger sequenced and the final constructs sequenced. All sequencing reads indicated full length constructs for the desired genes and did not show evidence of universal adapter sequences, chimeric gene sequences, or misassemblies. As seen in FIG. 12D, a tight distribution of each gene sequence around the expected average of 33% was observed, again demonstrating accuracy and specificity of enzymatic mediated nucleic acid assembly without sequence bias. Larger fragments were also successfully assembled. Using the enzymatic assembly method, six DNA fragments were assembled at once using an enzymatic reaction, with a high number of colony forming units obtained (FIG. 12E). Conditions A resulted in a higher number of CFUs for assembly of larger fragments (up to 10) than comparator 1 or comparator 2 conditions as shown in FIG. 12F. Additional design elements such as optimal homology lengths between fragments was tested (FIG. 12G).

Example 6: 400 Base Pair Multiplex Gene Assembly

Figure 13A:
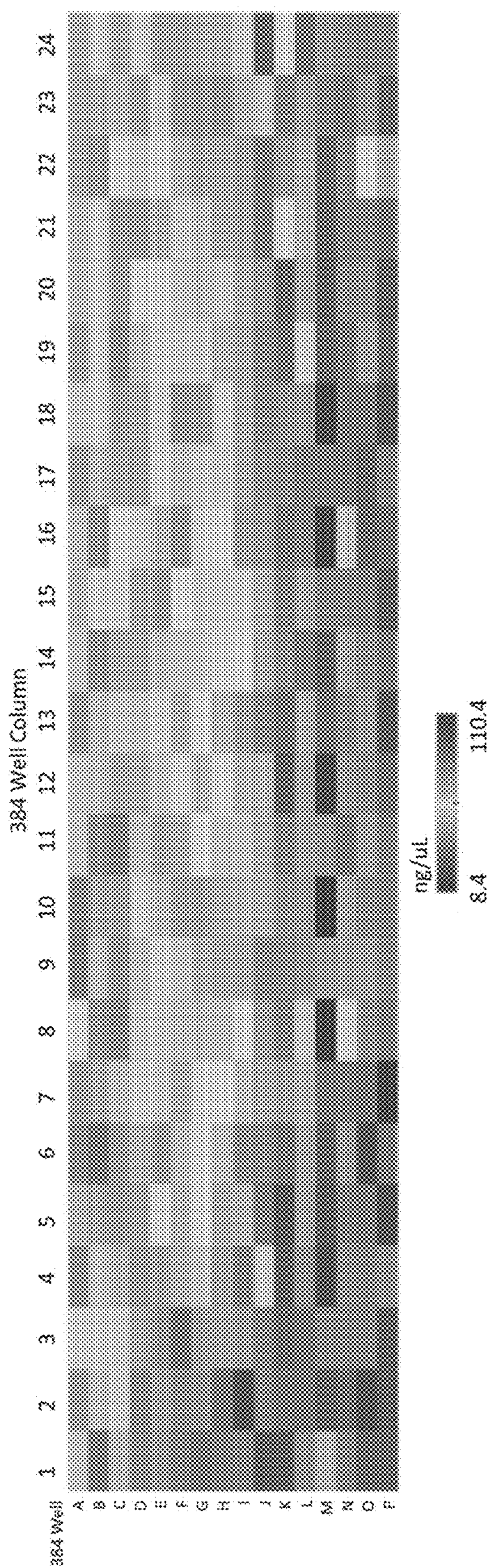
FIG. 13A shows relative concentrations of DNA following PCR using universal primers following multiplex assembly.
Figure 13B:
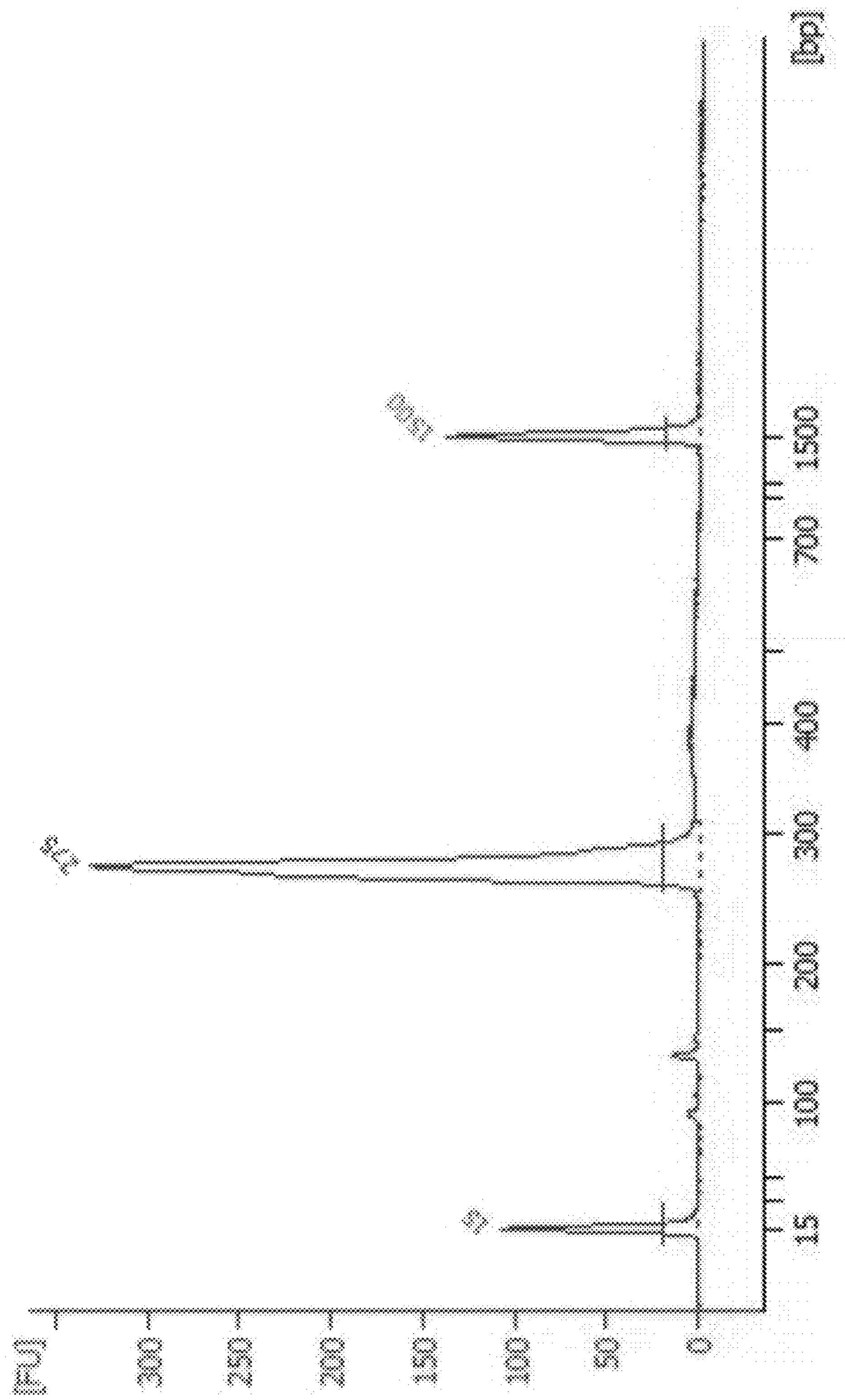
FIG. 13B shows a plot from a BioAnalyzer reading following multiplex assembly.
Figure 13C:
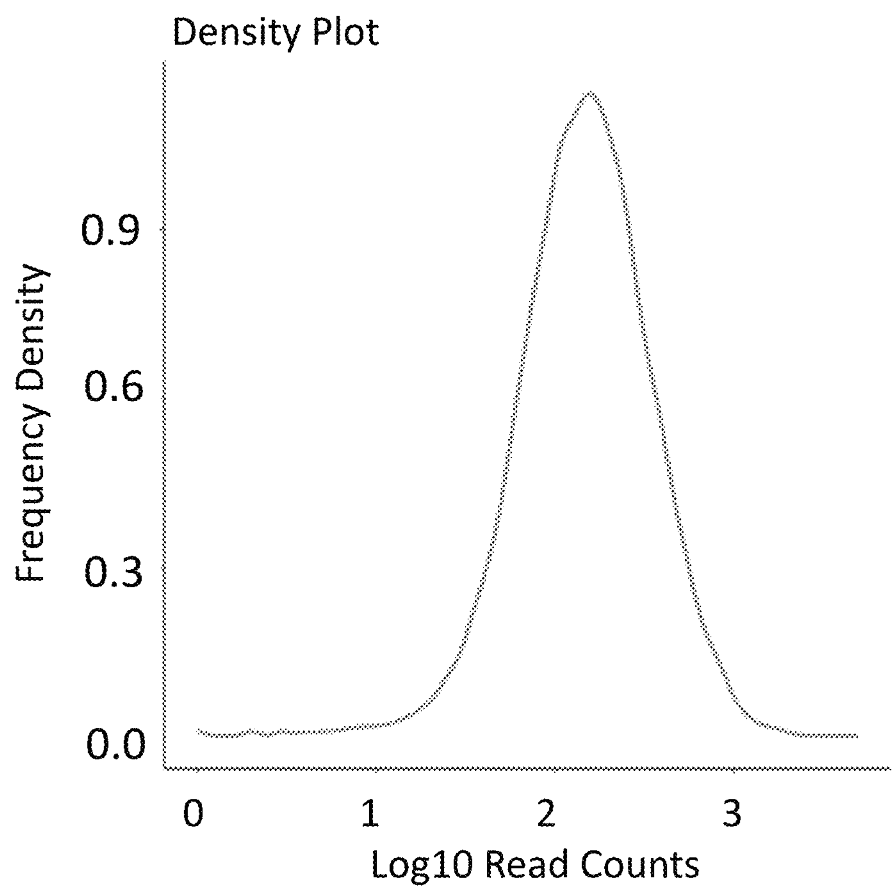
FIG. 13C shows a density plot using 140× coverage of populations of genes following multiplex assembly.
Figure 13D:
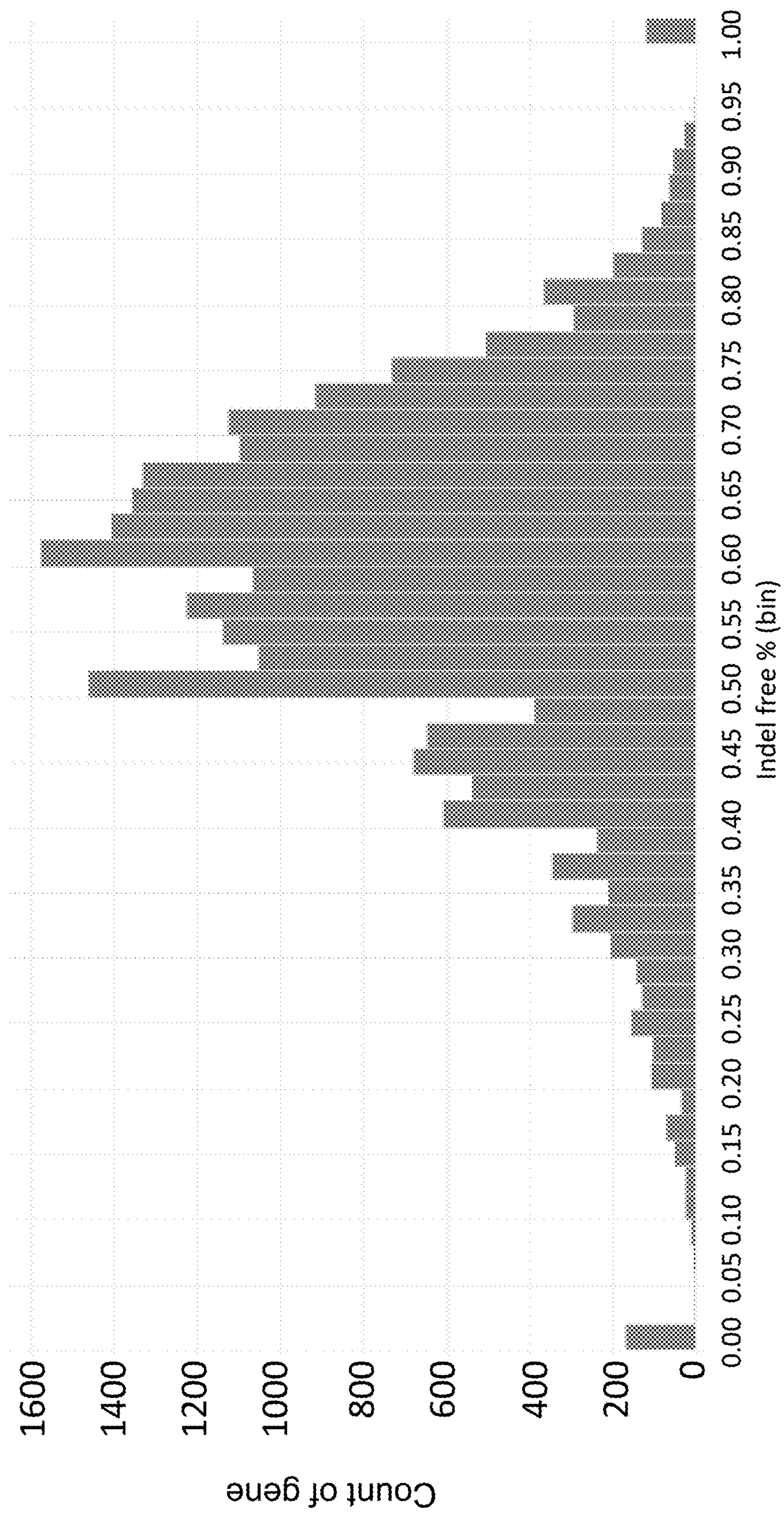
FIG. 13D shows percentage of insertion/deletion free in populations of genes following multiplex assembly of a 400 bp gene pool.
Figure 13E:
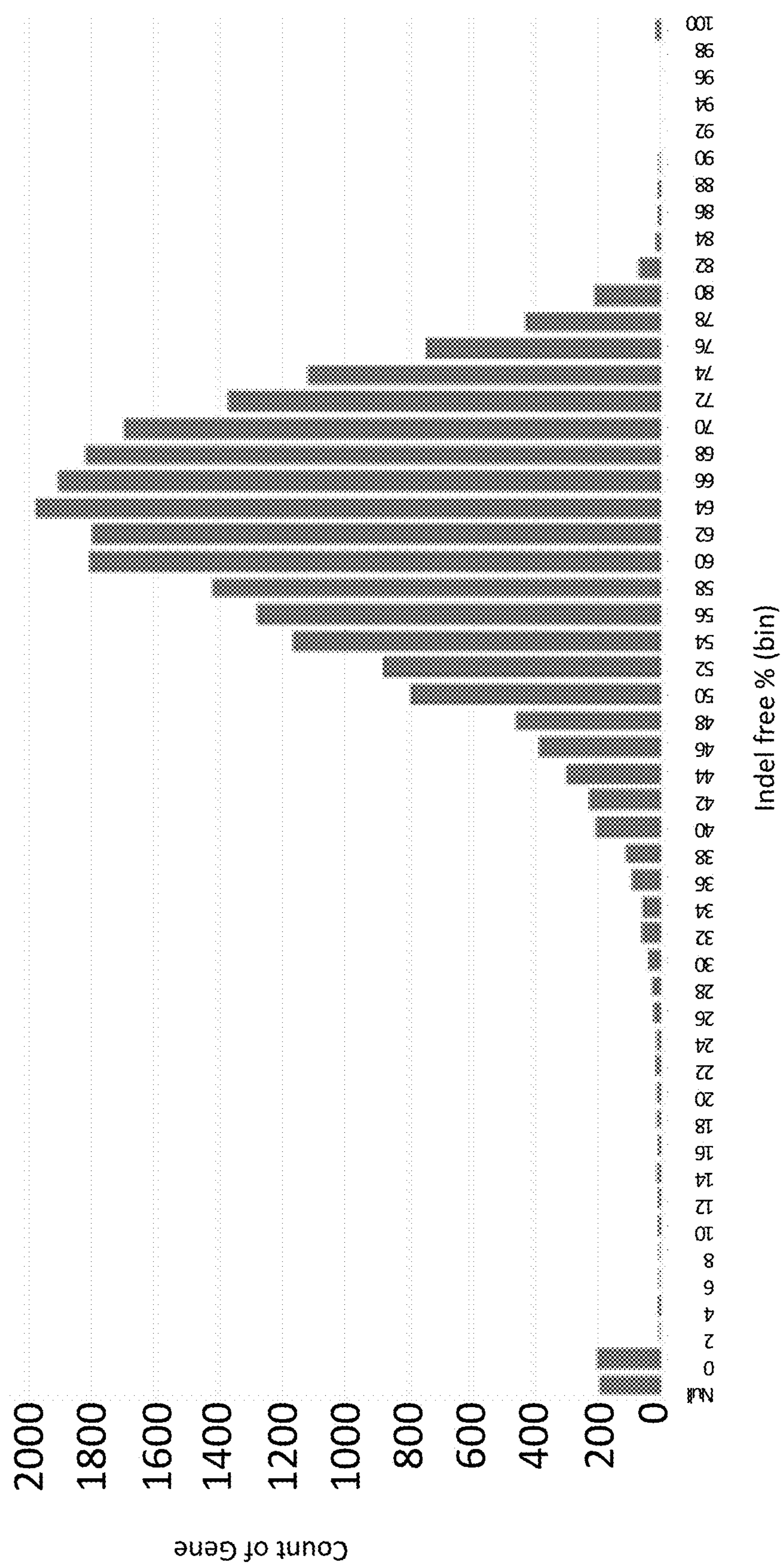
FIG. 13E shows percentage of insertion/deletion free in populations of genes following multiplex assembly.
Figure 13F:
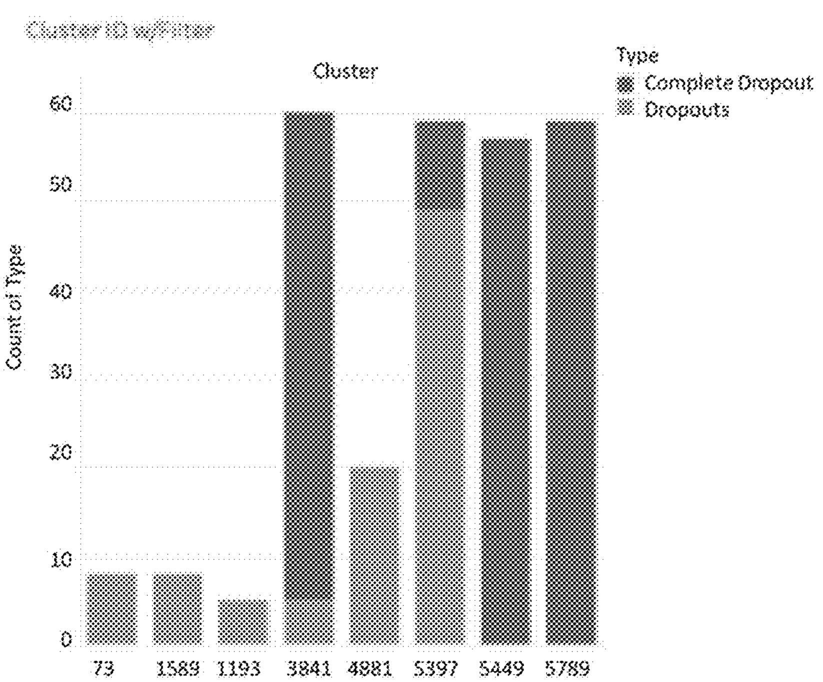
FIG. 13F shows percentage of complete dropout, dropout, and runaway in populations of genes following multiplex assembly.
Figure 13G:
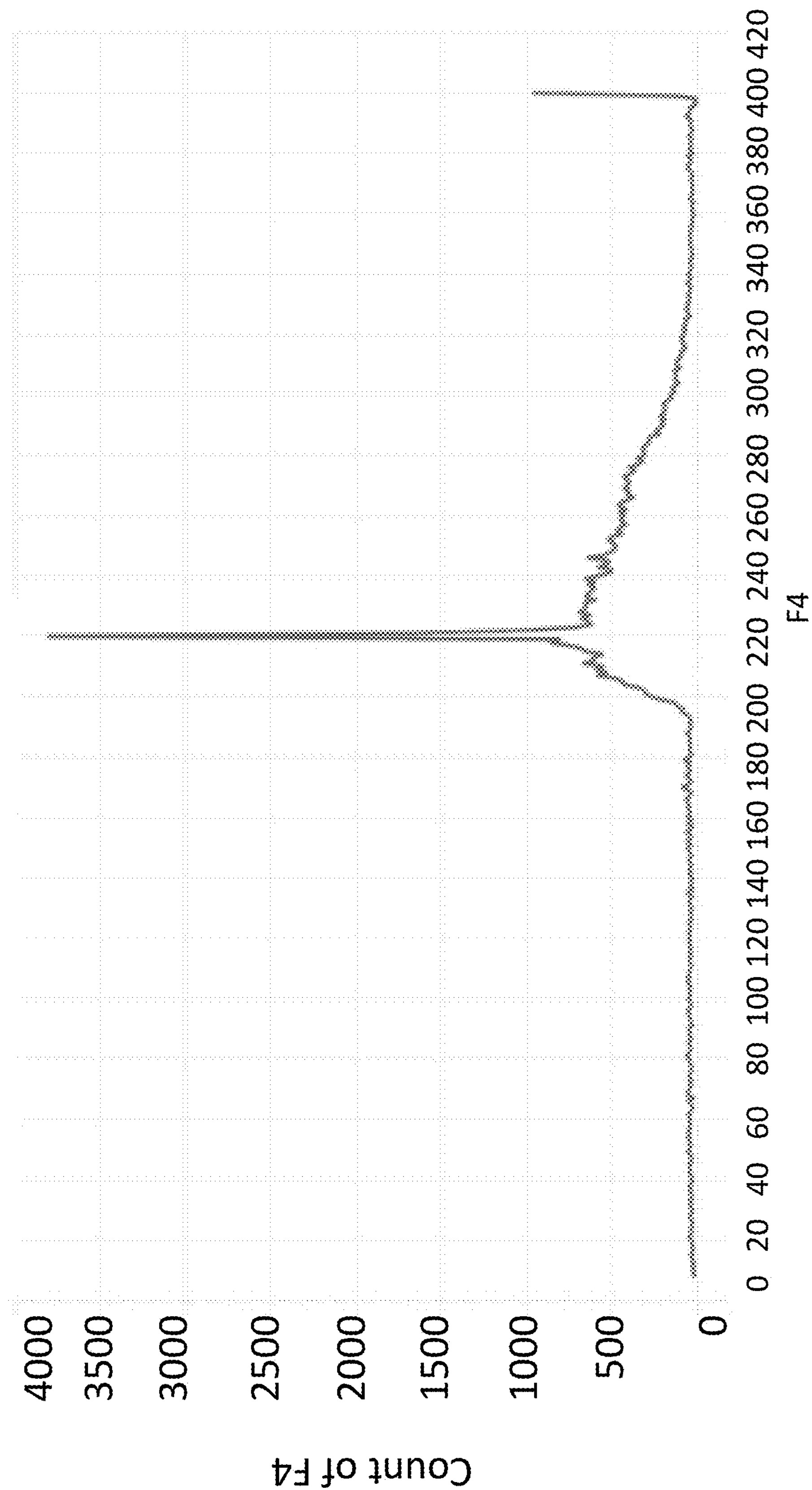
FIG. 13G shows a graph of soft clipping/chimeric reads in populations of genes following multiplex assembly.

Multiplexed assembly of 60 genes/cluster was performed using 270mer nucleic acids comprising Uni9 universal primers. Data from assembly of 23,000 genes is shown in FIGS. 13A-13G. FIG. 13A shows relative concentrations of DNA following PCR using universal primers. FIG. 13B shows a plot from a BioAnalyzer reading. FIGS. 13C-13E shows next generation sequencing (NGS) results, specifically a density plot using 140× coverage (FIG. 13C) and distribution of percentage of insertion/deletion free genes (FIGS. 13D-13E). FIG. 13F shows percentage of complete dropout, dropout, and runaway. FIG. 13G shows a graph of soft clipping/chimeric reads. About 1% of the population of nucleic acids comprises chimeric gene fragments. Results are also seen in Tables 15-16 below.

TABLE 15

| QC Metrics | | | | | |
|---|---|---|---|---|---|
| QC Metric | Complete Dropouts (missing sequence) | Dropouts (Outside 10-fold range) | Run-aways (Outside 10-fold range) | % Genes with at least 1 indel-Free Sequence | Average % Indel-Free Rate for a Gene in Pool |
| Population 1 | 1.09% | 1.12% | 0.23% | 98.32% | 62.3% |
| Population 2 | 0.3% | 1.38% | 0A% | 98.12% | 54.12% |
| Population 3 | 0.29% | 1.38% | 0A% | 98.09% | 52.56% |
| Population 4 | 0.19% | 1.3% | 0.44% | 98.44% | 51.94% |
| Population 5 | 0.2% | 1.68% | 0.3% | 98.5% | 59% |
| Population 6 | 0.18% | 1.05% | 0.33% | 98.73% | 52.47% |
| Population 7 | 0.2% | 1.78% | 0.26% | 98.5% | 60% |
| Population 8 | | | | | |
| Population 9 | | | | | |
| Population 10 | 0.2% | 1.38% | 0.23% | 98.64% | 60.5% |
| Population 11 | 0.27% | 1.55% | 0.20% | 98.57% | 58.8% |

TABLE 16

| QC Metrics Percentile | | |
|---|---|---|
| Uniformity Table | $90^{th}/10^{th}$ Percentile | $95^{th}/5^{th}$ Percentile |
| Population 1 | 9.08 | 18.12 |
| Population 2 | 11.8 | 23.3 |
| Population 3 | 10.7 | 23.6 |
| Population 4 | 10.8 | 23.1 |
| Population 5 | 11.9 | 27.17 |
| Population 6 | 9.6 | 19.8 |
| Population 7 | 10.89 | 22.17 |
| Population 8 | | |
| Population 9 | | |
| Population 10 | 10.64 | 22.71 |
| Population 11 | 11.69 | 23 |

Example 7: Combinatorial Assembly of Variants

Figure 14A:
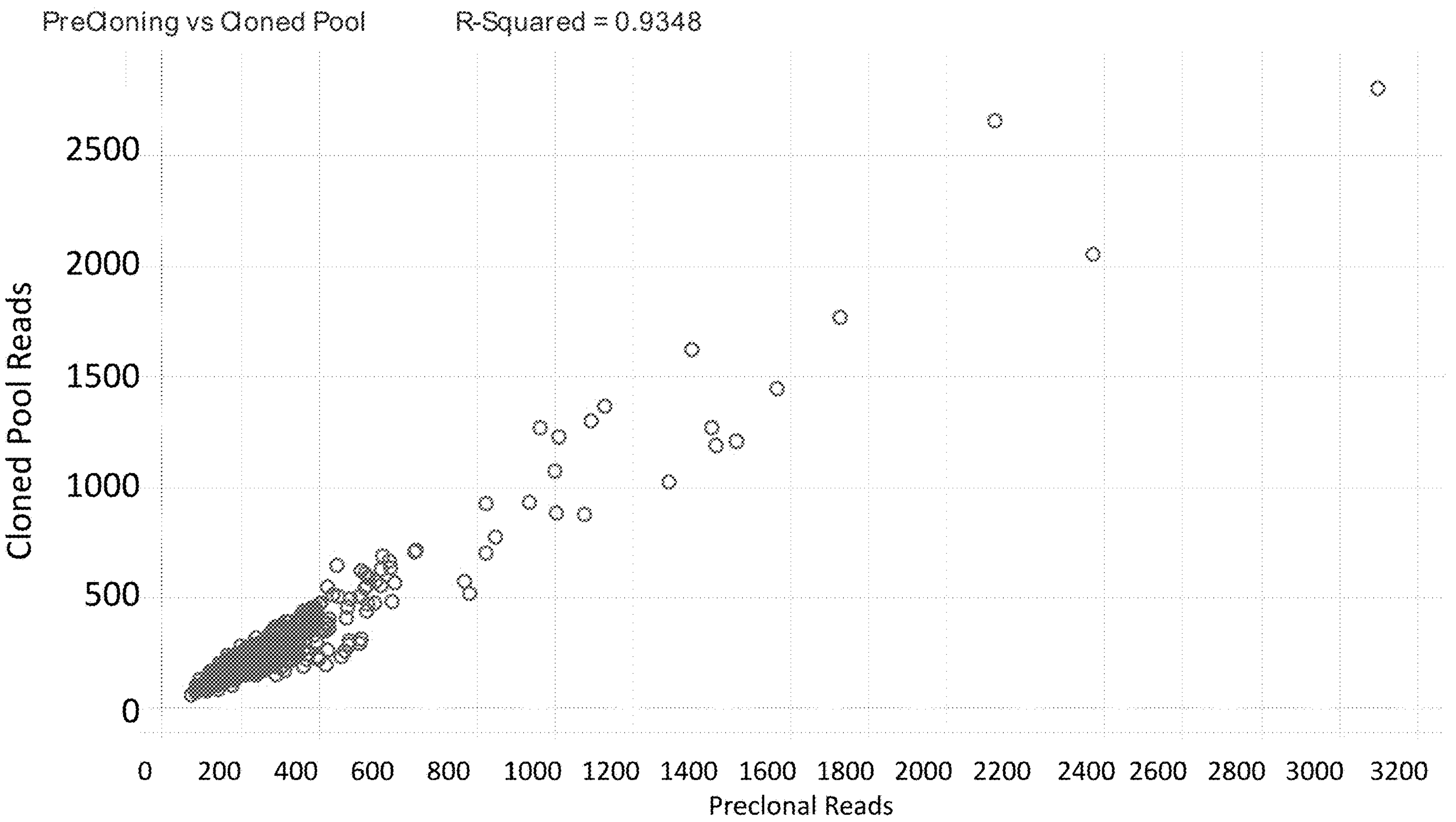
FIG. 14A is a graph of uniformity of full length sequences before and after cloning of combinatorial assembly using four populations of gene fragments.
Figure 14B:
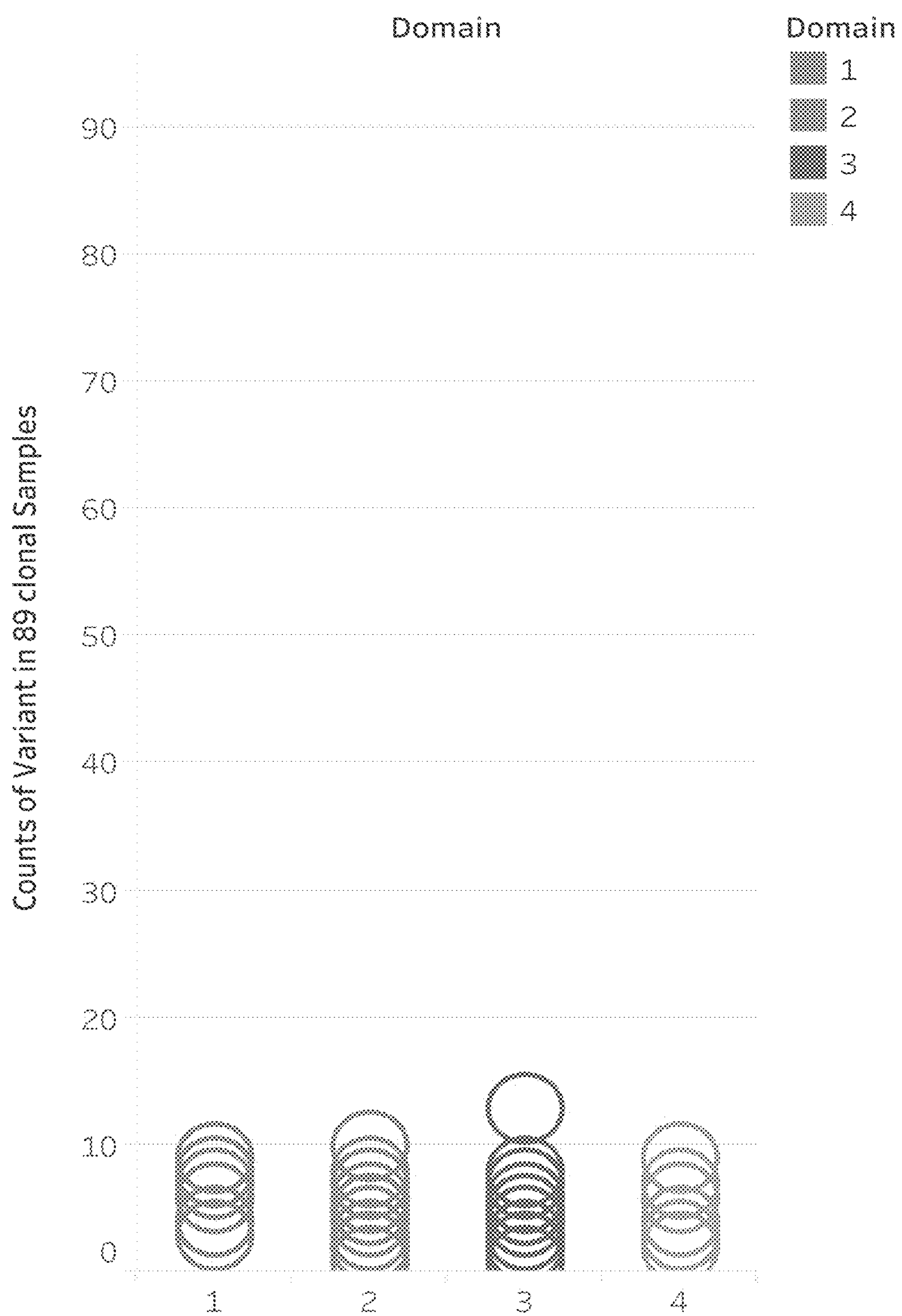
FIG. 14B is a graph of frequency of variants within a domain following combinatorial assembly using four populations of gene fragments.

Combinatorial assembly of variants was performed using methods as described herein. Four input populations were assembled. Assembly resulted in about 150,000 variants and uniformity of full length sequences before and after cloning (FIG. 14A) as well as uniform variant frequency (FIG. 14B). After assembly, products were PCR amplified to enrich for the full length gene then cloned into a plasmid and transformed into *E. coli.* 96 colonies from each reaction pool were isolated for Sanger sequencing. All sequencing reads indicated full length constructs for the desired genes. There was no observation of internal universal adapter sequences, chimeric gene sequences, or misassemblies.

Example 8: Scalable Assembly Using Enzymatic Mediated Nucleic Acid Assembly

Enzymatic mediated nucleic acid assembly was performed using the Labcyte Echo® 525 Liquid Handler, to generate actionable DNA constructs on a large scale. In a single pot reaction, miniaturized enzymatic mediated nucleic acid assembly reactions were used to assemble two linear dsDNA fragments into a vector enabling fluorescent protein expression under a wild-type and variant p70 promoter. p70 promoter tuning was assessed by driving expression of the fluorescent protein mCherry under a wild-type (WT) promoter and test synthesized p70 variants differentially driving GFP expression in the same construct. By normalizing the GFP to mCherry signal, the various mutated p70 promoter strengths were approximated. As a result of multiplexing DNA assembly and myTXTL® protein synthesis, optimal protein production conditions were ascertained within the miniaturized reactions.

Example 9: Immunoglobulin Sequence Assembly

This example illustrates a de novo synthesis method for immunoglobulin sequence assembly.

A first leader sequence, a first variable region, and a first CDR segment are synthesized and then subject to polymerase chain assembly (PCA) to generate a first plurality of gene fragments. A second leader sequence, a second variable region, and a second CDR segment are synthesized and then subject to assembly PCR or PCA to generate a second plurality of gene fragments. A third plurality of gene fragments comprising a second constant region followed by a self-cleaving peptide and a fourth plurality of gene fragments comprising a variable constant segment are synthesized. The third plurality of gene fragments and the fourth plurality of gene fragments are added to the first plurality of gene fragments and the second plurality of gene fragments followed by PCR. An error correction reaction may optionally be performed. The resulting construct is pooled, cloned, and subject to next generation sequencing.

Example 10: Multiplex Immunoglobulin Sequence Assembly

This example illustrates a de novo synthesis method for multiplex immunoglobulin sequence assembly.

Gene fragments are synthesized comprising variants of a first variable region and amplified with gene fragments comprising a 40 base pair (bp) region complementary to the first variable region and a first CDR and J segment to generate a first plurality of gene fragments. Gene fragments are synthesized comprising variants of a second variable region and amplified with gene fragments comprising a second CDR and J segment to generate a second plurality of gene fragments. A third plurality of gene fragments is synthesized comprising a constant region, a self-cleaving peptide sequence, a first leader sequence, and a 40 base pair (bp) region complementary to the second variable region and a second CDR and J segment. The self-cleaving peptide sequence is P2A.

The first plurality of gene fragments, the second plurality of gene fragments, and the third plurality of gene fragments are assembled using an enzymatic based assembly method, PCR purified, and pooled. All non-assembled fragments are purified away. The final construct is then cloned into a vector.

Example 11: Paired Variant Assembly Using Type IIS Exposed Barcode

This example illustrates a paired variant assembly method using a Type IIS exposed barcode.

A first plurality of gene fragments is synthesized comprising a barcode followed by a first restriction endonuclease site, a second restriction endonuclease site, and a first complementary determining region (CDR) segment and J segment. The CDR segment and J segment is about 100 base pairs. The first restriction endonuclease site or the second restriction endonuclease site is a Type IIS restriction endonuclease (TIIS-RE) site. A second plurality of gene fragments is synthesized comprising a first constant region followed by a self-cleaving peptide sequence, a first leader sequence, and a first variable region. The self-cleaving peptide sequence is P2A. A number of first variable regions synthesized is about 100.

The first plurality of gene fragments and the second plurality of gene fragments are combined and PCR amplified to generate a third plurality of gene fragments. The third plurality of gene fragments comprises the barcode followed by the first restriction endonuclease site, the first constant region, the cleaving peptide sequence, the first leader sequence, the first variable region, and the first CDR and J segment. The third plurality of gene fragments is combined with a fourth plurality of gene fragments comprising a vector sequence followed by a second leader sequence, a second variable region, a second CDR segment and J segment, the first TIIS-RE site, and a barcode to generate a fifth plurality of gene fragments. A number of second variable regions synthesized is about 130.

The fifth plurality of gene fragments comprises the vector sequence followed by the second leader sequence, the second variable region, the second CDR and J segment, the first TIIS-RE site, the barcode, the first TIIS-RE site, the first constant region, the cleaving peptide sequence, the first leader sequence, the first variable region, and the first CDR segment. The fifty plurality of gene fragments is PCR amplified and cloned followed by treatment with a TIIS restriction endonucleases to cut at the TIIS-RE sites to remove the barcode to generate a sixth plurality of gene fragments comprising the vector sequence followed by the second leader sequence, the second variable region, the second CDR segment, the first constant region, the cleaving peptide sequence, the first leader sequence, the first variable region, and the first CDR and J segment. The sixth plurality of gene fragments is then cloned into a vector to generate a final construct comprising the second leader sequence, the second variable region, the second CDR segment, the first constant region, the cleaving peptide sequence, the first leader sequence, the first variable region, the first CDR and J segment, and a variable constant region. A number of gene fragments synthesized is about 1000.

Example 12: Paired Variant Assembly Using Paired Homology

This example illustrates assembly of paired variants comprising paired homology.

103 variant gene fragments comprising a first variable region are synthesized. The 103 variant gene fragments are amplified with a first CDR3 and J segment to generate a first plurality of gene fragments. A different set of 131 variant gene fragments comprising a second variable region are synthesized. The 131 variant gene fragments are amplified with a second CDR3 and J segment to generate a second plurality of gene fragments. A third plurality of 130 variant gene fragments comprising a sequence homologous to the first CDR3 and J segment followed by a constant region, a self-cleaving peptide sequence, a first leader sequence, and a 40 base pair (bp) region complementary to the second variable region is synthesized.

The first plurality of gene fragments, the second plurality of gene fragments, and the third plurality of gene fragments are assembled and cloned into a destination vector. The final construct comprises a second leader sequence followed by the second variable region, the second CDR and J segment, the second constant region, the self-cleaving peptide sequence, the first leader sequence, the first variable region, the first CDR and J segment, and the variable constant region.

Example 13: Paired Variant Assembly Using Type IIS Sites

This example shows a paired variant assembly method of gene fragments comprising Type IIS sites.

A first plurality of gene fragments comprising a first leader sequence and a first variable region is synthesized. A second plurality of gene fragments comprising a second variable region is synthesized. A third plurality of gene fragments comprising a first Type IIS site followed by a 40 base pair (bp) region complementary to the second variable region. A fourth plurality of gene fragments comprising the 40 base pair (bp) region complementary to the second variable region followed by the second CDR3 and J segment and a variable constant segment is synthesized. A fifth plurality of gene fragments comprising a segment homologous to the first variable region followed by the first CDR3 and J segment and the TIIS site is synthesized.

The first plurality of gene fragments, the second plurality of gene fragments, the third plurality of gene fragments, the fourth plurality of gene fragments, and the fifth plurality of gene fragments are pooled and PCR amplified in order to add the first CDR3 and J segment and the second CDR3 and J segment. The resulting gene fragment comprises the second variable region followed by the second CDR3 and J segment, the TIIS site, the first variable region, and the first CDR3 and J segment. The resulting gene fragment is subject to flap endonuclease mediated nucleic acid assembly and insertion into a destination vector. The destination vector comprises the second leader sequence and the variable constant region. Following insertion into a destination vector, the gene fragment comprises the second leader sequence followed by the second variable region, the second CDR3 and J segment, the first restriction endonuclease site, the first variable region, the first CDR3 and J segment, and the variable constant region. The gene fragment is then subject to Golden Gate Assembly to insert the second constant region to generate final construct. The final construct comprises the second leader sequence followed by the second variable region, the second CDR3 and J segment, the second constant region, the self-cleaving peptide sequence, the first leader sequence, the first variable region, the first CDR3 and J segment, and the variable constant region. A number of final constructs generated is about 10000.

Example 14: Polynucleotide Populations Specific for Each Variant

This example illustrates use of polynucleotide populations specific for each variable region. A first plurality of gene fragments is synthesized comprising a self-cleaving peptide sequence, a first leader sequence, and a first variable region. A gene fragment is synthesized comprising a segment homologous to a second variable region followed by a second CDR3 and J segment, a Type IIS site, a first CDR3 and J segment, and universal primer. The gene fragment is combined and PCR amplified with a population of gene fragments comprising a leader sequence followed by the second variable region to generate a second plurality of gene fragments comprising the second leader sequence followed by the second variable region, the second CDR3 and J segment, the Type IIS site, the first CDR3 and J segment, and the universal primer. The second plurality of gene fragments is then assembled into a destination vector comprising the second leader sequence and a variable constant region to generate a third plurality of gene fragments. The third plurality of gene fragments comprises the second leader sequence followed by the second variable region, the second CDR3 and J segment, the Type IIS site, the first CDR3 and J segment, and the variable constant region.

The first plurality of gene fragments and the third plurality of gene fragments are assembled to insert the second constant region to generate a final construct. The final construct comprises the second leader sequence followed by the second variable region, the second CDR3 and J segment, the second constant region, the self-cleaving peptide sequence, the first leader sequence, the first variable region, the first CDR3 and J segment, and the variable constant region. A number of final constructs generated is about 10000.

Example 15: Paired Barcodes Using Dial Out PCR

This example illustrates use of paired barcodes and dial out PCR for nucleic acid assembly. A first plurality of gene fragments is synthesized comprising a first variable region. A second plurality of gene fragments is synthesized comprising a first hypervariable region followed by a 40 base pair (bp) region complementary to the first variable region, a first CDR3 and J segment, and a barcode. A third plurality of gene fragments is synthesized comprising a second leader sequence and a second variable region. A fourth plurality of gene fragments is synthesized comprising a second CDR3 and J segment. The first plurality of gene fragments and the second plurality of gene fragments are combined to create a first combinatorial library using PCR. The third plurality of gene fragments and the fourth plurality of gene fragments are combined to create a second combinatorial library using PCR.

The first combinatorial library and the second combinatorial library are assembled using flap endonuclease mediated nucleic acid assembly to generate a fifth plurality of gene fragments comprising the second leader sequence followed by the second variable region, the second CDR3 and J segment, the second constant region, the self-cleaving peptide sequence, the first leader sequence, the first variable region, the first CDR3 and J segment, the 40 base pair (bp) region complementary to a first variable region, and the barcode. The fifth plurality of gene fragments is circularized and sequenced with primers to generate a sixth plurality of gene fragments. Samples are identified by the barcode. The sixth plurality of gene fragments is then subject to dial out PCR and flap endonuclease mediated nucleic acid assembly into a vector to generate the final construct.

Example 16: Combinatorial Assembly of Variants

Combinatorial assembly of variants was performed using methods as described herein. Four input populations (or domains) ranging from 1.2-2.2 kb in length, with 15-20 variants each were assembled (number of variants in parentheses):

5'Vector-Domain1(15)-Domain2(20)-Domain3(20)-Domain4(20)-3'Vector

Figure 15A:
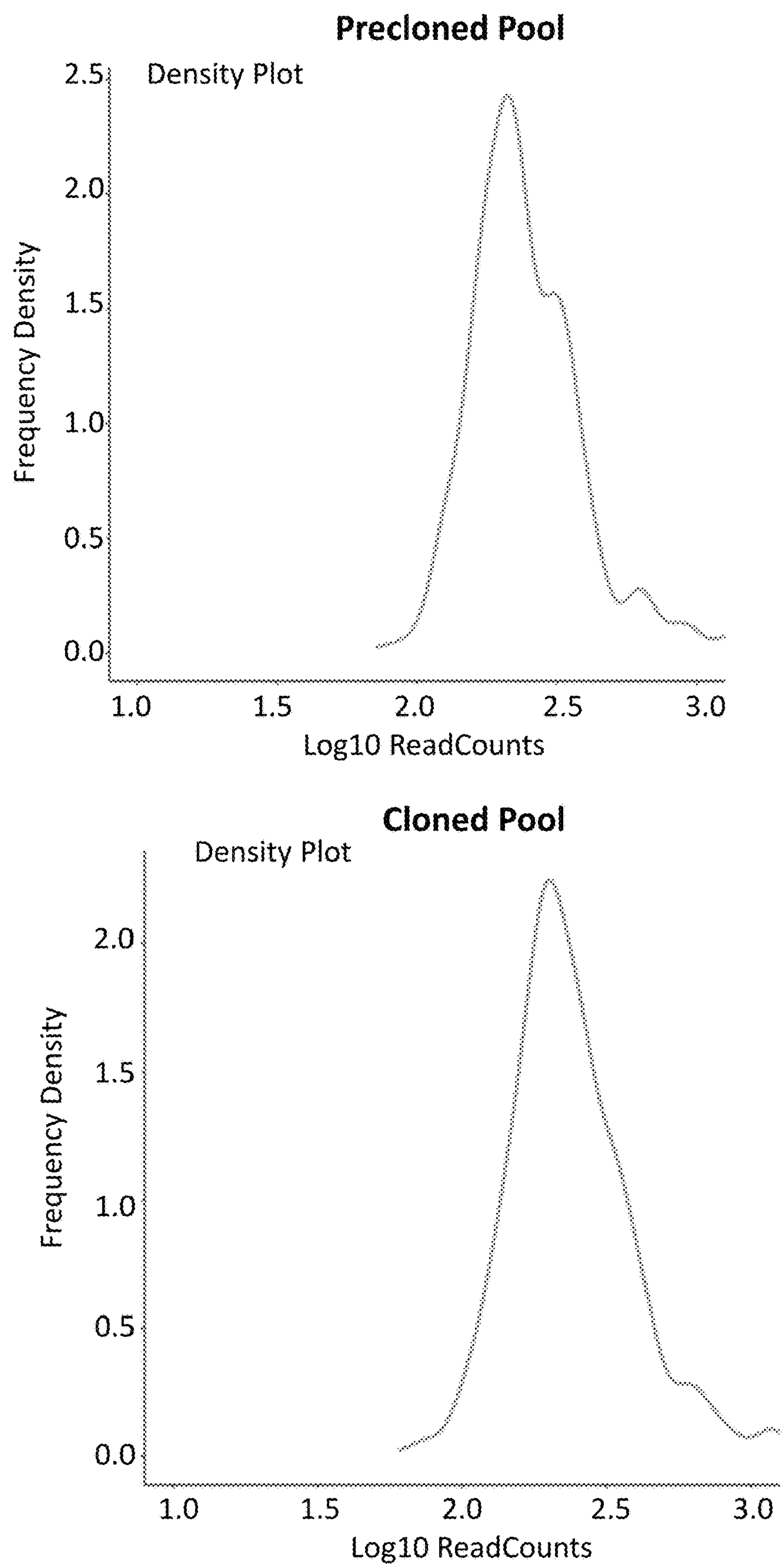
FIG. 15A are graphs of frequency density vs. log(read counts) for a pre-cloned pool (left) and cloned pool (right).
Figure 15B:
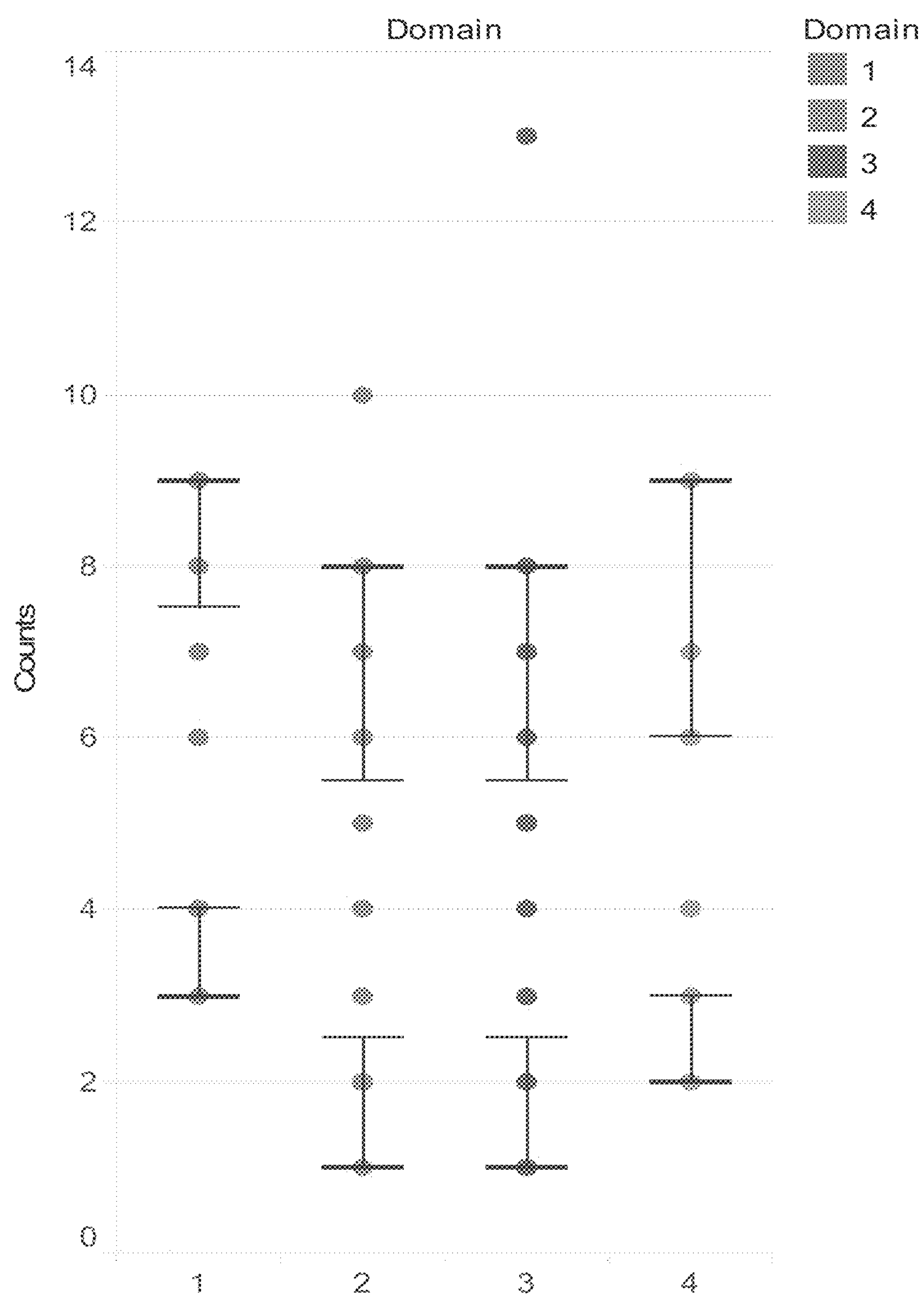
FIG. 15B is a graph of frequency of variants within a domain following combinatorial assembly using four populations of gene fragments.

Assembly resulted in about 120000 variants and uniformity of full length sequences before and after cloning into a bacterial expression vector (FIG. 15A, Table 17) as well as uniform variant frequency (FIG. 15B).

TABLE 17

| Percentile Metrics | $90^{th}/10^{th}$ Percentile | $95^{th}/5^{th}$ Percentile |
|---|---|---|
| Pre-Clonal Pool | 2.89 | 4.46 |
| Clonal Pool | 3.13 | 5.06 |

NGS results showed that a uniform distribution of all possible combinations of variants was obtained. This indicated the pool was unbiased with 95% of the possible variant combinations within 5× of each other. 89 individual clones were sequenced to see the different combinations present. All variants were represented in the picked colonies, and additionally all 89 pathways had a unique combination of variants (FIG. 15B).

Example 17: Combinatorial Assembly of Variants

Combinatorial assembly of variants was performed using methods as described herein. Two input populations (or domains) approximately 1.5 kb in length, with up to 100 variants each were assembled (for number of variants X):

5'Vector-Domain1(X)-Constant Domain-Domain3(X)-3'Vector

Figure 15C:
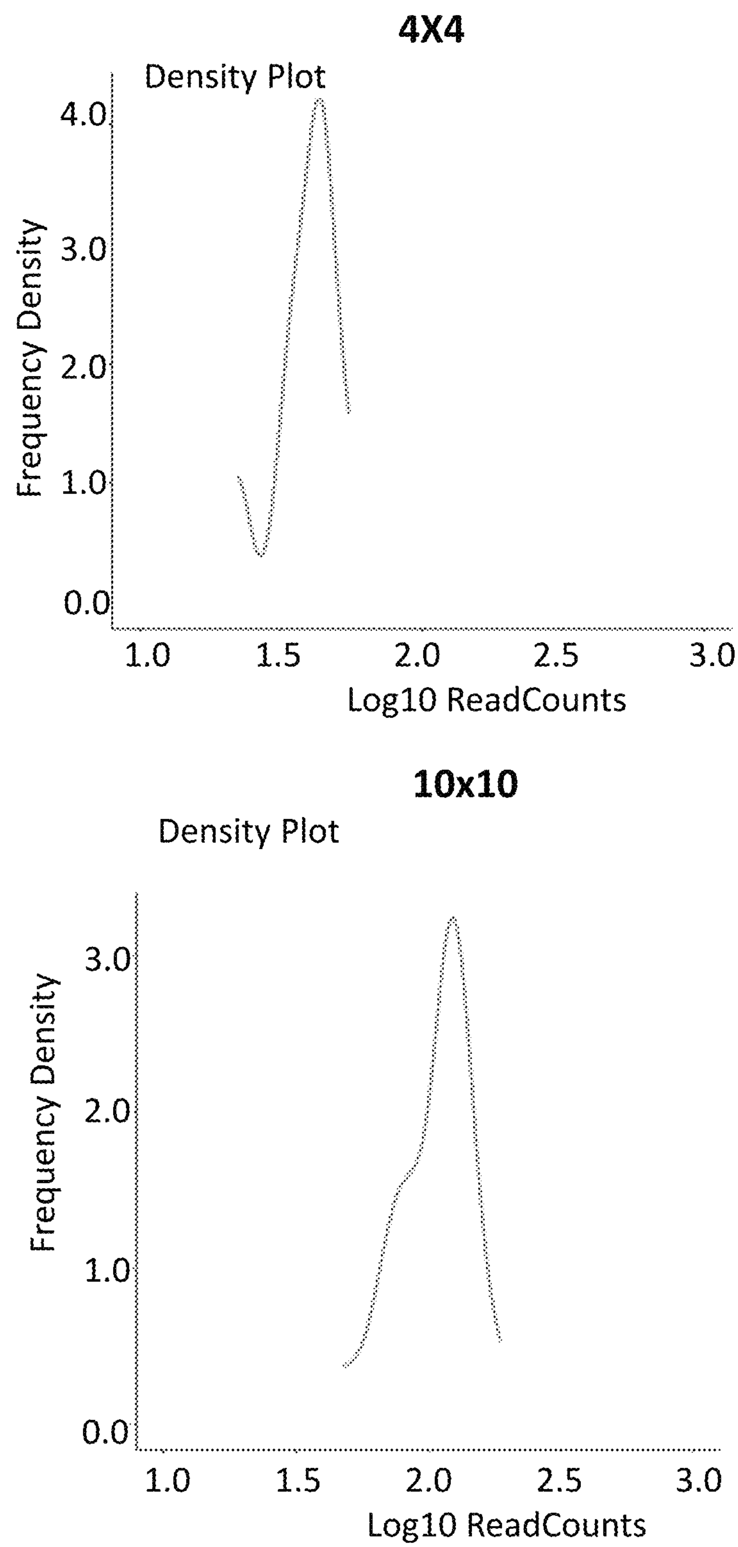
FIG. 15C are graphs of frequency density vs. log(read counts) for a 4×4 assembly (left) and 10×10 assembly (right).
Figure 15D:
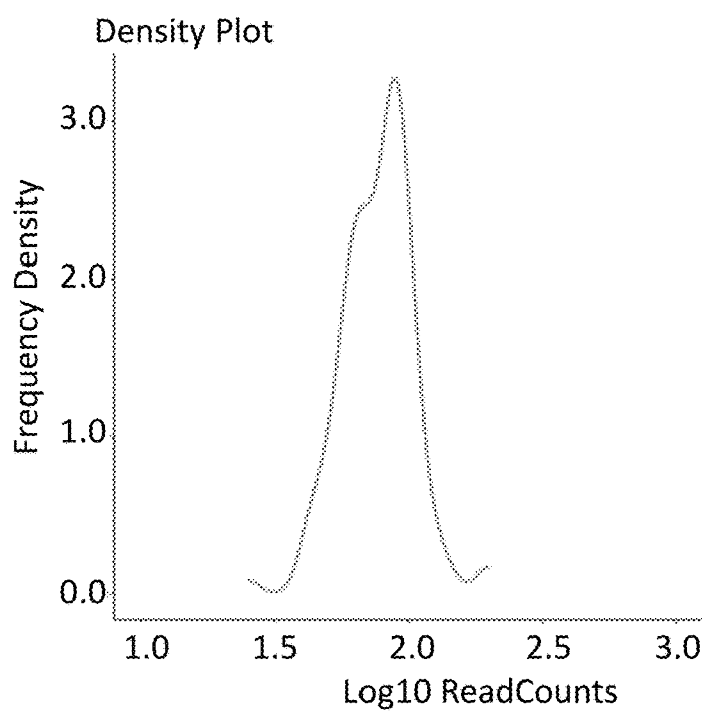
FIG. 15D are graphs of frequency density vs. log(read counts) for a 50×50 combinatorial assembly (left) and 100×100 combinatorial assembly (right).
Figure 15D:
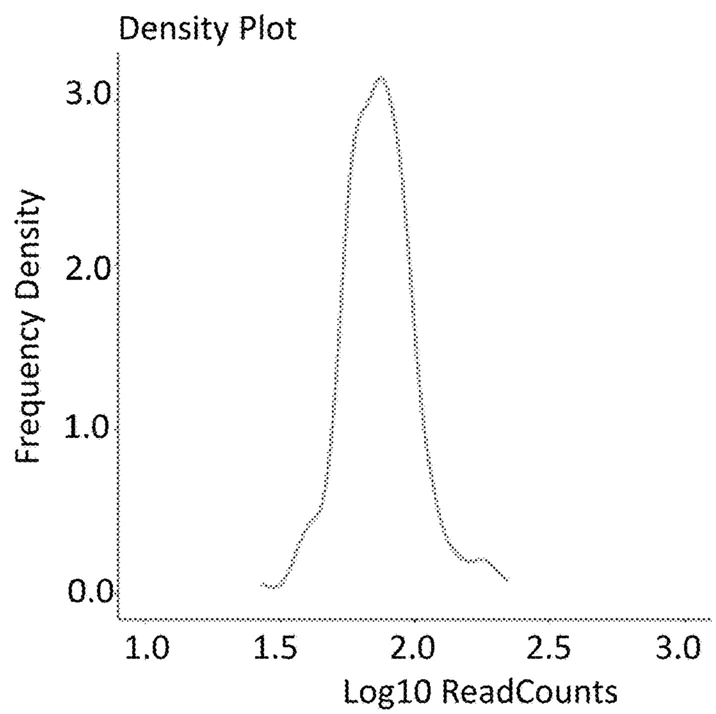

Four pools were generated of increasing complexity (4, 10, 50, 100 variants), with up to 100,000 possible combinations. Pools showed uniform assemblies (FIG. 15C, FIG. 15D, and Table 18).

TABLE 18

| Percentile Metrics | $90^{th}/10^{th}$ Percentile | $95^{th}/5^{th}$ Percentile |
|---|---|---|
| 4 × 4 | 1.62 | 1.99 |
| 10 × 10 | 2.00 | 2.37 |
| 50 × 50 | 2.03 | 2.61 |
| 100 × 100 | 1.99 | 2.59 |

Example 18: Assembling a Diverse Gene Pool of 250,000 Sequences

Figure 16A:
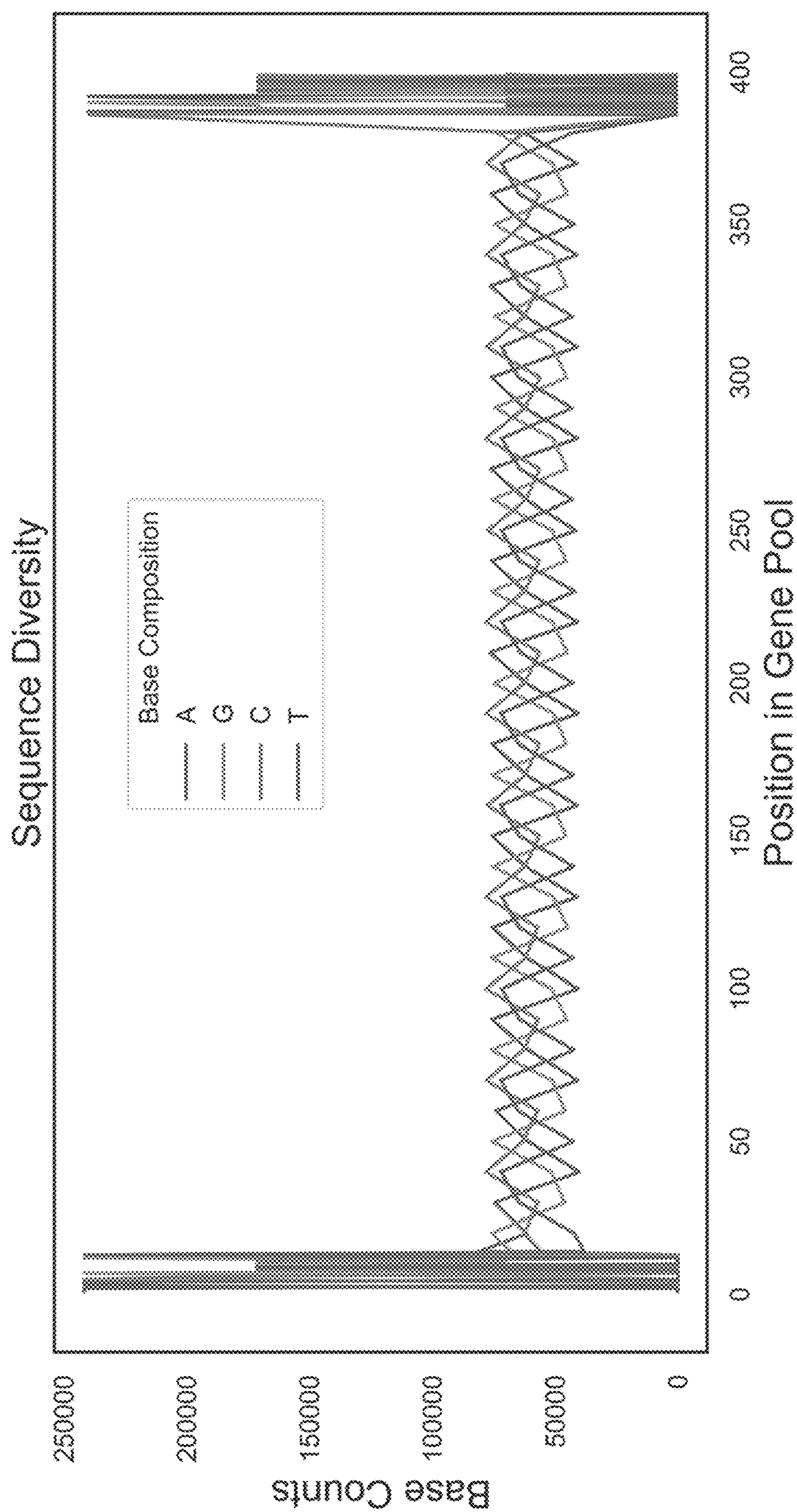
FIG. 16A is a graph of sequence diversity (base counts) as a function of position in the gene pool for a 250k sequence combinatorial library encoding for viral proteins.
Figure 16B:
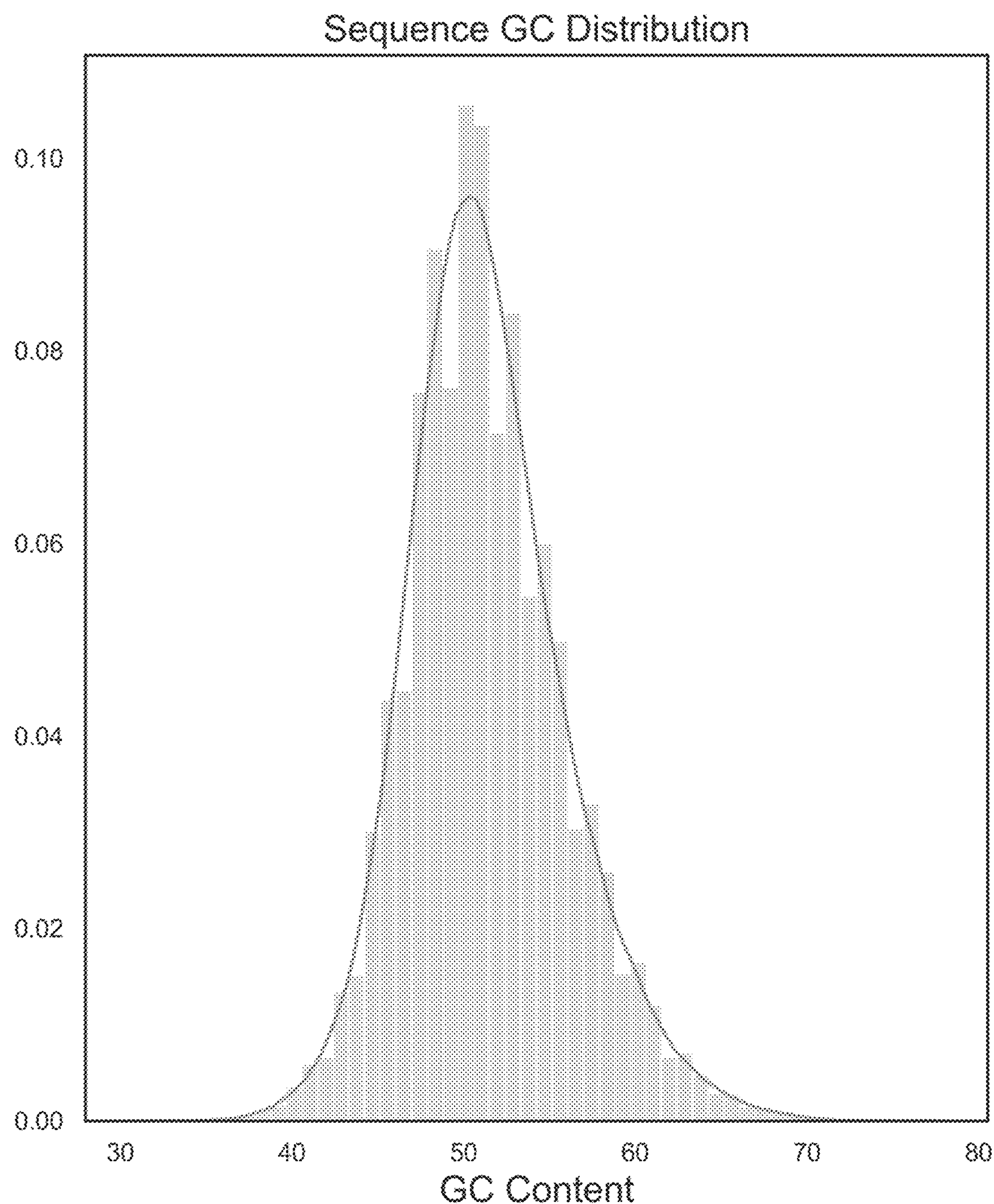
FIG. 16B is a graph of sequence representation across sequences with varying GC content for a 250k sequence combinatorial library encoding for viral proteins.
Figure 16C:
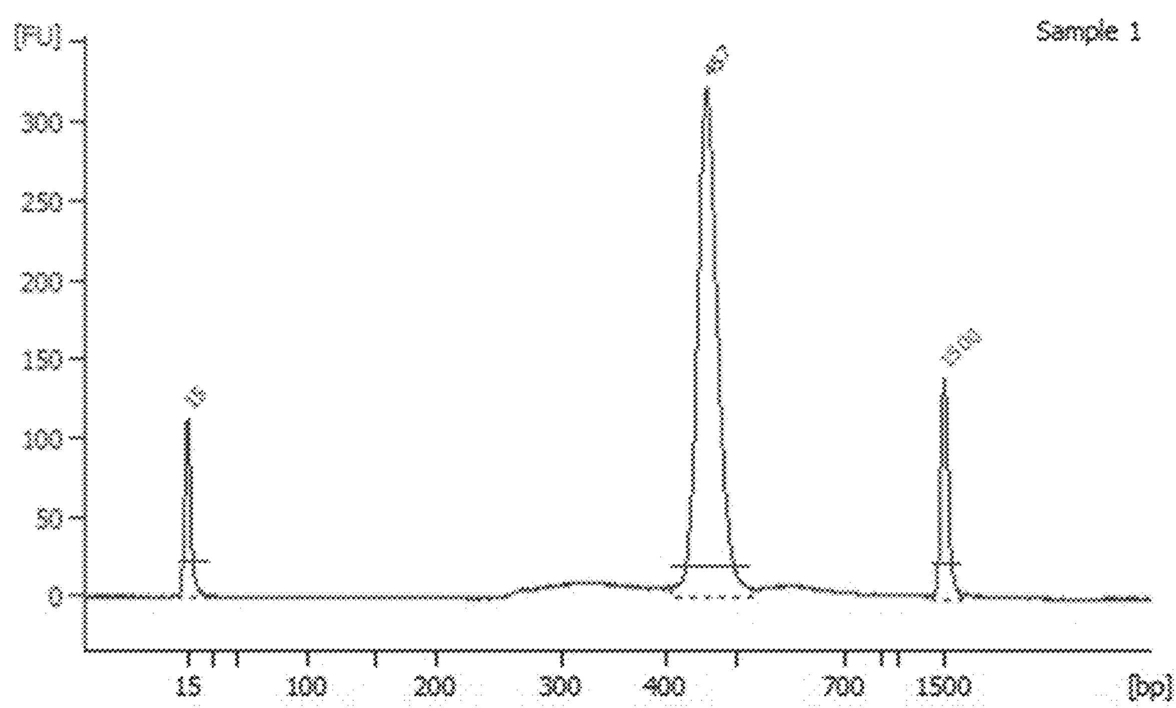
FIG. 16C is a graph of the size distribution of genes in a 250k sequence combinatorial library encoding for viral proteins.
Figure 16D:
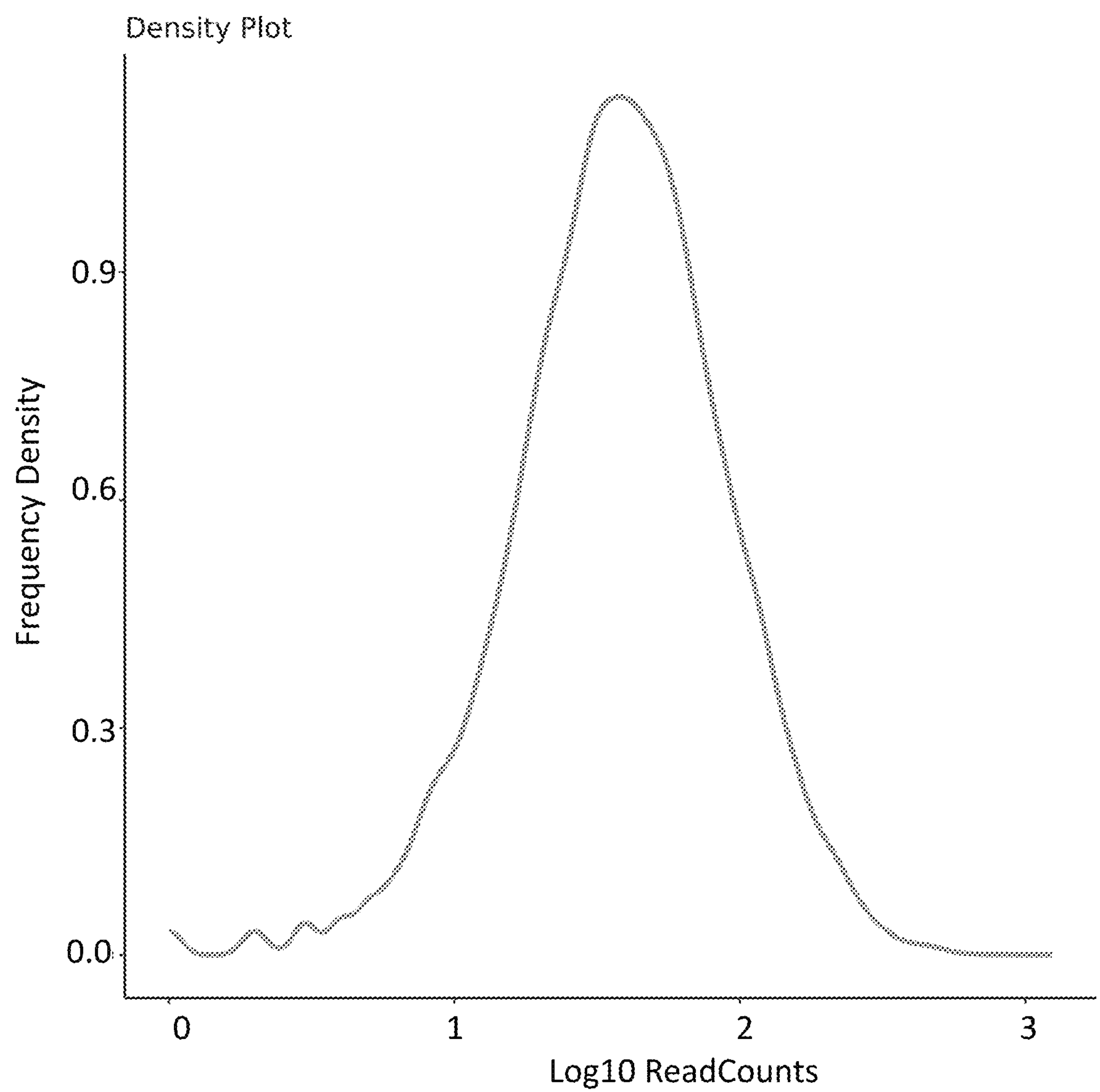
FIG. 16D is a graph of frequency density vs. log(read counts) for a 250k sequence combinatorial library encoding for viral proteins.
Figure 16E:
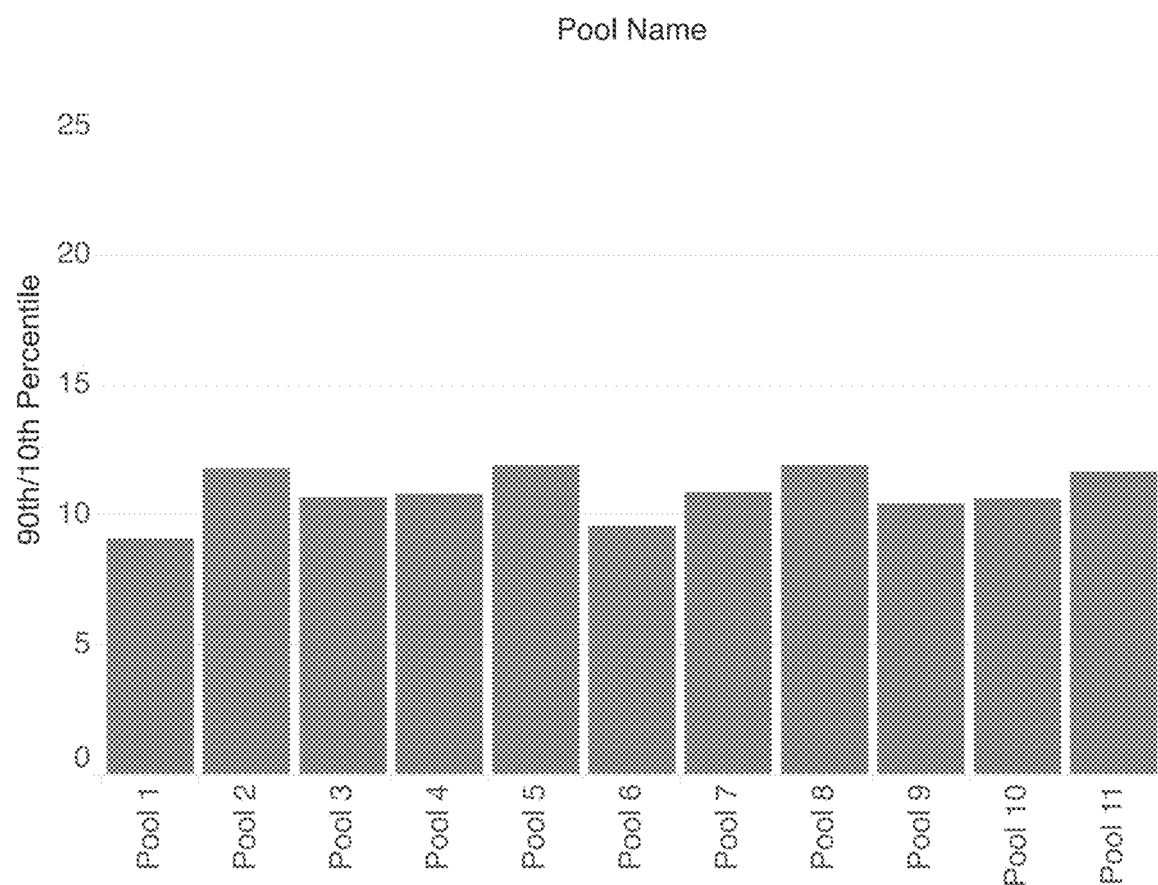
FIG. 16E is a graph of uniformity across 11 sub gene pools.
Figure 16F:
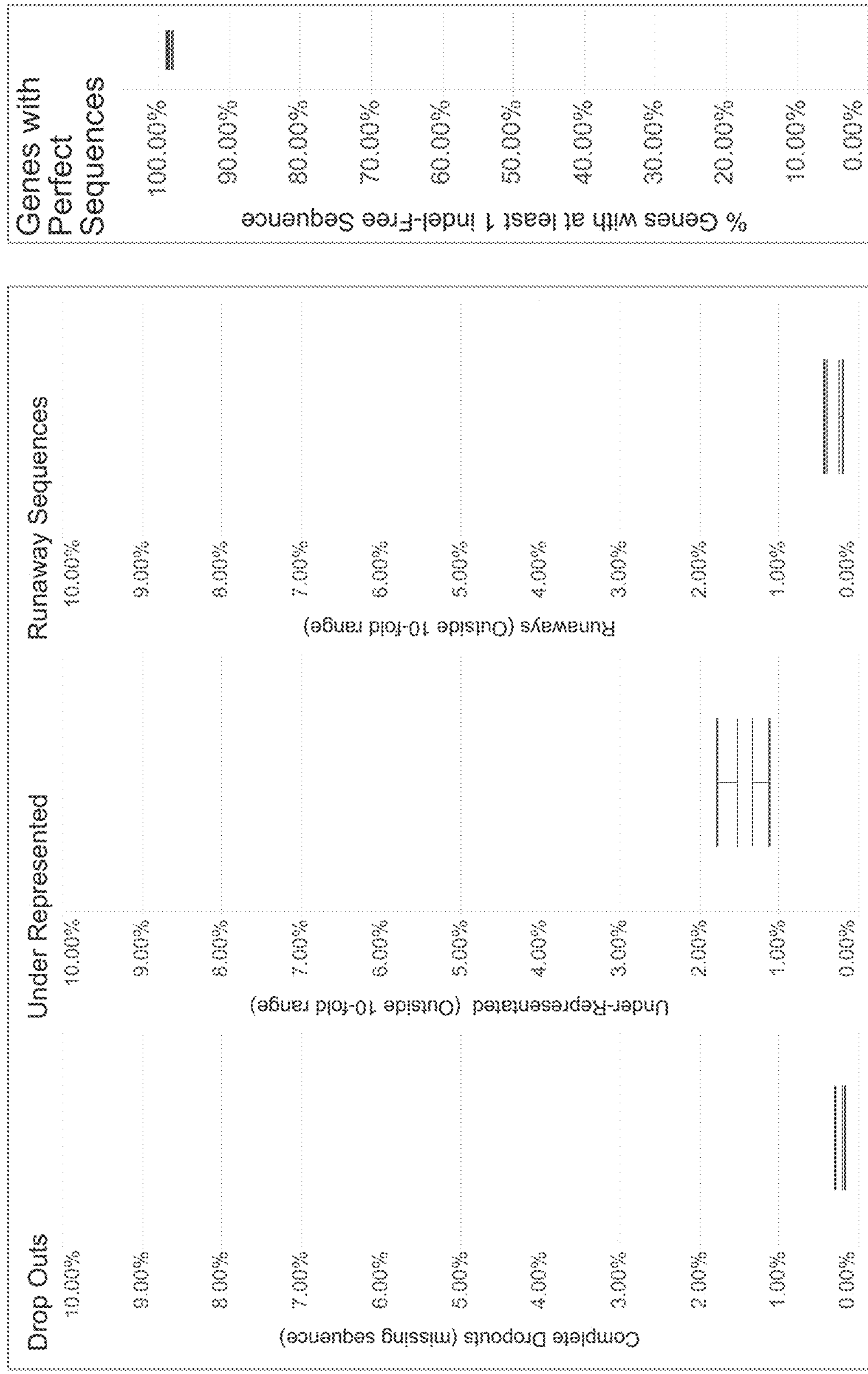
FIG. 16F are graphs of pool characteristics, including: drop outs (missing from pool), under represented (<10× of the mean), runaway (>10× of the mean), and percent genes with perfect sequences.

Following the general methods of Example 7, 250K sequences encoding for viral proteins were created through 11 sub gene pools. Sequences comprised viral protein DNA flanked first by a first adapter, and then a second adapter at the distal ends. 450 bp genes were distributed amongst pools by sequence diversity with an average of 23k genes per pool (FIG. 16A and FIG. 16B. Pools were assembled and PCR amplified, and visualized with digital DNA electrophoresis (FIG. 16C). The quality of the gene pools were evaluated with normalized 50× gene coverage (FIG. 16D and FIG. 16E). $90^{th}/10^{th}$ Percentile Ratio indicates on average, 80% of the population lies within 10.8× of the mean. The pool was additionally characterized by drop outs (missing from pool), under represented (<10× of the mean) and runaway (>10× of the mean) (FIG. 16F). On average, >98% of genes had a detected perfect sequence at 50×NGS coverage (FIG. 16F).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A method for nucleic acid assembly, comprising:

(a) providing a first plurality of polynucleotides comprising up to 2500 bases in length, wherein each polynucleotide of the first plurality of polynucleotides comprises a first terminal region of sequence homology;

(b) providing a second plurality of polynucleotides comprising up to 2500 bases in length, wherein each polynucleotide of the second plurality of polynucleotides comprises a second terminal region of sequence homology to the first terminal region of sequence homology; and (c) contacting the first plurality of polynucleotides and the second plurality of polynucleotides with a reaction mixture comprising an exonuclease, a flap endonuclease 1, a polymerase, and a ligase to assemble a library of nucleic acids, wherein at least 80% of the nucleic acids are each present in the library in an amount within 2× of a mean frequency for each of the nucleic acids in the library.

2. The method of claim 1, wherein the first plurality of polynucleotides comprises up to 100 different sequences, and wherein the second plurality of polynucleotides comprises up to 100 different sequences.

3. The method of claim 1, wherein at least 10,000 nucleic acids are assembled.

4. The method of claim 1, wherein at least 100,000 nucleic acids are assembled.

5. The method of claim 1, wherein the polymerase comprises 5' to 3' polymerase activity.

6. The method of claim 1, wherein the polymerase is a DNA polymerase.

7. The method of claim 1, wherein the ligase catalyzes joining of at least two nucleic acids.

8. A method for nucleic acid assembly, comprising:

a. de novo synthesizing a first nucleic acid comprising in 5' to 3' order: a barcode sequence, a first restriction endonuclease site, a second restriction endonuclease site, and a first hypervariable region sequence;

b. de novo synthesizing a second nucleic acid comprising in 5' to 3' order: a first region of any defined length sequence, a self-cleaving peptide sequence, a first complementary region adjacent to a first variable region sequence, and a first variable region sequence;

c. contacting the first nucleic acid and the second nucleic to generate a third nucleic acid;

d. providing a fourth nucleic acid comprising in 5' to 3' order: a vector sequence, a second complementary region adjacent to a second variable region sequence, a second variable region sequence, a second hypervariable region sequence, the first restriction endonuclease site, and the barcode sequence;

e. contacting the third nucleic acid and the fourth nucleic acid with a restriction endonuclease; and f. assembling the third nucleic acid and the fourth nucleic acid using a reaction mixture comprising one or more enzymes, comprising an exonuclease, a flap endonuclease 1, a polymerase, and a ligase.

9. The method of claim 8, wherein the first restriction endonuclease site or the second restriction endonuclease site is a Type IIS restriction endonuclease (TIIS-RE) site.

10. The method of claim 8, wherein the restriction endonuclease is a Type IIS restriction endonuclease.

11. The method of claim 8, wherein the reaction mixture comprises a ligase.

12. The method of claim 8, wherein the first hypervariable region sequence and the second hypervariable region sequence each comprises a complementary determining region (CDR), and wherein the CDR is CDR3.

13. The method of claim 8, wherein the self-cleaving peptide is P2A.

14. The method of claim 8, wherein about 100 variants of the first variable region sequence are synthesized, and wherein about 130 variants of the second variable region sequence are synthesized.

15. The method of claim 8, further comprising amplifying the nucleic acid with a first primer complementary to a first barcode sequence and a second primer wherein at least 99% of the amplicons have no deletions.

16. A method for nucleic acid assembly, comprising:

a. de novo synthesizing a first nucleic acid comprising a first variable region sequence;

b. de novo synthesizing a second nucleic acid comprising a second variable region sequence;

c. de novo synthesizing a third nucleic acid comprising in 5' to 3' order: a first region of fixed variability sequence, a first region of any defined length sequence, a self-cleaving peptide sequence, a first complementary region adjacent to a first variable region sequence, and a second region of fixed variability sequence; and d. contacting the first nucleic acid, the second nucleic acid, and the third nucleic acid with a reaction mixture comprising an exonuclease, an endonuclease, a polymerase, and a ligase, wherein the endonuclease is a flap endonuclease 1.

17. The method of claim 16, wherein the first variable region sequence or the second variable region sequence is amplified with a hypervariable region sequence.

18. The method of claim 17, wherein the hypervariable region sequence comprises a CDR, and wherein the CDR is CDR3.

19. The method of claim 16, wherein about 100 variants of the first variable region sequence are synthesized, and wherein about 130 variants of the second variable region sequence are synthesized.

20. The method of claim 16, wherein the self-cleaving peptide is P2A.

21. The method of claim 16, wherein the polymerase comprises 5' to 3' polymerase activity.

* * * * *

```
                              SEQUENCE LISTING


<160> NUMBER OF SEQ ID NOS: 4

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1

agacaatcaa ccatttgggg tggacagcct tgacctctag acttcggcat ttttttttt      60

tt                                                                    62


<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2

cgggatcctt atcgtcatcg tcgtacagat cccgacccat ttgctgtcca ccagtcatgc      60

tagccatacc atgatgatga tgatgatgag aaccccgcat ttttttttt tt             112


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

atgcggggtt ctcatcatc                                                  19


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

cgggatcctt atcgtcatcg                                                 20
```